United States Patent [19]

Bochis et al.

[11] Patent Number: 5,545,735

[45] Date of Patent: Aug. 13, 1996

[54] BENZO-FUSED LACTAMS PROMOTE RELEASE OF GROWTH HORMONE

[75] Inventors: Richard J. Bochis, East Brunswick; Paul J. Hodges, Brick; William R. Schoen, Edison; Matthew J. Wyvratt, Jr., Mountainside, all of N.J.

[73] Assignee: Merck & Co., Inc., Rahway, N.J.

[21] Appl. No.: 132,074

[22] Filed: Oct. 4, 1993

[51] Int. Cl.⁶ .................... C07D 223/16; C07D 513/04
[52] U.S. Cl. ............................ 540/490; 540/523
[58] Field of Search ..................... 540/490, 523

Primary Examiner—John M. Ford
Attorney, Agent, or Firm—Eric J. Thies; David L. Rose

[57] ABSTRACT

There are disclosed certain novel compounds identified as benzo-fused lactams which promote the release of growth hormone in humans and animals. This property can be utilized to promote the growth of food animals to render the production of edible meat products more efficient, and in humans, to increase the stature of those afflicted with a lack of a normal secretion of natural growth hormone. Growth promoting compositions containing such benzo-fused lactams as the active ingredient thereof are also disclosed.

6 Claims, No Drawings

BENZO-FUSED LACTAMS PROMOTE RELEASE OF GROWTH HORMONE

BACKGROUND OF THE INVENTION

Growth hormone, which is secreted from the pituitary, stimulates growth of all tissues of the body that are capable of growing. In addition, growth hormone is known to have the following basic effects on the metabolic process of the body:

1. Increased rate of protein synthesis in all cells of the body;
2. Decreased rate of carbohydrate utilization in cells of the body;
3. Increased mobilization of free fatty acids and use of fatty acids for energy.

A deficiency in growth hormone secretion can result in various medical disorders, such as dwarfism.

Various ways are known to release growth hormone. For example, chemicals such as arginine, L—3,4—dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering an agent which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recently, recombinant growth hormone has become available which, while no longer carrying any risk of disease transmission, is still a very expensive product which must be given by injection or by a nasal spray.

Other compounds have been developed which stimulate the release of endogenous growth hormone such as analogous peptidyl compounds related to GRF or peptides of U.S. Pat. No. 4,411,890. These peptides, while considerably smaller than growth hormones are still susceptible to various proteases. As with most peptides, their potential for oral bioavailability is low. The instant compounds are non-peptidyl agents for promoting the release of growth hormone which may be administered parenterally, nasally or by the oral route.

SUMMARY OF THE INVENTION

The instant invention covers certain benzo-fused lactam compounds which have the ability to stimulate the release of natural or endogenous growth hormone. The compounds thus have the ability to be used to treat conditions which require the stimulation of growth hormone production or secretion such as in humans with a deficiency of natural growth hormone or in animals used for food production where the stimulation of growth hormone will result in a larger, more productive animal. Thus, it is an object of the instant invention to describe the benzo-fused lactam compounds. It is a further object of this invention to describe procedures for the preparation of such compounds. A still further object is to describe the use of such compounds to increase the secretion of growth hormone in humans and animals. A still further object of this invention is to describe compositions containing the benzo-fused lactam compounds for the use of treating humans and animals so as to increase the level of growth hormone secretions. Further objects will become apparent from a reading of the following description.

DESCRIPTION OF THE INVENTION

The novel benzo-fused lactams of the instant invention are best described in the following structural formula I:

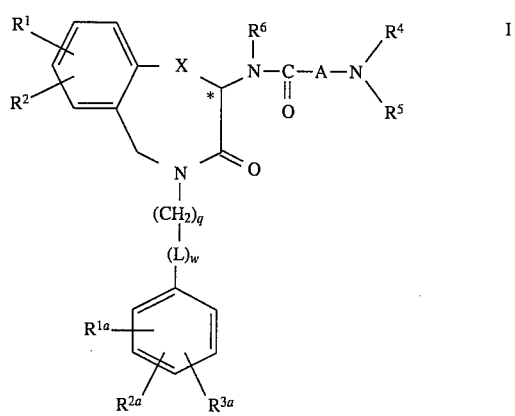

where L is

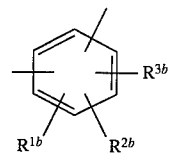

q is 0 to 4;

w is 0 or 1;

X is $CH_2$ or $S(O)_m$ where m is 0 to 2;

$R^1$, $R^2$, $R^{1a}$, $R^{2a}$, $R^{1b}$ and $R^{2b}$ are independently hydrogen, halogen, $C_1$–$C_7$ alkyl, $C_1$–$C_3$ perfluoroalkyl, $C_1$–$C_3$ perfluoroalkoxy, —$S(O)_m R^{7a}$, cyano, nitro, $R^{7b}O(CH_2)_v$—, $R^{7b}COO(CH_2)_v$—, $R^{7b}OCO(CH_2)_v$—, $R^{5b}R^{12b}N(CH_2)_v$—, $R^{7b}CON(R^{12b})(CH_2)_v$—, $R^{5b}R^{12b}NCO(CH_2)_v$—, phenyl or substituted phenyl where the substituents are from 1 to 3 of halogen, $C_1$–$C_6$ alkyl, $C_1$–$C_6$ alkoxy, or hydroxy; v is 0 to 3 and m is 0 to 2;

$R^{7a}$ and $R^{7b}$ are independently hydrogen, $C_1$–$C_3$ perfluoroalkyl, $C_1$–$C_6$ alkyl, substituted $C_1$–$C_6$ alkyl where the substituents are phenyl or substituted phenyl; phenyl or substituted phenyl where the phenyl substituents are from 1 to 3 of halogen, $C_1$–$C_6$ alkyl, $C_1$–$C_6$ alkoxy or hydroxy;

$R^{3a}$ and $R^{3b}$ are independently hydrogen, $R^9$, $C_1$–$C_6$ alkyl substituted with $R^9$, phenyl substituted with $R^9$ or phenoxy substituted with $R^9$;

$R^9$ is

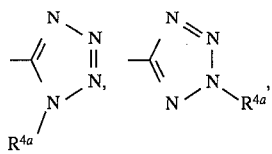

$R^{7b}O(CH_2)_v-$, $R^{7b}COO(CH_2)_v-$, $R^{7b}OCO(CH_2)_v-$,
$R^{7b}CO(CH_2)_v-$, $R^{7b}O(CH_2)_vCO-$, $R^{5b}R^{12b}N(CH_2)_v-$,
$R^{5b}R^{12b}NCO(CH_2)_v-$, $R^{5b}R^{12b}NCS(CH_2)_v-$,
$R^{5b}R^{12c}NN(R^{12b})CO(CH_2)_v-$,
$R^{5b}R^{12a}NN(R^{12b})CS(CH_2)_v-$,
$R^{5b}R^{12b}NCON(R^{12a})(CH_2)_v-$,
$R^{5b}R^{12b}NCSN(R^{12a})(CH_2)_v-$,
$R^{5b}R^{12c}NN(R^{12b})CSN(R^{12a})(CH_2)_v-$,
$R^{5b}R^{12c}NN(R^{12b})CON(R^{12a})(CH_2)_v-$,
$R^{5b}R^{12c}NN(R^{12b})COO(CH_2)_v-$,
$R^{5b}R^{12b}NCOO(CH_2)_v-$
or $R^{13}OCON(R^{12a})(CH_2)_v-$, where v is 0 to 3.
$R^{12a}$, $R^{12b}$ and $R^{12c}$ are independently $R^{5a}$, $OR^{5a}$ or $COR^{5a}$. $R^{12a}$ and $R^{12b}$, or $R^{12b}$ and $R^{12c}$, or $R^{12a}$ and $R^{12c}$, or $R^{12b}$ and $R^{5b}$, or $R^{12c}$ and $R^{5b}$, or $R^{13}$ and $R^{12a}$ can be taken together to form $-(CH_2)_r-B-(CH_2)_s-$ where B is $CHR^1$, O, $S(O)_m$ or $NR^{10}$, m is 0, 1 or 2, r and s are independently 0 to 3 and $R^1$ and $R^{10}$ are as defined.

$R^{13}$ is $C_1-C_3$ perfluoroalkyl, $C_1-C_6$ alkyl, substituted $C_1-C_6$ alkyl, where the substitutents are hydroxy, $-NR^{10}R^{11}$, carboxy, phenyl or substituted phenyl; phenyl or substituted phenyl where the substituents on the phenyl are from 1 to 3 of halogen, $C_1-C_6$ alkyl, $C_1-C_6$ alkoxy or hydroxy.

$R^{10}$ and $R^{11}$ are independently hydrogen, $C_1-C_6$ alkyl, phenyl, phenyl $C_1-C_6$ alkyl, $C_1-C_5$ alkoxycarbonyl or $C_1-C_5$ alkanoyl—$C_1-C_6$ alkyl;

$R^4$, $R^{4a}$, $R^5$, $R^{5a}$ and $R^{5b}$ are independently hydrogen, phenyl, substituted phenyl, $C_1-C_{10}$ alkyl, substituted $C_1-C_{10}$ alkyl, $C_3-C_{10}$ alkenyl, substituted $C_3-C_{10}$ alkenyl, $C_3-C_{10}$ alkynyl or substituted $C_3-C_{10}$ alkynyl where the substituents on the phenyl, alkyl, alkenyl or alkynyl are from 1 to 5 of hydroxy, $C_1-C_6$ alkoxy, $C_3-C_7$ cycloalkyl, fluoro, $R^1$, $R^2$ independently disubstituted phenyl, $R^1$, $R^2$ independently disubstituted phenyl $C_1-C_3$ alkoxy, $C_1-C_{20}$—alkanoyloxy, $C_1-C_5$ alkoxycarbonyl, carboxy, formyl or $-NR^{10}R^{11}$ where $R^1$, $R^2$, $R^{10}$ and $R^{11}$ are as defined above; or $R^4$ and $R^5$ can be taken together to form $-(CH_2)_r-B-(CH_2)_s-$ where B is $CHR^1$, O, $S(O)_m$ or $N-R^{10}$, r and s are independently 1 to 3, m is 0, 1 or 2 and $R^1$ and $R^{10}$ are as defined above;

$R^6$ is hydrogen, $C_1-C_{10}$ alkyl, phenyl or phenyl. $C_1-C_{10}$ alkyl;

A is

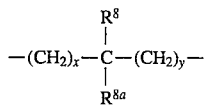

where x and y are independently 0–3;
$R^8$ and $R^{8a}$ are independently hydrogen, $C_1-C_{10}$ alkyl, trifluoromethyl, phenyl, substituted $C_1-C_{10}$ alkyl where the substitutents are from 1 to 3 of imidazolyl, indolyl, hydroxy, fluoro, $-S(O)_mR^{7a}$, $C_1-C_6$ alkoxy, $C_3-C_7$ cycloalkyl, $R^1$, $R^2$ independently disubstituted phenyl, $R^1$, $R^2$ independently disubstituted phenyl $C_1-C_3$ alkoxy, $C_1-C_5$ alkanoyloxy, $C_1-C_5$ alkoxycarbonyl, carboxy, formyl or $-NR^{10}R^{11}$ where $R^1$, $R^2$, $R^{7a}$, $R^{10}$, $R^{11}$ and m are as defined above; or $R^8$ and $R^{8a}$ can be taken together to form $-(CH_2)_t-$ where t is 2 to 6; and $R^8$ and $R^{8a}$ can independently be joined to $R^5$ to form alkylene bridges between the terminal nitrogen and the alkyl portion of the A group wherein the bridge contains from one to five carbon atoms; and pharmaceutically acceptable salts thereof.

In the above structural formula and throughout the instant specification, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The alkoxy groups specified above are intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term "halogen" is intended to include the halogen atoms fluorine, chlorine, bromine and iodine.

Certain of the above defined terms may occur more than once in the above formula and upon such occurrence each term shall be defined independently of the other.

Preferred compounds of the instant invention are realized when in the above structural formula:
q is 0 to 2;
w is 0 or 1;
X is $CH_2$ or $S(O)_m$, where m is 0 to 2;
$R^1$, $R^2$, $R^{1a}$, $R^{2a}$, $R^{1b}$ and $R^{2b}$ are independently hydrogen, halogen, $C_1-C_7$ alkyl, $C_1-C_3$ perfluoroalkyl, $-S(O)_mR^{7a}$, $R^{7b}O(CH_2)_v-$, $R^{7b}COO(CH_2)_v-$, $R^{7b}OCO(CH_2)_v-$, phenyl or substituted phenyl where the substituents are from 1 to 3 of halogen, $C_1-C_6$ alkyl, $C_1-C_6$ alkoxy, or hydroxy;

$R_{7a}$ and $R_{7b}$ are independently hydrogen, $C_1-C_3$ perfluoroalkyl, $C_1-C_6$ alkyl, substituted $C_1-C_6$ alkyl where the substituents are phenyl; phenyl and v is 0 to 3;

$R^{3a}$ and $R^{3b}$ are independently hydrogen, $R^9$, $C_1-C_6$ alkyl substituted with $R^9$, phenyl substituted with $R^9$ or phenoxy substituted with $R^9$;

$R^9$ is

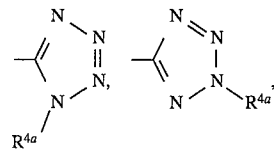

$R^{7b}O(CH_2)_v-$, $R^{7b}COO(CH_2)_v-$, $R^{7b}OCO(CH_2)_v-$,
$R^{7b}CO(CH_2)_v-$, $R^{5b}R^{12b}N(CH_2)_v-$,
$R^{5b}R^{12b}NCO(CH_2)_v-$, $R^{5b}R^{12b}NCS(CH_2)_v-$,
$R^{5b}R^{12c}NN(R^{12b})CO(CH_2)_v-$,
$R^{5b}R^{12b}NCON(R^{12a})(CH_2)_v-$,
$R^{5b}R^{12b}NCSN(R^{12a})(CH_2)_v-$,
$R^{5b}R^{12c}NN(R^{12b})CSN(R^{12a})(CH_2)_v-$,
$R^{5b}R^{12c}NN(R^{12b})CON(R^{12a})(CH_2)_v-$,
$R^{5b}R^{12c}NN(R^{12b})COO(CH_2)_v-$,
$R^{5b}R^{12b}NCOO(CH_2)_v-$
or $R^{13}OCON(R^{12a})(CH_2)_v-$, where v is 0 to 3.
$R^{12a}$, $R^{12b}$ and $R^{12c}$ are independently $R^{5a}$, $OR^{5a}$ or $COR^{5a}$. $R^{12a}$ and $R^{12b}$, or $R^{12b}$ and $R^{12c}$, or $R^{12a}$ and $R^{12c}$, or $R^{12b}$ and $R^{5b}$, or $R^{12c}$ and $R^{5b}$, or $R^{13}$ and $R^{12a}$ can be taken together to form $-(CH_2)_r-B-(CH_2)_s-$ where B is $CHR^1$, O, $S(O)_m$ or $NR^{10}$, m is 0, 1 or 2, r and s are independently 0 to 3 and R 1 and R 10 are as defined.

$R^{13}$ is $C_1-C_3$ perfluoroalkyl, $C_1-C_6$ alkyl, substituted $C_1-C_6$ alkyl, where the substituents are hydroxy, —$NR^{10}R^{11}$, carboxy, phenyl or substituted phenyl; phenyl or substituted phenyl where the substituents on the phenyl are from 1 to 3 of halogen, $C_1$–$C_6$ alkyl, $C_1$–$C_6$ alkoxy or hydroxy.

$R^{10}$ and $R^{11}$ are independently hydrogen, $C_1$–$C_6$ alkyl, phenyl $C_1$–$C_6$ alkyl, or $C_1$–$C_5$ alkanoyl—$C_1$–$C_6$ alkyl;

$R^4$, $R^{4a}$, $R^5$, $R^{5a}$ and $R^{5b}$ are independently hydrogen, phenyl, substituted phenyl, $C_1$–$C_{10}$ alkyl, substituted $C_1$–$C_{10}$ alkyl where the substituents on the alkyl or phenyl are from 1 to 5 of hydroxy, $C_1$–$C_6$ alkoxy, $C_3$–$C_7$ cycloalkyl, fluoro, $R^1$, $R^2$ independently disubstituted phenyl, $R^1$, $R^2$ independently disubstituted phenyl $C_1$–$C_3$ alkoxy, $C_1$–$C_{20}$—alkanoyloxy, $C_1$–$C_5$ alkoxycarbonyl, carboxy or formyl; $R^4$ and $R^5$ can be taken together to form —$(CH_2)_r$—B—$(CH_2)_s$— where B is $CHR^1$, O, $S(O)_m$ or N—$R^{10}$, r and s are independently 1 to 3, m is 0, 1 or 2 and $R^1$ and $R^{10}$ are as defined above;

$R^6$ is hydrogen, $C_1$–$C_{10}$ alkyl or phenyl $C_1$–$C_{10}$ alkyl;

A is

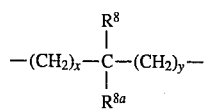

where x and y are independently 0–2;

$R^8$ and $R^{8a}$ are independently hydrogen, $C_1$–$C_{10}$ alkyl, substituted $C_1$–$C_{10}$ alkyl where the substitutents are from 1 to 3 of imidazolyl, indolyl, hydroxy, fluoro, —$S(O)_mR^{7a}$, $C_1$–$C_6$ alkoxy, $C_3$–$C_7$ cycloalkyl, $R^1$, $R^2$ independently disubstituted phenyl, $R^1$, $R^2$ independently disubstituted phenyl $C_1$–$C_3$ alkoxy, $C_1$–$C_5$ alkanoyloxy, $C_1$–$C_5$ alkoxycarbonyl, carboxy, formyl or —$NR^{10}R^{11}$ where $R^1$, $R^2$, $R^{7a}$, $R^{10}$, $R^{11}$ and m are as defined above; or $R^8$ and $R^{8a}$ can be taken together to form —$(CH_2)_t$— where t is 2 to 4; and $R^8$ and $R^{8a}$ can independently be joined to $R^5$ to form alkylene bridges between the terminal nitrogen and the alkyl portion of the A group wherein the bridge contains from one to five carbon atoms; and pharmaceutically acceptable salts thereof.

Additional preferred compounds are realized in the above structural formula when:

q is 0 to 2;
w is 0 or 1;
X is $CH_2$ or $S(O)_m$, where m is 0 or 1;
$R^1$, $R^2$, $R^{1a}$, $R^{2a}$, $R^{1b}$ and $R^{2b}$ are independently hydrogen, halogen, $C_1$–$C_7$ alkyl, $C_1$–$C_3$ perfluoroalkyl, —$S(O)_mR^{7a}$, $R^{7b}O(CH_2)_v$—, $R^{7b}COO(CH_2)_v$—, $R^{7b}OCO(CH_2)_v$—, phenyl or substituted phenyl where the substituents are from 1 to 3 of halogen, $C_1$–$C_6$ alkyl, $C_1$–$C_6$ alkoxy, or hydroxy;
$R^{7a}$ and $R^{7b}$ are independently hydrogen, $C_1$–$C_6$ alkyl or substituted $C_1$–$C_6$ alkyl where the substitutents are phenyl and v is 0 to 2;
$R^{3a}$ and $R^{3b}$ are independently hydrogen, $R^9$, $C_1$–$C_6$ alkyl substituted with $R^9$ or phenoxy substituted with $R^9$;
$R^9$ is

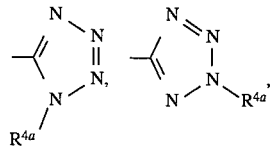

$R^{7b}O(CH_2)_v$—, $R^{7b}COO(CH_2)_v$—, $R^{7b}OCO(CH_2)_v$—, $R^{7b}CO(CH_2)_v$—, $R^{5b}R^{12b}N(CH_2)_v$—, $R^{5b}R^{12b}NCO(CH_2)_v$—, $R^{5b}R^{12c}NN(R^{12b})CO(CH_2)_v$—, $R^{5b}R^{12b}NCON(R^{12a})(CH_2)_v$—, $R^{5b}R^{12c}NN(R^{12b})CSN(R^{12a})(CH_2)_v$—, $R^{5b}R^{12c}NN(R^{12b})CON(R^{12a})(CH_2)_v$—, $R^{5b}R^{12c}NN(R^{12b})COO(CH_2)_v$—, $R^{5b}R^{12b}NCOO(CH_2)_v$— or $R^{13}OCON(R^{12a})(CH_2)_v$—, where v is 0 to 2.

$R^{12a}$, $R^{12b}$ and $R^{12c}$ are independently $R^{5a}$ or $OR^{5a}$. $R^{12a}$ and $R^{12b}$, or $R^{12b}$ and $R^{12c}$, or $R^{12a}$ and $R^{12c}$, or $R^{12b}$ and $R_{5b}$, or $R^{12c}$ and $R^{5b}$, or $R^{13}$ and $R^{12a}$ can be taken together to form —$(CH_2)_r$—B—$(CH_2)_s$— where B is CHR 1, 0, $S(O)_m$ or $NR^{10}$, m is 0, 1 or 2, r and s are independently 0 to 2 and $R^1$ and $R^{10}$ are as defined.

$R^{13}$ is $C_1$–$C_6$ alkyl, substituted $C_1$–$C_6$ alkyl, where the substitutents are phenyl or substituted phenyl; phenyl or substituted phenyl where the substituents on the phenyl are from 1 to 3 of halogen, $C_1$–$C_6$ alkyl, $C_1$–$C_6$ alkoxy or hydroxy.

$R^{10}$ and $R^{11}$ are independently hydrogen, $C_1$–$C_6$ alkyl, phenyl $C_1$–$C_6$ alkyl, or $C_1$–$C_5$ alkanoyl—$C_1$–$C_6$ alkyl;

$R^4$, $R^{4a}$, $R^5$, $R^{5a}$ and $R^{5b}$ are independently hydrogen, $C_1$–$C_{10}$ alkyl or substituted $C_1$–$C_{10}$ alkyl where the substituents are from 1 to 5 of hydroxy, $C_1$–$C_6$ alkoxy, fluoro, $R^1$, $R^2$ independently disubstituted phenyl, $C_1$–$C_{20}$—alkanoyloxy, $C_1$–$C_5$ alkoxycarbonyl or carboxy; where $R^1$ and $R^2$ are as defined above;

$R^6$ is hydrogen or $C_1$–$C_{10}$ alkyl;

A is

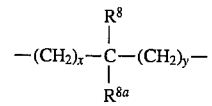

where x and y are independently 0–1;

$R^8$ and $R^{8a}$ are independently hydrogen, $C_1$–$C_{10}$ alkyl, substituted $C_1$–$C_{10}$ alkyl where the substitutents are from 1 to 3 of imidazolyl, indolyl, hydroxy, fluoro, —$S(O)_mR^{7a}$, $C_1$–$C_6$ alkoxy, $C_3$–$C_7$ cycloalkyl, $R^1$, $R^2$ independently disubstituted phenyl, $R^1$, $R^2$ independently disubstituted phenyl $C_1$–$C_3$ alkoxy, $C_1$–$C_5$ alkanoyloxy, $C_1$–$C_5$ alkoxycarbonyl, carboxy, formyl or —$NR^{10}R^{11}$ where: $R^1$, $R^2$, $R^{7a}$, $R^{10}$, $R^{11}$ and m are as defined above; or $R^8$ and $R^8a$ can be taken together to form —$(CH_2)_t$— where t is 2; and $R^8$ and $R^{8a}$ can independently be joined to $R^5$ to form alkylene bridges between the terminal nitrogen and the alkyl portion of the A group wherein the bridge contains from one to five carbon atoms; and pharmaceutically acceptable salts thereof.

Still further preferred compounds of the instant invention are realized in the above structural formula when;

q is 1;
w is 1;
X is $CH_2$ or $S(O)_m$, where m is 0 or 1;
$R^1$, $R^2$, $R^{1a}$, $R^{2a}$, $R^{1b}$ and $R^{2b}$ are independently hydrogen, halogen, $C_1$–$C_7$ alkyl, $C_1$–$C_3$ perfluoroalkyl, —$S(O)_mR^{7a}$, $R^{7b}O(CH_2)_v$—, $R^{7b}COO(CH_2)_v$—, phenyl or substituted phenyl where the substituents are from 1 to 3 of halogen, $C_1$–$C_6$ alkyl, $C_1$–$C_6$ alkoxy, or hydroxy;
$R^{7a}$ and $R^{7b}$ are independently hydrogen, $C_1$–$C_6$ alkyl or substituted $C_1$–$C_6$ alkyl where the substitutents are phenyl and v is 0 or 1;
$R^{3a}$ and $R^{3b}$ are independently hydrogen, $R^9$ or $C_1$–$C_6$ alkyl substituted with $R^9$;

$R^9$ is

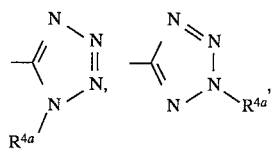

$R^{7b}O(CH_2)_v$—, $R^{7b}COO(CH_2)_v$—, $R^{7b}OCO(CH_2)_v$—, $R^{7b}CO(CH_2)_v$—, $R^{5b}R^{12b}N(CH_2)_v$—, $R^{5b}R^{12b}NCO(CH_2)_v$—, $R^{5b}R^{12c}NN(R^{12b})CO(CH_2)_v$—, $R^{5b}R^{12b}NCON(R^{12a})(CH_2)_v$—, $R^{5b}R^{12c}NN(R^{12b})CON(R^{12a})(CH_2)_v$—, $R^{5b}R^{12c}NN(R^{12b})COO(CH_2)_v$—, $R^{5b}R^{12b}NCOO(CH_2)_v$—
or $R^{13}OCON(R^{12a})(CH_2)_v$—, where v is 0 to 2.

$R^{12a}$, $R^{12b}$ and $R^{12c}$ are independently $R^{5a}$. $R^{12a}$ and $R^{12b}$, or $R^{12b}$ and $R^{12c}$, or $R^{12a}$ and $R^{12c}$, or $R^{12b}$ and $R^{5b}$, or $R^{12c}$ and $R^{5b}$, or $R^{13}$ and $R^{12a}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 2 and $R^1$ and $R^{10}$ are as defined.

$R^{13}$ is $C_1$–$C_6$ alkyl, substituted $C_1$–$C_6$ alkyl, where the substitutents are phenyl or substituted phenyl; phenyl or substituted phenyl where the substituents on the phenyl are from 1 to 3 of halogen, $C_1$–$C_6$ alkyl, $C_1$–$C_6$ alkoxy or hydroxy.

$R^{10}$ and $R^{11}$ are independently hydrogen, $C_1$–$C_6$ alkyl or $C_1$–$C_5$ alkanoyl—$C_1$–$C_6$ alkyl;

$R^4$, $R^{4a}$, $R^5$, $R^{5a}$ and $R^{5b}$ are independently hydrogen, $C_1$–$C_{10}$ alkyl or substituted $C_1$–$C_{10}$ alkyl where the substituents are from 1 to 3 of hydroxy, $C_1$–$C_3$ alkoxy, fluoro, $R^1$, $R^2$ independently disubstituted phenyl, $C_1$–$C_{20}$—alkanoyloxy, $C_1$–$C_5$ alkoxycarbonyl or carboxy; where $R^1$ and $R^2$ are as defined above;

$R^6$ is hydrogen;

A is

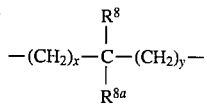

where x and y are independently 0–1;

$R^8$ and $R^{8a}$ are independently hydrogen, $C_1$–$C_{10}$ alkyl, substituted $C_1$–$C_{10}$ alkyl where the substitutents are from 1 to 3 of imidazolyl, indolyl, hydroxy, fluoro, —$S(O)_mR^{7a}$, $C_1$–$C_6$ alkoxy, $C_3$–$C_7$ cycloalkyl, $R^1$, $R^2$ independently disubstituted phenyl, $C_1$–$C_5$ alkanoyloxy, $C_1$–$C_5$ alkoxycarbonyl or carboxy, where $R^1$, $R^2$, $R^{7a}$, and m are as defined; or $R^8$ and $R^{8a}$ can be taken together to form —$(CH_2)_t$— where t is 2; and $R^8$ and $R^{8a}$ can independently be joined to $R^5$ to form alkylene bridges between the terminal nitrogen and the alkyl portion of the A group wherein the bridge contains from one to five carbon atoms; and pharmaceutically acceptable salts thereof.

Representative preferred growth hormone releasing compounds of the present invention include the following:

1. 3-Amino-3-methyl-N-[2,3,4,5-tetrahydro-3-oxo-2-[[2'-(1H-tetrazol- 5-yl)[1,1'-biphenyl]-4-yl]methyl]-1H-2-benzazepin-4(R)-yl]butanamide;
2. 2-Amino-2-methyl-N-[2,3,4,5-tetrahydro-3-oxo-2-[[2'-(1H-tetrazol- 5-yl)[1,1'-biphenyl]-4-yl]methyl]-1H-2-benzazepin-4(R)-yl]propanamide;
3. 3-[2(R)-Hydroxypropyl]amino-3-methyl-N-[2,3,4,5-tetrahydro- 3-oxo-2-[[2'-(1H-tetrazol-5-yl)[1,1'-biphenyl]-4-yl]-methyl]- 1H-2-benzazepin-4(R)-yl]butanamide;
4. 3-[2(S),3-Dihydroxypropyl]amino-3-methyl-N-[2,3,4,5-tetrahydro- 3-oxo-2-[[2'-(1H-tetrazol-5-yl)[1,1'-biphenyl]4-yl]methyl]-1H-2-benzazepin-4(R)-yl]butanamide;
5. 3-Amino-3-methyl-N-[2,3,4,5-tetrahydro-7-methoxy-3-oxo- 2-[[2'-(1H-tetrazol-5-yl)[1,1'-biphenyl]-4-yl]methyl]- 1H-2-benzazepin-4(R)-yl]butanamide;
6. 2-Amino-2-methyl-N-[2,3,4,5-tetrahydro-7-methoxy-3-oxo- 2-[[2'-(1H-tetrazol-5-yl)[1,1'-biphenyl]-4-yl]methyl]- 1H-2-benzazepin-4(R)-yl]propanamide;
7. 3-[2(R)-Hydroxypropyl]amino-3-methyl-N-[2,3,4,5-tetrahydro- 7-methoxy-3-oxo-2-[[2'-(1H-tetrazol-5-yl)[1,1'-biphenyl]-4-yl]methyl]-1H-2-benzazepin-4(R)-yl]-butanamide;
8. 3-[2(S),3-Dihydroxypropyl]amino-3-methyl-N-[2,3,4,5-tetrahydro- 7-methoxy-3-oxo-2-[[2'-(1H-tetrazol-5-yl)[1,1'-biphenyl]-4-yl]methyl]-1H-2-benzazepin-4(R)-yl]-butanamide;
9. 3-Amino-3-methyl-N-[2,3,4,5-tetrahydro-7-methylthio-3-oxo- 2-[[2'-(1H-tetrazol-5-yl)[1,1'-biphenyl]-4-yl]methyl]- 1H-2-benzazepin-4(R)-yl]butanamide;
10. 2-Amino-2-methyl-N-[2,3,4,5-tetrahydro-7-methylthio-3-oxo- 2-[[2'-(1H-tetrazol-5-yl)[1,1'-biphenyl]-4-yl]methyl]- 1H-2-benzazepin-4(R)-yl]propanamide;
11. 3-[2(R)-Hydroxypropyl]amino-3-methyl-N-[2,3,4,5-tetrahydro- 7-methylthio-3-oxo-2-[[2'-(1H-tetrazol-5-yl)[1,1'-biphenyl] -4-yl]methyl]-1H-2-benzazepin-4(R)-yl]-butanamide;
12. 3-[2(S),3-Dihydroxypropyl]amino-3-methyl-N-[2,3,4,5 -tetrahydro-7-methylthio-3-oxo-2-[[2'-(1H-tetrazol-5-yl)-[ 1,1'-biphenyl]-4-yl]methyl]-1H-2-benzazepin-4(R)-yl]-butanamide;
13. 3-Amino-3-methyl-N-[2,3,4,5-tetrahydro-7-fluoro-3-oxo- 2-[[2'-(1H-tetrazol-5-yl)[1,1'-biphenyl]-4-yl]methyl]-1H-2-benzazepin- 4(R)-yl]butanamide;
14. 2-Amino-2-methyl-N-[2,3,4,5-tetrahydro-7-fluoro-3-oxo- 2-[[2'-(1H-tetrazol-5-yl)[1,1'-biphenyl]-4-yl]methyl]-1H-2-benzazepin- 4(R)-yl]propanamide;
15. 3-[2(R)-Hydroxypropyl]amino-3-methyl-N-[2,3,4,5-tetrahydro- 7-fluoro-3-oxo-2-[[2'-(1H-tetrazol-5-yl)[1,1'-biphenyl]-4-yl]methyl]-1H-2-benzazepin-4(R)-yl]-butanamide;
16. 3-[2(S),3-Dihydroxypropyl]amino-3-methyl-N-[2,3,4,5-tetrahydro- 7-fluoro-3-oxo-2-[[2'-(1H-tetrazol-5-yl)[1,1'-biphenyl]-4-yl]methyl]-1H-2-benzazepin-4(R)-yl]-butanamide;
17. N-Ethyl-4'-[[4(R)-[(3-amino-3-methyl-1-oxobutyl)amino]- 2,3,4,5-tetrahydro-3-oxo-1H-2-benzazepin-2-yl]methyl]-[1,1'-biphenyl]-2-carboxamide;
18. N-Ethyl-4'-[[4(R)-[(2-amino-2-methyl-1-oxopropyl)amino]-2,3,4,5-tetrahydro-3-oxo-1H-2-benzazepin-2-yl]-methyl][1,1'-biphenyl]-2-carboxamide;
19. N-Ethyl-4'-[[ 4(R)-[[[2(R)-hydroxypropyl]amino]-3-methyl-1-oxobutyl]amino]-2,3,4,5-tetrahydro-3-oxo- 1H-2 -benzazepin-2-yl]methyl][1,1'-biphenyl]-2-carboxamide;
20. N-Ethyl-4'-[[4(R)-[[[[2(S),3-dihydroxypropyl]amino] -3-methyl- 1-oxobutyl)amino]-2,3,4,5-tetrahydro-3-oxo-1H-2-benzazepin- 2-yl]methyl][1,1'-biphenyl]-2-carboxamide;
21. N-Ethyl-4'-[[4(R)-[(2-amino-2-methyl-1-oxopropyl)amino]-2,3,4,5-tetrahydro-7-methylthio-3-oxo-1H-2- benzazepin-2-yl]methyl][1,1'-biphenyl]-2-carboxamide;

22. N-Ethyl-4'-[[4(R)-[[[[2(R)-hydroxypropyl]amino]-3-methyl-1-oxobutyl]amino]-2,3,4,5-tetrahydro-7-methylthio- 3-oxo-1H-2-benzazepin-2-yl]methyl][1,1'-biphenyl]-2-carboxamide;

23. N-Ethyl-4'-[[4(R)-[[[[2(S),3-dihydroxypropyl]amino]-3-methyl- 1-oxobutyl)amino]-2,3,4,5-tetrahydro-7-methylthio- 3-oxo-1H-2-benzazepin-2-yl]methyl][1,1'-biphenyl]-2-carboxamide;

24. N-Ethyl-4'-[[4(R)-[(3-amino-3-methyl-1-oxobutyl)amino]- 2,3,4,5-tetrahydro-7-methoxy-3-oxo-1H-2-benzazepin-2-yl]methyl][1,1'-biphenyl]-2-carboxamide;

25. N-Ethyl-4'-[[4(R)-[[[[2(R)-hydroxypropyl]amino]-3-methyl- 1 -oxobutyl]amino]-2,3,4,5-tetrahydro-7-methoxy-3-oxo- 1H-2-benzazepin-2-yl]methyl][1,1'-biphenyl]-2-carboxamide;

26. N-Ethyl-4'-[[4(R)-[[[[2(S),3-dihydroxypropyl]amino]-3-methyl- 1-oxobutyl)amino]-2,3,4,5-tetrahydro-7-methoxy- 3-oxo- 1H-2-benzazepin-2-yl ]methyl][1,1'-biphenyl]-2-carboxamide;

27. N-Ethyl-4'-[[4(R)-[(3-amino-3-methyl-1-oxobutyl)amino]- 2,3,4,5-tetrahydro-7-fluoro-3-oxo-1H-2-benzazepin-2-yl]-methyl] [1,1'-biphenyl]-2-carboxamide;

28. N-Ethyl-4'-[[4(R)-[[[[2(R)-hydroxypropyl]amino]-3-methyl- 1-oxobutyl]amino]-2,3,4,5-tetrahydro-7-fluoro-3-oxo- 1H-2-benzazepin-2-yl]methyl][1,1'-biphenyl]-2-carboxamide;

29. N-Ethyl-4'-[[4(R)-[[[[2(S),3-dihydroxypropyl]amino] -3-methyl- 1-oxobutyl)amino]-2,3,4,5-tetrahydro-7-fluoro-3-oxo- 1H-2-benzazepin-2-yl]methyl][ 1,1'-biphenyl]-2-carboxamide;

30. 2-Amino-2-methyl-N-[ 2,3,4,5-tetrahydro-3-oxo-2-[ [2'-hydroxymethyl[ 1,1'-biphenyl]-4-yl]methyl]-1H-2-benzazepin- 4(R)-yl]propanamide;

31. 3-[2(R)-Hydroxypropyl]amino-3-methyl-N-[2,3,4,5-tetrahydro- 3-oxo-2-[[2'-hydroxymethyl[1,1'-biphenyl]-4-yl]-methyl] -1H-2-benzazepin-4(R)-yl]butanamide;

32. 3-[2(S),3-Dihydroxypropyl]amino-3-methyl-N-[2,3,4,5-tetrahydro- 3-oxo-2-[[2'-hydroxymethyl[1,1'-biphenyl]-4-yl]methyl]-1H-2-benzazepin-4(R)-yl]butanamide;

33. 3-Amino-3-methyl-N-[2,3,4,5-tetrahydro-7-methylthio-3-oxo- 2-[[2'-hydroxymethyl[1,1'-biphenyl]-4-yl]methyl]-1H- 2-benzazepin-4(R)-yl]butanamide;

34. 3-[2(R)-Hydroxypropyl]amino-3-methyl-N-[2,3,4,5-tetrahydro- 7-methoxy-3-oxo-2-[[2'-hydroxymethyl[1,1'-biphenyl]-4-yl]methyl]-1H-2-benzazepin-4(R)-yl]-butanamide;

35. 3-[2(S),3-Dihydroxypropyl]amino-3-methyl-N-[2,3,4,5-tetrahydro- 7-trifluoromethyl-3-oxo-2-[[2'-hydroxy-methyl[ 1,1'-biphenyl]-4-yl]methyl]-1H-2-benzazepin-4(R)-yl]butanamide;

36. 3-Amino-3-methyl-N-[2,3,4,5-tetrahydro-2-[[2'-[[(methylamino)carbonyl]amino][1,1'-biphenyl]-4-yl]methyl]-3-oxo- 1H-2-benzazepin-4(R)-yl]butanamide;

37. 3-[2(R)-Hydroxypropyl]amino-3-methyl-N-[2,3,4,5-tetrahydro- 2-[[2'-[[(methylamino)carbonyl]amino][1,1'-biphenyl]-4-yl]methyl]-3-oxo-1H-2-benzazepin-4(R)-yl]-butanamide;

38. 3-[2(S),3-Dihydroxypropyl]amino-3-methyl-N-[2,3,4,5-tetrahydro- 2-[[2'-[[(methylamino)carbonyl]amino][1,1'-biphenyl]-4-yl]methyl]-3-oxo-1H-2-benzazepin-4(R)-yl]-butanamide;

39. 2-Amino-2-methyl-N-[2,3,4,5-tetrahydro-7-fluoro-2-[[2'-[[(methylamino)carbonyl]amino][1,1'-biphenyl]-4-yl]-methyl] -3-oxo-1H-2-benzazepin-4(R)-yl]propanamide;

40. 3-[2(R)-Hydroxypropyl]amino-3-methyl-N-[2,3,4,5-tetrahydro- 7-fluoro-2-[[2'-[[ (methylamino)carbonyl]amino]-[ 1,1'-biphenyl]-4-yl]methyl]-3-oxo-1H-2-benzazepin-4(R)-yl]butanamide;

41. 3-[2(S),3-Dihydroxypropyl]amino-3-methyl-N-[2,3,4,5-tetrahydro- 7-fluoro-2-[[2'-[[(methylamino)carbonyl]-amino][1,1'-biphenyl]4-yl]methyl]-3-oxo-1H-2-benzazepin- 4(R)-yl]butanamide;

42. 3-Amino-3-methyl-N-[2,3,4,5-tetrahydro-7-methylthio-2-[[2'-[[(methylamino)carbonyl]amino][1,1'-biphenyl]-4-yl]-methyl]-3-oxo-1H-2-benzazepin-4(R)-yl]butanamide;

43. 2-Amino-2-methyl-N-[2,3,4,5-tetrahydro-7-methylthio-2-[[2'-[[(methylamino)carbonyl]amino][1,1'-biphenyl]-4-yl]-methyl] -3-oxo-1H-2-benzazepin-4(R)-yl]propanamide;

44. 3-[2(S),3-Dihydroxypropyl]amino-3-methyl-N-[2,3,4,5-tetrahydro- 7-methylthio-2-[[2'-[[(methylamino)carbonyl]-amino][1,1'-biphenyl]-4-yl]methyl]-3-oxo-1H-2-benzazepin- 4(R)-yl]butanamide;

45. 2-Amino-2-methyl-N-[2,3,4,5-tetrahydro-7-methoxy-2-[[2'-[[(methylamino)carbonyl]amino][1,1'-biphenyl]-4-yl]-methyl] -3-oxo-1H-2-benzazepin-4(R)-yl]propanamide;

46. 3-[2(R)-Hydroxypropyl]amino-3-methyl-N-[2,3,4,5-tetrahydro- 7-methoxy-2-[[2'-[[ (methylamino)carbonyl]amino ]-[ 1,1 '-biphenyl]-4-yl]methyl]-3-oxo-1H-2-benzazepin-4(R)-yl]butanamide;

47. 3-[2(S),3-Dihydroxypropyl]amino-3-methyl-N-[2,3,4,5-tetrahydro- 7-methoxy-2-[[2'-[[(methylamino)carbonyl]-amino][1,1'-biphenyl]-4-yl]methyl]-3-oxo-1H-2-benzazepin- 4(R)-yl]butanamide;

48. 3-[2(R)-Hydroxypropyl]amino-3-methyl-N-[2,3,4,5-tetrahydro- 2-[[ 2'-[ (morpholinocarbonyl)amino ] [ 1,1'-biphenyl]- 4-yl]methyl] -3-oxo-1H-2-benzazepin-4(R)-yl]butanamide;

49. 3-[2(S),3-Dihydroxypropyl]amino-3-methyl-N-[2,3,4,5-tetrahydro- 2-[[2'-[(morpholinocarbonyl)amino][1, 1'-biphenyl]-4-yl]methyl]-3-oxo-1H-2-benzazepin-4(R)-yl]-butanamide;

50. 3-[2(R)-Hydroxypropyl]amino-3-methyl-N-[2,3,4,5-tetrahydro- 2-[[2'-[[(2-hydroxyethylamino)carbonyl]amino][1,1'-biphenyl]-4-yl]methyl]-3-oxo-1H-2-benzazepin-4(R)-yl]-butanamide;

51. 3-[2(S),3-Dihydroxypropyl]amino-3-methyl-N-[2,3,4,5-tetrahydro- 2-[[(2-hydroxyethylamino)carbonyl]amino][ 1,1'-biphenyl]-4-yl]methyl]-3-oxo-1H-2-benzazepin-4(R)-yl]-butanamide;

52. 2-Amino-2-methyl-N-[2,3,4,5-tetrahydro-2-[[2'-[[ [(methylamino)carbonyl]amino]methyl][1,1'-biphenyl]-4-yl]methyl]- 3-oxo-1H-2-benzazepin-4(R)-yl]propanamide;

53. 2-Amino-2-methyl-N-[2,3,4,5-tetrahydro-2-[[2'-[[ [(methylamino)carbonyl]amino]methyl][1,1'-biphenyl]-4-yl]methyl]- 7-methylthio-3-oxo-1H-2-benzazepin-4(R)-yl]propanamide;

54. 2-Amino-2-methyl-N-[2,3,4,5-tetrahydro-2-[[2'-[[ [(methylamino)carbonyl]amino]methyl][1,1'-biphenyl]-4-yl]methyl]- 7-methoxy-3-oxo-1H-2-benzazepin-4(R)-yl]propanamide;

55. 2-Amino-2-methyl-N-[2,3,4,5-tetrahydro-2-[[2'-[[[(methylamino)carbonyl]amino]methyl][1,1'-biphenyl]-4-yl]methyl]-7-fluoro-3-oxo-1H-2-benzazepin-4(R)-yl]propanamide;

56. 3-Amino-3-methyl-N-[2,3,4,5-tetrahydro-2-[[2'-[[[(methylamino)carbonyl]amino]methyl][1,1'-biphenyl] 4-yl]methyl]- 3-oxo-1H-2-benzazepin-4(R)-yl]butanamide;

57. 3- Amino-3-methyl-N-[2,3,4,5-tetrahydro-2-[[2'-[[[(methylamino)carbonyl]amino]methyl][1,1'-biphenyl]-4-yl]methyl]- 7-methoxy-3-oxo-1H-2-benzazepin-4(R)-yl]butanamide;

58. 3-Amino-3-methyl-N-[ 2,3,4,5-tetrahydro-2-[[2'-[[[(methylamino)carbonyl]amino]methyl][1,1'-biphenyl]-4-yl]methyl]- 7-trifluoromethyl-3-oxo-1H-2-benzazepin-4(R)-yl]-butanamide;

59. 3-[2(R)-Hydroxypropyl]amino-3-methyl-N-[2,3,4,5-tetrahydro- 2-[[2'-[[[(methylamino)carbonyl]amino] methyl][ 1,1'-biphenyl]-4-yl]methyl]-3-oxo-1H-2-benzazepin-4(R)-yl]-butanamide;

60. 3 -[2(R)-Hydroxypropyl]amino-3-methyl-N-[2,3,4,5-tetrahydro- 2-[[2'-[[[(methylamino)carbonyl]amino] methyl][ 1,1'-biphenyl]-4-yl]methyl]-7-methylthio-3-oxo-1H-2-benzazepin- 4(R)-yl]butanamide;

61. 3-[2(R)-Hydroxypropyl]amino-3-methyl-N-[2,3,4,5-tetrahydro- 2-[[2'-[[[(methylamino)carbonyl]amino] methyl][ 1,1'-biphenyl]-4-yl]methyl]-7-fluoro-3-oxo-1H-2-benzazepin- 4(R)-yl]butanamide;

62. 3-[2(S),3-Dihydroxypropyl]amino-3-methyl-N-[2,3,4,5-tetrahydro- 2-[[2'-[[[(methylamino)carbonyl]amino]methyl]-[ 1,1'-biphenyl]-4-yl]methyl]-3-oxo-1H-2-benzazepin-4(R)-yl]butanamide;

63. 3-[2(S),3-Dihydroxypropyl]amino-3-methyl-N-[2,3,4,5-tetrahydro- 2-[[2'-[[[(methylamino)carbonyl]amino]methyl]-[ 1,1' -biphenyl]-4-yl]methyl]-7-methoxy-3-oxo-1H-2-benzazepin- 4(R)-yl]butanamide;

64. 3-[2(S),3-Dihydroxypropyl]amino-3-methyl-N-[2,3,4,5-tetrahydro- 2-[[2'-[[[(methylamino)carbonyl]amino]methyl]-[ 1,1'-biphenyl]-4-yl]methyl]-7-trifluoromethyl-3-oxo-1H-2-benzazepin- 4(R )-yl]butanamide;

65. 2-Amino-2-methyl-N-[2,3,4,5-tetrahydro-2-[[2'-[[(aminocarbonyl)amino]methyl] [1,1'-biphenyl]-4-yl] methyl]-3-oxo- 1H-2-benzazepin-4(R)-yl]propanamide;

66. 2-Amino-2-methyl-N-[ 2,3,4,5-tetrahydro-2-[ [ 2'-[ [ (aminocarbonyl)amino]methyl][1,1-biphenyl]-4-yl] methyl]-7-methylthio- 3-oxo-1H-2-benzazepin-4(R)-yl]propanamide;

67. 3-Amino-3-methyl-N-[2,3,4,5-tetrahydro-2-[[2'-[ [ (aminocarbonyl)amino]methyl] [ 1,1'-biphenyl]-4-yl] methyl]-3-oxo- 1H-2-benzazepin-4(R)-yl]butanamide;

68. 3-Amino-3-methyl-N-[2,3,4,5-tetrahydro-2-[ [ 2'-[ [(aminocarbonyl)amino ]methyl] [ 1,1'-biphenyl]-4-yl] methyl]-7-methylthio- 3-oxo-1H-2-benzazepin-4(R)-yl]butanamide;

69. 3-Amino-3-methyl-N-[2,3,4,5-tetrahydro-2-[[2'-[ [(aminocarbonyl)amino ]methyl][1,1'-biphenyl]-4-yl] methyl]-7-fluoro- 3-oxo-1H-2-benzazepin-4(R)-yl]butanamide;

70. 3-[2(R)-Hydroxypropyl]amino-3-methyl-N-[2,3,4,5-tetrahydro- 2-[[2'-[[[(aminocarbonyl)amino]methyl][ 1,1'-biphenyl]-4-yl]methyl]-3-oxo-1H-2-benzazepin-4(R)-yl]-butanamide;

71. 3-[2(R)-Hydroxypropyl]amino-3-methyl-N-[ 2,3,4,5-tetrahydro- 2-[[ 2'-[[ (aminocarbonyl)amino]methyl] [ 1,1'-biphenyl]-4-yl]methyl] -7-methylthio-3-oxo-1H-2-benzazepin- 4(R)-yl]butanamide;

72. 3-[2(R)-Hydroxypropyl]amino-3'- methyl-N-[2,3,4,5-tetrahydro- 2-[ [2'-[[ (aminocarbonyl)amino]methyl] [ 1,1'-biphenyl] -4- yl]methyl]-7-fluoro-3-oxo-1H-2-benzazepin- 4(R)-yl]butanamide;

73. 3-[2(S),3-Dihydroxypropyl]amino-3-methyl-N-[2,3,4,5-tetrahydro- 2-[[2'-[[(aminocarbonyl)amino]methyl][ 1,1'-biphenyl]-4-yl]methyl]-3-oxo-1H-2-benzazepin-4(R)-yl]-butanamide;

74. 3-[2(S),3-Dihydroxypropyl]amino-3-methyl-N-[2,3,4,5-tetrahydro- 2-[[2'-[[ (aminocarbonyl)amino]methyl] [ 1,1'-biphenyl]-4-yl]methyl]-7-methoxy-3-oxo-1H-2-benzazepin-(R)-yl]butanamide;

75. 3-[2(S),3-Dihydroxypropyl]amino-3-methyl-N-[2,3,4,5-tetrahydro- 2-[[ 2'-[[(aminocarbonyl)amino]methyl] [ 1,1'-biphenyl]-4-yl]methyl]-7-fluoro-3-oxo-1H-2-benzazepin-(R)-yl]butanamide;

76. 2-Amino-2-methyl-N-[2,3,4,5-tetrahydro-2-[[2'-[[[(ethylamino)carbonyl]amino]methyl][1,1'-biphenyl]-4-yl]methyl]-oxo- 1H-2-benzazepin-4(R)-yl]propanamide;

77. 2-Amino-2-methyl-N-[2,3,4,5-tetrahydro-2-[[2'-[[ [ (ethylamino)carbonyl]amino]methyl][1,1'-biphenyl]-4-yl]methyl]-7-methylthio-3-oxo-1H-2-benzazepin-4(R)-yl]propanamide;

78. 2-Amino-2-methyl-N-[2,3,4,5-tetrahydro-2-[[2'-[[[(ethylamino)carbonyl]amino]methyl][1,1'-biphenyl]-4-yl]methyl]- 7-fluoro-3-oxo-1H-2-benzazepin-4(R)-yl]propanamide;

79. 3-Amino-3-methyl-N-[2,3,4,5-tetrahydro-2-[[2'-[[[(ethylamino)carbonyl] amino]methyl][ 1,1-biphenyl]-4-yl]methyl]- 3-oxo-1H-2-benzazepin-4(R)-yl]butanamide;

80. 3-Amino-3-methyl-N-[2,3,4,5-tetrahydro-2-[[2'-[[[(ethylamino)carbonyl]amino]methyl][1,1'-biphenyl]-4-yl]methyl]- 7-methoxy-3-oxo-1H-2-benzazepin-4(R)-yl]butanamide;

81. 3-Amino-3-methyl-N-[2,3,4,5-tetrahydro-2-[[2'-[[[(ethylamino)carbonyl]amino]methyl][1,1'-biphenyl]-4-yl]methyl]- 7-fluoro-3-oxo-1H-2-benzazepin-4(R)-yl]butanamide;

82. 3-[2(R)-Hydroxypropyl]amino-3-methyl-N-[ 2,3,4,5-tetrahydro- 2-[[2'-[[[(ethylamino)carbonyl]amino]methyl][1,1'-biphenyl]-4-yl]methyl]-3-oxo-1H-2-benzazepin-4(R)-yl]-butanamide;

83. 3-[2(R)-Hydroxypropyl]amino-3-methyl-N-[2,3,4,5-tetrahydro- 2-[[2'-[[[(ethylamino)carbonyl]amino]methyl][1,1'-biphenyl]- 4-yl]methyl]-7-methylthio-3-oxo-1H-2-benzazepin-4(R)-yl]butanamide;

84. 3-[2(R)-Hydroxypropyl]amino-3-methyl-N-[2,3,4,5-tetrahydro- 2-[[2'-[[[(ethylamino)carbonyl]amino]methyl][1,1'-biphenyl]-4-yl]methyl]-7-methoxy-3-oxo-1H-2-benzazepin- 4(R)-yl]butanamide;

85. 3-[2(R)-Hydroxypropyl]amino-3-methyl-N-[2,3,4,5-tetrahydro- 2-[[2'-[[[(ethylamino)carbonyl]amino]methyl] [1,1'-biphenyl]-4-yl]methyl]-7-fluoro-3-oxo-1H-2-benzazepin- 4(R)-yl]butanamide;

86. 3-[2(S),3-Dihydroxypropyl]amino-3-methyl-N-[2,3,4,5-tetrahydro- 2-[[2'-[[[ (ethylamino)carbonyl]amino]methyl]-[ 1,1'-biphenyl]-4-yl]methyl]-3-oxo-1H-2-benzazepin-4(R)-yl]butanamide;

87. 3-[2(S),3-Dihydroxypropyl]amino-3-methyl-N-[2,3,4,5-tetrahydro- 2-[[2'-[[[(ethylamino)carbonyl]amino]methyl]-[ 1,1'-biphenyl]-4-yl]methyl]-7-methylthio-3-oxo-1H-2-benzazepin- 4(R)-yl]butanamide;

88. 3-[2(S),3-Dihydroxypropyl]amino-3-methyl-N-[2,3,4,5-tetrahydro- 2-[[2'-[[[(ethylamino)carbonyl]amino]methyl]-[ 1,1'-biphenyl]-4-yl]methyl]-7-methoxy-3-oxo-1H-2-benzazepin- 4(R)-yl]butanamide;

89. 3-[2(S),3-Dihydroxypropyl]amino-3-methyl-N-[2,3,4,5-tetrahydro- 2-[[2'-[[[(ethylamino)carbonyl]amino]methyl]-[ 1,1'-biphenyl]-4-yl]methyl]-7-fluoro-3-oxo-1H-2-benzazepin- 4(R)-yl]butanamide;

90. 2-Amino-2-methyl-N-[2,3,4,5-tetrahydro-2-[[2 '-[[[(2-hydroxyethyl)amino]carbonyl]amino]methyl][1,1'-biphenyl]-4-yl]methyl]-3-oxo-1H-2-benzazepin-4(R)-yl]-propanamide;

91. 2-Amino-2-methyl-N-[2,3,4,5-tetrahydro-2-[[2'-[[[(2-hydroxyethyl)amino]carbonyl]amino]methyl][1,1'-biphenyl]-4-yl]methyl]-7-methylthio-3-oxo-1H' 2-benzazepin- 4(R)-yl]propanamide;

92. 2-Amino-2-methyl-N-[2,3,4,5-tetrahydro-2-[ [2'-[[[(2-hydroxyethyl)amino]carbonyl]amino]methyl][1,1'-biphenyl]-4-yl]methyl]-7-methoxy-3-oxo-1H-2-benzazepin-4(R)-yl]propanamide;

93. 2- Amino-2-methyl-N-[ 2,3,4,5-tetrahydro-2-[[2'-[[ [ [ (2-hydroxyethyl)amino]carbonyl]amino]methyl][1,1'-biphenyl]-4-yl]methyl]-7-fluoro-3-oxo-1H-2-benzazepin-4(R)-yl]propanamide;

94. 3-Amino-3-methyl-N-[2,3,4,5-tetrahydro-2-[[2'-[[ [ [ (2-hydroxyethyl)amino]carbonyl]amino]methyl][1,1'-biphenyl]-4-yl]methyl]-3-oxo-1H-2-benzazepin-4(R)-yl]-butanamide;

95. 3-Amino-3-methyl-N-[2,3,4,5-tetrahydro-2-[[2'-[[[(2-hydroxyethyl)amino]carbonyl]amino]methyl][1,1'-biphenyl]-4-yl]methyl] -7-methylthio-3-oxo-1H-2-benzazepin- 4(R)-yl]butanamide; p1 96. 3-Amino-3-methyl-N-[2,3,4,5-tetrahydro-2-[[2'-[[[[(2-hydroxyethyl)amino]carbonyl]amino]methyl][1,1'-biphenyl]-4-yl]methyl]-7-methoxy-3-oxo-1H-2-benzazepin- 4(R)-yl]butanamide;

97. 3-Amino-3-methyl-N-[2,3,4,5-tetrahydro-2-[[2'-[[ [ [ (2-hydroxyethyl)amino]carbonyl]amino]methyl][1,1'-biphenyl]-4-yl]methyl]-7-fluoro-3-oxo-1H-2-benzazepin- 4(R)-yl]butanamide;

98. 3-[2(R)-Hydroxypropyl]amino-3-methyl-N-[2,3,4,5-tetrahydro- 2-[[2'- [[[[(2-hydroxyethyl)amino]carbonyl]amino]-methyl] [1,1'-biphenyl]-4-yl]methyl]-3-oxo-1H-2-benzazepin- 4(R)-yl]butanamide;

99. 3-[2(R)-Hydroxypropyl]amino-3-methyl-N-[2,3,4,5-tetrahydro- 2-[[2'-[[[[(2-hydroxyethyl)amino]carbonyl]amino]-methyl] [1,1'-biphenyl]-4-yl]methyl]-7-methylthio-3-oxo- 1H-2- benzazepin4(R)-yl]butanamide;

100. 3 -[2(R)-Hydroxypropyl]amino-3-methyl-N-[2,3,4,5-tetrahydro- 2-[[2'-[[[[(2-hydroxyethyl)amino]carbonyl]amino]-methyl] [1,1'-biphenyl]-4-yl]methyl]-7-methoxy-3-oxo-1H- 2-benzazepin-4(R)-yl]butanamide;

101. 3-[2(R)-Hydroxypropyl]amino-3-methyl-N-[ 2,3,4,5-tetrahydro- 2-[[2'-[[[[(2-hydroxyethyl)amino]carbonyl]amino]-methyl] [1,1'-biphenyl]-4-yl]methyl]-7-fluoro-3-oxo-1H-2-benzazepin- 4(R)-yl]butanamide;

102. 3-[2(S),3-Dihydroxypropyl]amino-3-methyl-N-[2,3,4,5-tetrahydro- 2-[[2'-[[[[(2-hydroxyethyl)amino]carbonyl]-amino]methyl][ 1,1'-biphenyl]-4-yl]methyl]-3-oxo-1H-2-benzazepin- 4(R)-yl]butanamide;

103. 3-[2(S),3-Dihydroxypropyl]amino-3-methyl-N-[2,3,4,5-tetrahydro- 2-[[2'-[[[[(2-hydroxyethyl)amino]carbonyl]-amino]methyl] [ 1,1'-biphenyl]-4-yl]methyl]-7-methylthio-3-oxo- 1H-2-benzazepin-4(R)-yl]butanamide;

104. 3-[2(S),3-Dihydroxypropyl]amino-3-methyl-N-[2,3,4,5-tetrahydro- 2-[[2'-[[[[(2-hydroxyethyl)amino]carbonyl]-amino]methyl][1,1'-biphenyl]-4-yl]methyl]-7-methoxy-3-oxo- 1H-2-benzazepin-4(R)-yl]butanamide;

105. 3-[2(S),3-Dihydroxypropyl]amino-3-methyl-N-[2,3,4,5-tetrahydro- 2-[[2'-[[[[(2-hydroxyethyl)amino]carbonyl]-amino]methyl][ 1,1'-biphenyl]-4-yl]methyl]-7-fluoro-3-oxo- 1H-2-benzazepin4(R)-yl]butanamide;

106. 2-Amino-2-methyl-N-[ 2,3,4,5-tetrahydro-2-[[(methylamino)carbonyl]aminoprop-2-yl][1,1'-biphenyl]4-yl]-methyl] -3-oxo-1H-2-benzazepin-4(R)-yl]propanamide;

107. 2-Amino-2-methyl-N-[2,3,4,5-tetrahydro-2-[[2'-[1-[(methylamino)carbonyl]amino]ethyl][1,1'-biphenyl]-4-yl]-methyl] -3-oxo-1H-2-benzazepin-4(R)-yl]propanamide;

108. 2-Amino-2-methyl-N-[2,3,4,5-tetrahydro-2-[[2'-[ [(methoxycarbonyl)amino]methyl][1,1'-biphenyl]-4-yl]-methyl] -3-oxo-1H-2-benzazepin-4(R)-yl]propanamide;

109. 3-Amino-3-methyl-N-[2,3,4,5-tetrahydro-2-[[2'-[ [(methoxycarbonyl)amino]methyl] [1,1'-biphenyl]-4-yl]-methyl]-3-oxo-1H-2-benzazepin-4(R)-yl]butanamide;

110. 3-[2(R)-Hydroxypropyl]amino-3-methyl-N-[2,3,4,5-tetrahydro- 2-[[2'-[[(methoxycarbonyl)amino]methyl] [1,1'-biphenyl]-4-yl]methyl]-3-oxo-1H-2-benzazepin- 4(R)-yl]-butanamide;

111. 3-[2(S),3-Dihydroxypropyl]amino-3-methyl-N-[2,3,4,5-tetrahydro- 2-[[2'-[[(methoxycarbonyl)amino]methyl] [1,1'-biphenyl]-4-yl]methyl]-3-oxo-1H-2-benzazepin-4(R)-yl]-butanamide;

112. 2-Amino-2-methyl-N-[2,3,4,5-tetrahydro-3-oxo-4-[ [2'-(1H-tetrazol- 5-yl)[1,1'-biphenyl]-4-yl]methyl]-1,4-benzothiazepin- 2 (R)- yl]propanamide;

113. 3-Amino-3-methyl-N-[2,3,4,5-tetrahydro-3-oxo-4-[[ 2'-(1H-tetrazol- 5-yl)[1,1'-biphenyl]-4-yl]methyl]-1,4-benzothiazepin- 2(R)-yl]butanamide;

114. 3-[2(R)-Hydroxypropyl]amino-3-methyl-N-[ 2,3,4, 5-tetro-hydro- 3-oxo-4-[[2'-(1H-tetrazol-5-yl)[1,1'-biphenyl]-4-yl]-methyl] -1,4-benzothiazepin-2(R)-yl]butanamide;

115. 3-[2(S),3-Dihydroxypropyl]amino-3-methyl-N-[2,3,4,5-tetrahydro- 3-oxo-4-[[2'-(1H-tetrazol-5-yl)[1,1'-biphenyl]-4-yl]methyl]-1,4-benzothiazepin-2(R)-yl]butanamide;

116. 3-[2(R)-Hydroxypropyl]amino-3-methyl-N-[2,3,4,5-tetrahydro- 8-methoxy-3-oxo-4-[[2'-(1H-tetrazol-5-yl) [1,1'-biphenyl] -4-yl]methyl]-1,4-benzothiazepin-2(R)-yl]-butanamide;

117. 3 -[2(S),3-Dihydroxypropyl]amino-3-methyl -N-[ 2,3,4,5-tetrahydro- 8-methoxy-3-oxo-4-[[2'-(1H-tetrazol-5-yl)[ 1,1'-biphenyl]-4-yl]methyl]-1,4-benzothiazepin-2(R)-yl]-butanamide;

118. 2-Amino-2-methyl-N-[2,3,4,5-tetrahydro-8-fluoro-3-oxo- 4-[[2'-(1H-tetrazol-5-yl)[1,1'-biphenyl]-4-yl]methyl]-1,4-benzothiazepin- 2(R)-yl]propanamide;

119. 3-[2(S),3-Dihydroxypropyl]amino-3-methyl-N-[2,3,4,5-tetrahydro- 8-fluoro-3-oxo-4-[[2'-(1H-tetrazol-5- yl)[ 1,1'-biphenyl] -4-yl]methyl]-1,4-benzothiazepin-2(R)-yl]-butanamide;

120. 3-Amino-3-methyl-N-[2,3,4,5-tetrahydro-8-methylthio-3-oxo- 4-[[2'-(1H-tetrazol-5-yl)[ 1,1'-biphenyl]-4-yl]methyl]- 1,4-benzothiazepin-2(R)-yl]butanamide;

121. 3-[2(R)-Hydroxypropyl]amino -3-methyl-N-[2,3,4,5-tetrahydro- 8-methylthio-3-oxo-4-[[2'-(1H-tetrazol-5-yl)[1,1'-biphenyl]4-yl]methyl]-1,4-benzothiazepin-2(R)-yl]-butanamide;

122. N-Ethyl4'-[[2(R)-[(2-amino-2-methyl-1-oxopropyl)-amino]-2,3,4,5-tetrahydro-3-oxo-1,4-benzothiazepin-4-yl]-methyl][1,1'-biphenyl]-2-carboxamide;

123. N-Ethyl-4'-[[2(R)-[[[[2(S),3-dihydroxypropyl]amino]-3-methyl- 1-oxobutyl)amino]-2,3,4,5-tetrahydro-3-oxo-1,4-benzothiazepin- 4-yl]methyl][1,1'-biphenyl]-2-carboxamide;

124. N-Ethyl-4'-[[2(R)-[[ [ 2(R)-hydroxypropyl]amino] -3-methyl- 1-oxobutyl]amino]-2,3,4,5-tetrahydro-8-fluoro-3-oxo- 1,4-benzothiazepin-4-yl]methyl][1,1'-biphenyl]-2-carboxamide;

125. N-Ethyl-4'-[[2(R)-[[[[2(S),3-dihydroxypropyl]amino]-3-methyl- 1-oxobutyl)amino]-2,3,4,5-tetrahydro-8-fluoro-3-oxo- 1,4-benzothiazepin-4-yl]methyl][1,1'-biphenyl]-2-carboxamide;

126. N-Ethyl-4'-[[2(R)-[(2-amino-2-methyl-1-oxopropyl)-amino]-2,3,4,5-tetrahydro-8-methoxy-3-oxo-1,4-benzothiazepin- 4-yl]methyl] [1,1'-biphenyl]-2-carboxamide;

127. N-Ethyl-4'-[[ 2(R)-[[[[2(S),3-dihydroxypropyl] amino]-3-methyl- 1-oxobutyl)amino]-2,3,4,5-tetrahydro-8-methoxy- 3-oxo-1,4-benzothiazepin-4-yl]methyl][1,1'-biphenyl1-2-carboxamide;

128. N-Ethyl-4'-[[ 2(R)-[(2-amino-2-methyl-1-oxopropyl)-amino]-2,3,4,5-tetrahydro-8-methylthio-3-oxo-1, 4-benzothiazepin- 4-yl]methyl][1,1'-biphenyl]-2-carboxamide;

129. N-Ethyl-4'-[[2(R)-[[[[2(R)-hydroxypropyl]amino]-3-methyl- 1-oxobutyl]amino]-2,3,4,5-tetrahydro-8-methylthio-3 -oxo-1,4-benzothiazepin-4-yl]methyl][1,1'-biphenyl]-2-carboxamide;

130. N-Ethyl-4'-[[2(R)-[[[[2(S),3-dihydroxypropyl]amino]-3-methyl- 1-oxobutyl]amino]-2,3,4,5-tetrahydro-8-methylthio- 3-oxo- 1,4-benzothiazepin-4-yl]methyl][1,1'-biphenyl]-2-carboxamide;

131. 2-Amino-2-methyl-N-[2,3,4,5-tetrahydro-3-oxo-4-[ [2'-hydroxymethyl[ 1,1'-biphenyl]-4-yl]methyl]-1,4-benzothiazepin- 2(R)-yl]propanamide;

132. 3-[2(S),3-Dihydroxypropyl]amino-3-methyl-N-[2,3, 4,5-tetrahydro- 3-oxo-4-[[2 '-hydroxymethyl[ 1,1'-biphenyl]-4-yl] methyl]-1,4-benzothiazepin-2(R)- yl]butanamide;

133. 3-Amino-3-methyl-N-[2,3,4,5-tetrahydro-8-methylthio-3-oxo- 4-[[2 '-hydroxymethyl[1,1'-biphenyl]-4-yl]methyl]-1,4-benzothiazepin- 2(R)-yl]butanamide;

134. 3-[2(R)-Hydroxypropyl]amino-3-methyl-N-[2,3,4, 5-tetrahydro- 8-trifluoromethyl-3-oxo-4-[[2'-hydroxymethyl[1,1'-biphenyl]-4-yl]methyl]-1,4-benzothiazepin-2(R)-yl]-butanamide;

135. 3-Amino-3-methyl-N-[2,3,4,5-tetrahydro-4-[[2'-[ [(methylamino)carbonyl]amino][ 1,1'-biphenyl]-4-yl] methyl]-3-oxo- 1,4-benzothiazepin-2(R)-yl]butanamide;

136. 3-[2(R)-Hydroxypropyl]amino-3-methyl-N-[2,3,4, 5-tetrahydro- 4-[[2'-[[(methylamino)carbonyl]amino][ 1,1'-biphenyl] -4-yl] methyl] -3-oxo-1,4-benzothiazepin-2(R)-yl] -butanamide;

137. 3-[2(S),3-Dihydroxypropyl]amino-3-methyl-N-[2,3, 4,5-tetrahydro- 4-[[2'-[[(methylamino)carbonyl] amino][1,1'-biphenyl]-4-yl]methyl]-3-oxo-1,4-benzothiazepin-2(R)-yl]-butanamide;

138. 3-Amino-3-methyl-N-[2,3,4,5-tetrahydro-8-methylthio-4-[[2'-[[(methylamino)carbonyl]amino][1,1'-biphenyl]-4-yl]-methyl] -3-oxo-1,4-benzothiazepin-2(R)-yl]butanamide;

139. 3-[2(R)-Hydroxypropyl]amino-3-methyl-N-[ 2,3,4, 5-tetrahydro- 8-methylthio-4-[[2'-[[(methylamino)carbonyl]-amino][1,1'-biphenyl]-4-yl]methyl]-3-oxo-1,4-benzothiazepin- 2(R)-yl]butanamide;

140. 3-[2(S),3-Dihydroxypropyl]amino-3-methyl-N-[2,3, 4,5-tetrahydro- 8-methylthio-4-[[2'-[[(methylamino)carbonyl]-amino][1,1'-biphenyl]-4-yl]methyl]-3-oxo-1,4-benzothiazepin- 2(R)-yl]butanamide;

141. 3-Amino-3-methyl-N-[2,3,4,5-tetrahydro-8-methoxy-4-[[2'-[[(methylamino)carbonyl]amino][1,1'-biphenyl]-4-yl]-methyl] -3-oxo-1,4-benzothiazepin-2(R)-yl]butanamide;

142. 3-[2(R)-Hydroxypropyl]amino-3-methyl-N-[ 2,3,4, 5-tetrahydro- 8-methoxy-4-[[2'-[[(methylamino)carbonyl]amino]-[ 1,1'-biphenyl]-4-yl]methyl]-3-oxo-1,4-benzothiazepin- 2(R)-yl]butanamide;

143. 3-[2(S),3-Dihydroxypropyl]amino-3-methyl-N-[2,3, 4,5-tetrahydro- 8-methoxy4-[[2'-[[(methylamino)carbonyl]-amino][1,1'-biphenyl]-4-yl]methyl]-3-oxo-1,4-benzothiazepin- 2(R)-yl]butanamide;

144. 3-Amino-3-methyl-N-[ 2,3,4,5-tetrahydro-8-fluoro-4-[[ 2'-[[(methylamino)carbonyl]amino][ 1,1'-biphenyl]-4-yl]-methyl]-3-oxo-1,4-benzothiazepin-2(R)-yl] butanamide;

145. 3-[2(R)-Hydroxypropyl]amino-3-methyl-N-[2,3,4, 5-tetrahydro- 8-fluoro-4-[[2' -[[(methylamino)carbonyl]-amino][1,1'-biphenyl]-4-yl]methyl]-3-oxo-1,4-benzothiazepin- 2(R)-yl]butanamide;

146. 3-[2(S),3-Dihydroxypropyl]amino-3-methyl-N-[2,3, 4,5-tetrahydro- 8-fluoro-4-[[2 '-[[(methylamino)carbonyl]-amino][ 1,1'-biphenyl]-4-yl]methyl]-3-oxo-1,4-benzothiazepin- 2(R )-yl]butanamide;

147. 2-Amino-2-methyl-N-[ 2,3,4,5-tetrahydro-4-[[2'-[ (morpholinocarbonyl)amino][1,1'-biphenyl]-4-yl]methyl]- 3-oxo-1,4-benzothiazepin-2(R)-yl]propanamide;

148. 3-Amino-3-methyl-N-[ 2,3,4,5-tetrahydro-4-[[2'-[ (morpholinocarbonyl)amino] [ 1,1'-biphenyl]-4-yl]methyl]- 3-oxo-1,4-benzothiazepin-2(R)-yl]butanamide;

149. 3-[2(R)-Hydroxypropyl]amino-3-methyl-N-[2,3,4, 5-tetrahydro- 4-[[2'-[(morpholinocarbonyl)amino][1, 1'-biphenyl]- 4-yl]methyl]-3-oxo-1,4-benzothiazepin-2(R)-yl]butanamide;

150. 3-[2(S),3-Dihydroxypropyl]amino-3-methyl-N-[2,3, 4,5-tetrahydro- 4-[[2'-[(morpholinocarbonyl)amino][1, 1'-biphenyl]-4-yl]methyl]-3-oxo-1,4-benzothiazepin-2(R)-yl]-butanamide;

151. 3-[2(R)-Hydroxypropyl]amino-3 -methyl-N-[2,3,4, 5-tetrahydro- 8-methylthio-4-[[2'-[(morpholinocarbonyl)-amino][1,1'-biphenyl]-4-yl]methyl]-3-oxo-1,4-benzothiazepin- 2(R)-yl]butanamide;

152. 3-[2(S),3-Dihydroxypropyl]amino-3-methyl-N-[2,3, 4,5-tetrahydro- 8-methylthio-4-[[2'-[(morpholinocarbonyl)-amino][1,1'-biphenyl]-4-yl]methyl]-3-oxo-1,4-benzothiazepin- 2(R)-yl]butanamide;

153. 3-Amino-3-methyl-N-[ 2,3,4,5-tetrahydro-8-methoxy-4-[[2'-[(morpholinocarbonyl)amino] [ 1,1'-biphenyl]-4-yl]-methyl] -3-oxo-1,4-benzothiazepin-2(R)-yl]butanamide;

154. 3-[2(R)-Hydroxypropyl]amino-3-methyl-N-[2,3,4,5-tetrahydro- 8-methoxy-4-[[2'-[(morpholinocarbonyl)-amino][1,1'-biphenyl]-4-yl]methyl]-3-oxo-1,4-benzothiazepin- 2(R)-yl]butanamide;

155. 3-[2(S),3-Dihydroxypropyl]amino-3-methyl-N-[2,3,4,5-tetrahydro- 8-methoxy-4-[[2'-[(morpholinocarbonyl)-amino][1,1'-biphenyl]-4-yl]methyl]-3-oxo-1,4-benzothiazepin- 2(R)-yl]butanamide;

156. 3-Amino-3-methyl-N-[ 2,3,4,5-tetrahydro-8-fluoro-4-[[ 2'-[ (morpholinocarbonyl)amino][1,1'-biphenyl]-4-yl]methyl]- 3-oxo-1,4-benzothiazepin-2(R)-yl]butanamide;

157. 3-[2(R)-Hydroxypropyl]amino-3-methyl-N-[2,3,4,5-tetrahydro- 8-fluoro-4-[[2'-[(morpholinocarbonyl)amino][ 1,1'-biphenyl]-4-yl]methyl]-3-oxo-1,4-benzothiazepin-2(R)-yl]-butanamide;

158. 3-[2(S),3-Dihydroxypropyl]amino-3-methyl-N-[2,3,4,5-tetrahydro- 8-fluoro-4-[[2'-[(morpholinocarbonyl)amino]-[ 1,1 '-biphenyl]-4-yl]methyl]-3-oxo-1,4-benzothiazepin- 2(R)-yl]butanamide;

159. 2-Amino-2-methyl-N-[ 2,3,4,5-tetrahydro-4-[[2'-[ [(2-hydroxyethylamino)carbonyl]amino][ 1,1'-biphenyl]-4-yl]-methyl]-3-oxo-1,4-benzothiazepin-2(R)-yl]propanamide;

160. 3-Amino-3-methyl-N-[2,3,4,5-tetrahydro-4-[[2'-[ [(2-hydroxyethylamino)carbonyl]amino][1,1'-biphenyl]-4-yl]-methyl]-3-oxo-1,4-benzothiazepin-2(R)-yl]butanamide;

161. 3-[2(R)-Hydroxypropyl]amino-3-methyl-N-[2,3,4,5-tetrahydro- 4-[[2'-[[(2-hydroxyethylamino)carbonyl] amino][ 1,1'-biphenyl]-4-yl]methyl]-3-oxo-1,4-benzothiazepin-2(R)-yl]-butanamide;

162. 3-[2(S),3-Dihydroxypropyl]amino-3-methyl-N-[2,3,4,5-tetrahydro- 4-[[2'-[[(2-hydroxyethylamino)carbonyl] -amino][1,1'-biphenyl]-4-yl]methyl]-3-oxo-1,4-benzothiazepin- 2(R)-yl]butanamide;

163. 3-Amino-3-methyl-N-[2,3,4,5-tetrahydro-8-methylthio-4-[[2'-[[(2-hydroxyethylamino)carbonyl]amino] [1,1'-biphenyl]-4-yl]methyl]-3-oxo-1,4-benzothiazepin-2(R)-yl]-butanamide;

164. 3-[2(R)-Hydroxypropyl]amino-3-methyl-N-[2,3,4,5-tetrahydro- 8-methylthio-4-[[2'-[[(2-hydroxyethylamino)-carbonyl]amino][1,1'-biphenyl]-4-yl]methyl]-3-oxo-1,4-benzothiazepin- 2(R)-yl]butanamide;

165. 3-[2(S),3-Dihydroxypropyl]amino-3-methyl-N-[2,3,4,5-tetrahydro- 8-methylthio-4-[[ 2 '-[[(2-hydroxyethylamino)-carbonyl]amino][1,1' -biphenyl]-4-yl]methyl]-3-oxo-1,4-benzothiazepin- 2(R)-yl]butanamide;

166. 3-Amino-3-methyl-N-[2,3,4,5-tetrahydro-8-methoxy24-[[2'-[[(2-hydroxyethylamino)carbonyl]amino] [1,1'-biphenyl]-4-yl]methyl]-3-oxo-1,4-benzothiazepin-2(R)-yl]-butanamide;

167. 3-[2(R)-Hydroxypropyl]amino-3-methyl-N-[2,3,4,5-tetrahydro- 8-methoxy-4-[[2'-[[ (2-hydroxyethylamino)-carbonyl]amino][ 1,1'-biphenyl]-4-yl]methyl]-3-oxo-1'4-benzothiazepin- 2(R)-yl]butanamide; pl 168. 3-[2(S),3-Dihydroxypropyl]amino-3-methyl-N-[ 2,3,4,5-tetrahydro- 8-methoxy-4-[[2'-[[(2-hydroxyethylamino)-carbonyl] amino] [ 1,1'-biphenyl] -4-yl]methyl]-3-oxo-1,4-benzothiazepin-2(R)-yl]butanamide;

169. 3-Amino-3-methyl-N-[2,3,4,5-tetrahydro-8-fluoro-4-[[2'-[[(2-hydroxyethylamino)carbonyl]amino][1,1'-biphenyl]-4-yl]methyl]-3-oxo-1,4-benzothiazepin-2(R)-yl]butanamide;

170. 3-[2(R)-Hydroxypropyl]amino-3-methyl-N-[ 2,3,4, 5-tetrahydro- 8-fluoro-4-[[2'-[[(2-hydroxyethylamino)carbonyl]amino][1,1'-biphenyl]-4-yl]methyl]-3-oxo-1,4-benzothi-azepin- 2(R)-yl]butanamide;

171. 3-[2(S),3-Dihydroxypropyl]amino-3-methyl-N-[2,3,4,5-tetrahydro- 8-fluoro-4-[[2'-[[ (2-hydroxyethylamino)-carbonyl]amino][1,1'-biphenyl]-4-yl]methyl]-3-oxo-1,4-benzothiazepin- 2(R)-yl]butanamide;

172. 2-Amino-2-methyl-N-[2,3,4,5-tetrahydro-4-[[2'-[[ [(methylamino)carbonyl]amino]methyl][ 1,1'-biphenyl]-4-yl]methyl]- 3-oxo-1,4-benzothiazepin-2(R)-yl]propanamide;

173. 3-Amino-3-methyl-N-[ 2,3,4,5-tetrahydro-4-[[2'-[[ [(methylamino)carbonyl]amino]methyl] [1,1'-biphenyl]-4-yl]methyl]- 3-oxo-1,4-benzothiazepin-2(R)-yl]butanamide;

174. 3-[2(S),3-Dihydroxypropyl]amino-3-methyl-N-[2,3,4,5-tetrahydro- 4-[[2'-[[[(methylamino)carbonyl]amino]-methyl] [1,1'-biphenyl]-4-yl]methyl]-3-oxo-1, 4-benzothiazepin- 2(R)-yl]butanamide;

175. 3-[2(R)-Hydroxypropyl]amino-3-methyl-N-[2,3,4,5-tetrahydro- 4-[[2'-[[[(methylamino)carbonyl]amino] methyl] [ 1,1'-biphenyl]-4-yl]methyl]-3-oxo-1,4-benzothiazepin-2(R)-yl]-butanamide;

176. 2-Amino-2-methyl-N-[2,3,4,5-tetrahydro-8-fluoro-4-[ [ 2'-[[[(methylamino)carbonyl]amino]methyl][1,1'-biphenyl]-4-yl]methyl]-3-oxo-1,4-benzothiazepin-2(R )-yl]propanamide;

177. 3-Amino-3-methyl-N-[2,3,4,5-tetrahydro-8-fluoro-4-[[2'-[[[(methylamino)carbonyl]amino]methyl] [1,1'-biphenyl]-4-yl]methyl]-3-oxo- 1,4-benzothiazepin-2(R)-yl]butanamide;

178. 3-[2(S),3-Dihydroxypropyl]amino-3-methyl-N-[2,3,4,5-tetrahydro- 8-fluoro-4-[[2'-[[[(methylamino)carbonyl]-amino]methyl] [ 1,1'-biphenyl]-4-yl]methyl]-3-oxo-1,4-benzothiazepin- 2(R)-yl]butanamide;

179. 3-[2(R)-Hydroxypropyl]amino-3-methyl-N-[ 2,3,4, 5-tetrahydro- 8-fluoro-4-[[2'-[[[(methylamino)carbonyl]amino1-methyl] [1,1'-biphenyl]4-yl]methyl] -3-oxo-1,4-benzothiazepin- 2(R)-yl]butanamide;

180. 2-Amino-2-methyl-N-[ 2,3,4,5-tetrahydro-8-methoxy-4-[[2'-[[[(methylamino)carbonyl]amino]methyl][ 1,1'-biphenyl]-4-yl]methyl]-3-oxo-1,4-benzothiazepin-2(R)-yl]-propanamide;

181. 3-[2(R)-Hydroxypropyl]amino-3-methyl-N-[ 2,3,4, 5-tetrahydro- 8-methoxy-4-[[2'-[[[(methylamino)carbonyl]amino]-methyl] [1,1'-biphenyl]4-yl]methyl]-3-oxo-1,4-benzothiazepin- 2(R)-yl]butanamide;

182. 2-Amino-2-methyl-N-[2,3,4,5-tetrahydro-8-methylthio-4-[[2'-[[[(methylamino)carbonyl]amino]methyl] [1,1'-biphenyl]-4-yl]methyl]-3-oxo-1,4-benzothiazepin-2(R)-yl]-propanamide;

183. 3-Amino-3-methyl-N-[2,3,4,5-tetrahydro-8-methylthio-4-[[2'-[[[ (methylamino)carbonyl]amino]methyl] [1,1'-biphenyl]-4-yl]methyl]-3-oxo-1,4-benzothiazepin-2(R)-yl]-butanamide;

184. 3-[ 2(R)-Hydroxypropyl]amino-3-methyl-N-[ 2,3,4, 5-tetrahydro- 8-methylthio-4-[[2'-[[[ (methylamino)carbonyl]-amino]methyl] [1,1'-biphenyl]-4-yl]methyl]-3-oxo-1,4-benzothiazepin- 2(R)-yl]butanamide;

185. 2-Amino-2-methyl-N-[2,3,4,5-tetrahydro-4-[[2'-[[(aminocarbonyl)amino]methyl] [ 1,1'-biphenyl]-4-yl]methyl]-3-oxo- 1,4-benzothiazepin-2(R)-yl]propanamide;

186. 3-[2(S),3-Dihydroxypropyl]amino-3-methyl-N-[ 2,3,4,5-tetrahydro 4-[[2'-[[(aminocarbonyl)amino]methyl][1,1'-biphenyl]-4-yl]methyl]-3-oxo-1,4-benzothiazepin-2(R)-yl]-butanamide;

187. 3-[2(R)-Hydroxypropyl]amino-3-methyl-N-[ 2,3,4, 5-tetrahydro- 4-[[ 2'-[[(aminocarbonyl)amino]methyl] [1,1'-biphenyl]-4-yl]methyl]-3-oxo-1,4-benzothiazepin-2(R)-yl]-butanamide;

188. 2-Amino-2-methyl-N-[2,3,4,5-tetrahydro-8-fluoro-4-[ [ 2'-[[ (aminocarbonyl)amino]methyl] [ 1,1'-biphenyl] -4-yl] -methyl] -3-oxo-1,4-benzothiazepin-2(R)-yl]propanamide;

189. 3-[ 2(S),3-Dihydroxypropyl]amino-3-methyl-N-[2, 3,4,5-tetrahydro- 8-fluoro-4-[[ 2'-[[(aminocarbonyl)amino]-methyl][1,1'-biphenyl]-4-yl]methyl]-3-oxo-1, 4-benzothiazepin- 2(R)-yl]butanamide;

190. 2-Amino-2-methyl-N-[ 2,3,4,5-tetrahydro-8-methoxy-4-[[2'-[[(aminocarbonyl)amino]methyl][ 1,1'-biphenyl]-4-yl]-methyl]-3-oxo-1,4-benzothiazepin-2(R)-yl]propanamide;

191. 3-Amino-3-methyl-N-[2,3,4,5-tetrahydro-8-methoxy-4-[[2'-[[(aminocarbonyl)amino]methyl] [ 1,1'-biphenyl]-4-yl]-methyl]-3-oxo-1,4-benzothiazepin-2(R)-yl]butanamide;

192. 3-[2(S),3-Dihydroxypropyl]amino-3-methyl-N-[2,3, 4,5-tetrahydro- 8-methylthio-4-[[ 2'-[[(aminocarbonyl)amino]-methyl][1,1'-biphenyl]-4-yl]methyl]-3-oxo-1, 4-benzothiazepin- 2(R)-yl]butanamide;

193. 3-[2(R)-Hydroxypropyl]amino-3-methyl-N-[ 2,3,4, 5-tetrahydro- 8-methylthio-4-[[2'-[[(aminocarbonyl)amino 1-methyl] [1,1'-biphenyl] -4-yl]methyl]-3-oxo- 1,4-benzothiazepin- 2(R)-yl]butanamide;

194. 2-Amino-2-methyl-N-[2,3,4,5-tetrahydro-4-[[2'-[[ [(ethylamino)carbonyl]amino]methyl][ 1,1'-biphenyl]-4-yl]methyl]- 3-oxo-1,4-benzothiazepin-2(R)-yl]propanamide;

195. 3-[2(S),3-Dihydroxypropyl]amino-3-methyl-N-[2,3, 4,5-tetrahydro- 4-[[2'-[ [[ (ethylamino)carbonyl]amino]methyl]-[1,1'-biphenyl]-4-yl]methyl]-3-oxo-1,4-benzothiazepin- 2(R)-yl]butanamide;

196. 3-[2(R)-Hydroxypropyl]amino-3-methyl-N-[ 2,3,4, 5-tetrahydro 4-[[2'-[[[(ethylamino)carbonyl]amino] methyl][ 1,1'-biphenyl]-4-yl]methyl]-3-oxo-1,4-benzothiazepin-2(R)-yl]-butanamide;

197. 2- Amino-2-methyl-N-[2,3,4,5-tetrahydro-8-fluoro-4-[[2'-[[[ (ethylamino)carbonyl]amino]methyl][ 1,1'-biphenyl]-4-yl]-methyl] -3-oxo-1,4-benzothiazepin-2(R)-yl]propanamide;

198. 3-[2(S),3-Dihydroxypropyl]amino-3-methyl-N-[2,3, 4,5-tetrahydro- 8-fluoro-4-[[2'-[[[(ethylamino)carbonyl]amino]-methyl][1,1'-biphenyl]-4-yl]methyl]-3-oxo-1,4-benzothiazepin- 2(R)-yl]butanamide;

199. 2-Amino-2-methyl-N-[2,3,4,5-tetrahydro-8-methoxy-4-[[2'-[[[(ethylamino)carbonyl]amino]methyl][1, 1'-biphenyl]- 4-yl]methyl]-3-oxo-1,4-benzothiazepin-2(R)-yl]-propanamide;

200. 3-[2(S),3-Dihydroxypropyl]amino-3-methyl-N-[2,3, 4,5-tetrahydro- 8-methoxy-4-[[2'-[[[(ethylamino)carbonyl] -amino]methyl][ 1,1'-biphenyl]-4-yl]methyl]-3-oxo-1,4-benzothiazepin- 2(R)- yl]butanamide;

201. 3-Amino-3-methyl-N-[2,3,4,5-tetrahydro-8-methylthio-4-[[2' -[[[(ethylamino)carbonyl]amino]methyl][ 1,1'-biphenyl]- 4-yl]methyl]-3-oxo-1,4-benzothiazepin-2(R)-yl]butanamide;

202. 3-[2(S),3-Dihydroxypropyl]amino-3-methyl-N-[2,3, 4,5-tetrahydro- 8-methylthio-4-[[2'-[[[(ethylamino)carbonyl]-amino] methyl][1,1'-biphenyl]-4-yl]methyl]-3-oxo-1,4-benzothiazepin- 2(R)-yl]butanamide;

203. 2-Amino-2-methyl-N-[2,3,4,5-tetrahydro-4-[[2'-[[ [[(2-hydroxyethyl)amino]carbonyl]amino]methyl][1, 1'-biphenyl]-4-yl]methyl]-3-oxo-1,4-benzothiazepin-2(R)-yl]-propanamide;

204. 3-Amino-3-methyl-N-[2,3,4,5-tetrahydro-4-[[2'-[[ [ [(2-hydroxyethyl)amino]carbonyl]amino]methyl][1,1'-biphenyl]-4-yl]methyl]-3-oxo-1,4-benzothiazepin- 2(R)-yl]-butanamide;

205. 3-[2(S),3-Dihydroxypropyl]amino-3-methyl-N-[2,3, 4,5-tetrahydro- 4-[[2'-[[[[(2-hydroxyethyl)amino]carbonyl]-amino]methyl] [1,1'-biphenyl]-4-yl]methyl]-3-oxo-1,4-benzothiazepin- 2(R)-yl]butanamide;

206. 3-[2(R)-Hydroxypropyl]amino-3-methyl-N-[2,3,4, 5-tetrahydro- 4-[[2'-[[[[(2-hydroxyethyl)amino]carbonyl]amino]-methyl][1,1'-biphenyl]-4-yl]methyl]-3-oxo-1,4-benzothiazepin- 2(R)-yl]butanamide;

207. 2-Amino-2-methyl-N-[2,3,4,5-tetrahydro-8-fluoro-4-[ [ 2'-[[[[(2-hydroxyethyl)amino]carbonyl]amino] methyl][ 1,1'-biphenyl]-4-yl]methyl]-3-oxo-1,4-benzothiazepin-2(R)-yl]-propanamide;

208. 3-[ 2(S),3-Dihydroxypropyl]amino-3-methyl-N-[2, 3,4,5-tetrahydro- 8-fluoro-4-[[2'-[[[[(2-hydroxyethyl)amino]-carbonyl]amino]methyl][ 1,1'-biphenyl]-4-yl]methyl]-3-oxo- 1,4-benzothiazepin-2(R)-yl]butanamide;

209. 2-Amino-2-methyl-N-[ 2,3,4,5-tetrahydro-8-methoxy-4-[[ 2'-[[[[(2-hydroxyethyl)amino]carbonyl] amino]methyl]-[1,1'-biphenyl]-4-yl]methyl]-3-oxo-1, 4-benzothiazepin- 2(R)-yl]propanamide;

210. 3-[2(R)-Hydroxypropyl]amino-3-methyl-N-[ 2,3,4, 5-tetrahydro- 8-methoxy-4-[[2 '-[[[ (2-hydroxyethyl))-amino]-carbonyl]amino]methyl][1,1'-biphenyl]-4-yl]methyl]-3-oxo- 1,4-benzothiazepin-2(R)-yl]butanamide;

211. 3-[2(S),3-Dihydroxypropyl]amino-3-methyl-N-[2,3, 4,5-tetrahydro- 8-methylthio-4-[[2'-[[[[(2-hydroxyethyl)-amino]-carbonyl]amino]methyl][1,1'-biphenyl]-4-yl]methyl]-3-oxo- 1,4-benzothiazepin-2(R)-yl]butanamide;

212. 3-[2(R)-Hydroxypropyl]amino-3-methyl-N-[ 2,3,4, 5-tetrahydro- 8-methylthio-4-[[2'-[[[[(2-hydroxyethyl)amino]-carbonyl]amino]methyl][ 1,1'-biphenyl]-4-yl]methyl]-3-oxo- 1,4-benzothiazepin-2(R)-yl]butanamide;

213. 2-Amino-2-methyl-N-[2,3,4,5-tetrahydro-4-[[2'-[ 2-[[ (methylamino)carbonyl]amino]prop-2-yl][ 1,1'-biphenyl]- 4-yl]methyl]-3-oxo-1,4-benzothiazepin-2(R)-yl]propanamide;

214. 2-Amino-2-methyl-N-[2,3,4,5-tetrahydro-4-[[2'-[1-[ [(methylamino)carbonyl]amino]ethyl][1,1'-biphenyl]- 4-yl]-methyl]-3-oxo-1,4-benzothiazepin-2(R)-yl]propanamide;

215. 2-Amino-2-methyl-N-[ 2,3,4,5-tetrahydro-4-[[ 2'-[ [(methoxycarbonyl)amino]methyl][1,1'-biphenyl]-4-yl]-methyl]-3-oxo-1,4-benzothiazepin-2(R)-yl]propanamide;

216. 3-Amino-3-methyl-N-[2,3,4,5-tetrahydro-4-[[2'-[ [(methoxycarbonyl)amino]methyl] [1,1'-biphenyl]-4- yl]-methyl]-3-oxo-1,4-benzothiazepin-2(R)-yl]butanamide;

217. 3-[2(R)-Hydroxypropyl]amino-3-methyl-N-[2,3,4,5-tetrahydro- 4-[[2'-[[(methoxycarbonyl)amino]methyl][1,1'-biphenyl]-4-yl]methyl]-3-oxo-1,4-benzothiazepin-2(R)-yl]-butanamide; and 218. 3-[2(S),3-Dihydroxypropyl]amino-3-methyl-N-[2,3,4,5-tetrahydro- 4-[[2'-[[(methoxycarbonyl)amino]methyl][1,1'-biphenyl]-4-yl]methyl]-3-oxo-1,4-benzothiazepin-2(R)-yl]-butanamide.

Representative examples of the nomenclature employed are given below:

2-Amino-2-methyl-N-[2,3,4,5-tetrahydro-7-methyl-2-[[2'- [[(methylamino)carbonyl]amino][1,1'-biphenyl]-4-yl]methyl]-3-oxo-1H-2-benzazepin-4(R)-yl]propanamide

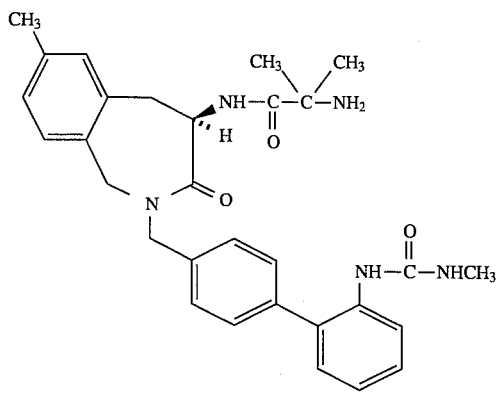

N-Ethyl-4'-[[4(R)-[[[[2(R)-hydroxypropyl]amino]-3-methyl-1-oxobutyl]-amino]-2,3,4,5-tetrahydro-3-oxo-1H-2-benzazepin-2-yl]methyl][1,1'-biphenyl]-2-carboxamide

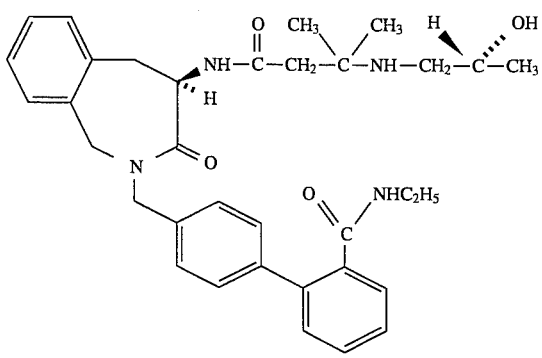

3-[2(S),3-Dihydroxypropyl]amino-3-methyl-N-[2,3,4,5-tetrahydro-7-methyl-3-oxo-4-[[2'-(1H-tetrazol-5-yl)[1,1'-biphenyl]-4-yl]methyl]-1,4-benzothiazepin-2(R)-yl]butanamide

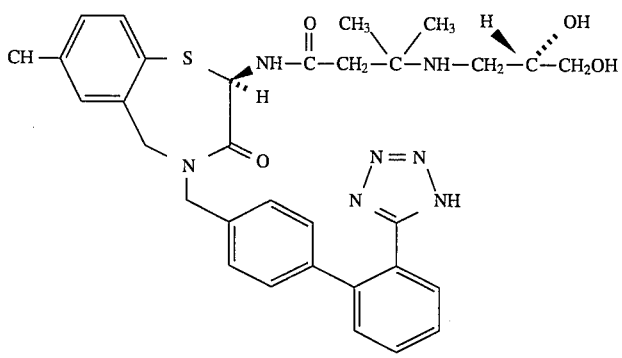

3-Amino-3-methyl-N-[2,3,4,5-tetrahydro-3-oxo-4-[[2'-[2-[[4-morpholinocarbonyl]amino]ethyl][1,1'-biphenyl]-4-yl]methyl]-1,4-benzothiazepin-2(R)-yl]butanamide

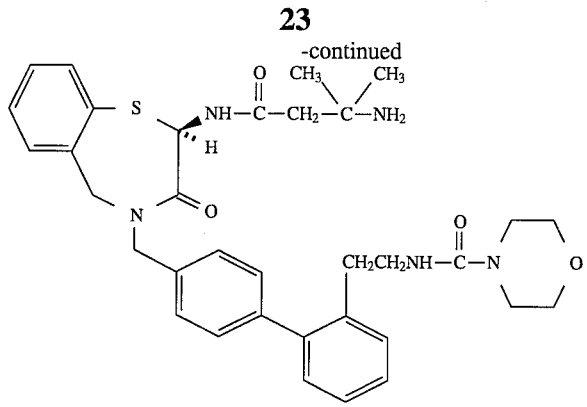

The compounds of the instant invention all have at least one asymmetric center as noted by the asterisk in the structural Formula I above. Additional asymmetric centers may be present on the molecule depending upon the nature of the various substituents on the molecule. Each such asymmetric center will produce two optical isomers and it is intended that all such optical isomers, as separated, pure or partially purified optical isomers or racemic mixtures thereof, be included within the ambit of the instant invention. In the case of the asymmetric center represented by the asterisk in Formula I, it has been found that the compound in which the 4-amino substituent is above the plane of the structure, as seen in Formula Ia, is more active and thus more preferred over the compound in which the 4-amino substituent is below the plane of the structure. The asymmetric center will be designated according to the R/S rules as either R or S depending upon the value of X.

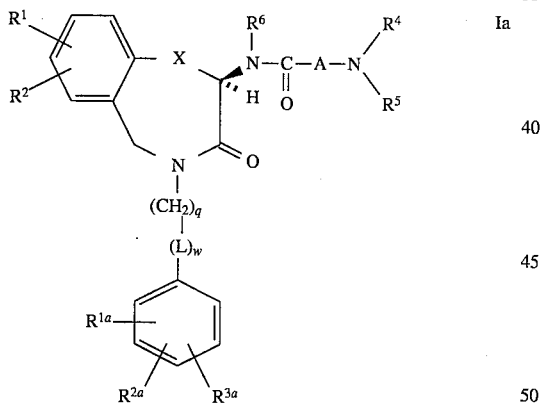

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic and the like. In addition, certain compounds containing an acidic function such as a tetrazole or carboxy can be isolated in the form of their inorganic salt in which the counterion can be selected from sodium, potassium, lithium, calcium, magnesium and the like, as well as from organic bases.

Compounds (I) of the present invention are prepared from aminolactam intermediates such as those of formula II. The preparation of these intermediates is described in the following reaction Schemes.

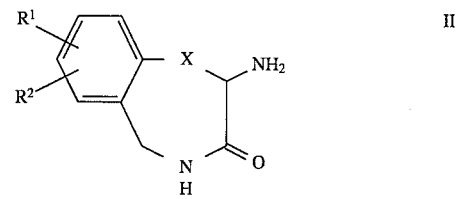

Benzo-fused lactams 6 wherein X is a methylene ($CH_2$) group are conveniently prepared from appropriately substituted derivatives of o-tolunitrile as shown in Scheme 1.

SCHEME 1

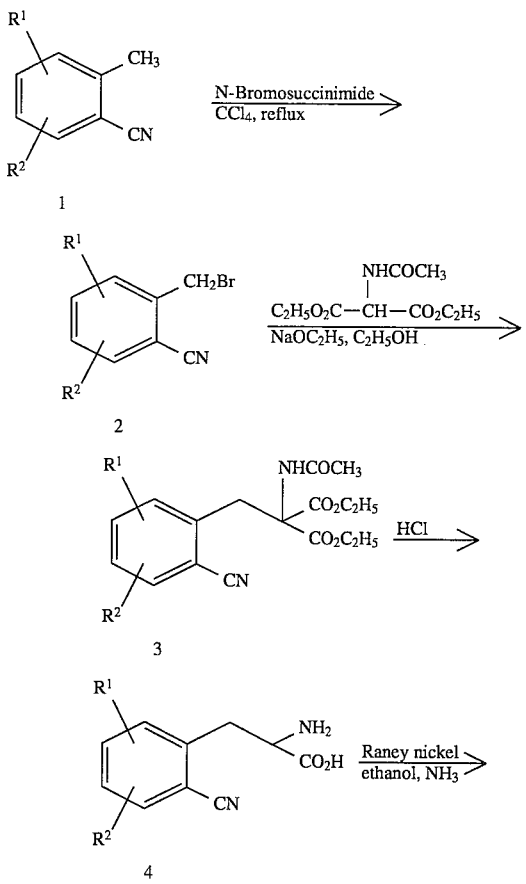

25
-continued
SCHEME 1

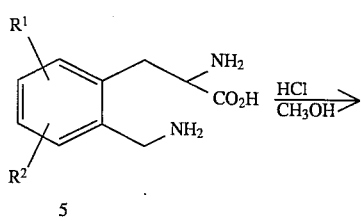

5

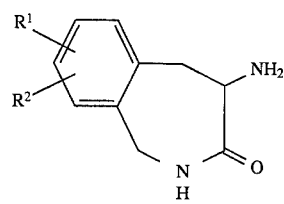

6

Thus, free-radical bromination of the substituted nitrile 1 with N-bromosuccinimide and a radical initiator, such as azobisiso-butyronitrile (AIBN) or benzoyl peroxide, gives the bromide 2. Reaction with the sodium salt of acetamido diethylmalonate affords the alkylated product 3,which is hydrolyzed under acidic conditions to produce the amino acid derivative 4. Reduction of the nitrile to the aminomethyl compound 5is achieved by treatment of 4 with Raney nickel in a polar solvent, such as ethanol, in the presence of ammonia. Cyclization to the aminolactam 6 is then carried out by treatment of a methanol solution of 5 with hydrochloric acid at elevated temperatures.

Chiral aminobenzolactams are obtained by resolution of the racemates by classical methods familiar to those skilled in the art. For example, resolution can be achieved by formation of diastereomeric salts of the racemic amines with optically active acids such as D- and L-tartaric acid. Determination of absolute stereochemistry can be achieved in a number of ways including X-ray analysis of a suitable crystalline derivative.

A useful preparation of the chiral aminolactam 11 is outlined in Scheme 2. Asymmetric alkylation of the sodium salt of t-butyl (2S,3R)-(+)-6-oxo-2,3-diphenyl-4-morpholine carboxylate 7 with α-bromo-o-tolunitrile 8, according to the procedure of Williams and Im (*J. Amer. Chem. Soc.* 1991, 113, 9276–9286.), affords the product 9 with the R configuration in fair yield. Reduction of the nitrile group of 9 using sodium borohydride in the presence of cobalt (II) nitrate is accompanied by ting closure to give the substituted lactam 10 directly. The t-butoxycarbonyl (BOC) and chiral auxilliary groups are removed sequentially by treatment with trifluoroacetic acid in methylene chloride followed by hydrogenation in the presence of palladium (H) chloride. Thus, 4(R)-amino-2,3,4,5-tetrahydro-1H-2-benzazepin-3-one (11) is obtained in good overall yield and in high enantiomeric excess.

SCHEME 2

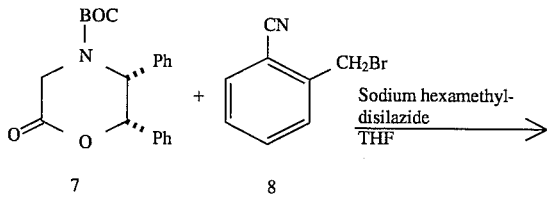

26
-continued
SCHEME 2

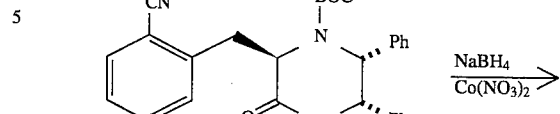

9

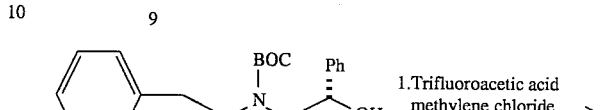

10

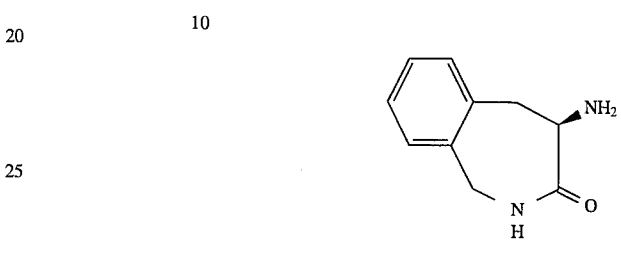

11

Intermediates of formula II wherein X is a sulfur atom (14) are prepared from the unsubstituted benzothiazepinone 12 as shown in Scheme 3. Reaction of benzothiazepinone 12 (prepared by the methods of Buckett, et al, WO 92/21668) with sulfuryl chloride in an inert solvent, such as chloroform, under conditions described by Worley, et al (*J. Org. Chem.* 1975, 40, 1731–1734.) gives the 2-chloro derivative 13. Elaboration of the chloro-lactam to the desired aminolactam intermediate 14 is achieved by reaction of 13 with gaseous ammonia in a polar solvent, such as methanol. Alteratively, tetramethylguanidinium azide in a solvent such as methylene chloride can be employed to form the corresponding 2-azido derivative which may be reduced with triphenylphosphine in wet toluene to give comparable results.

SCHEME 3

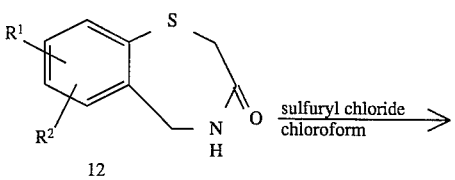

12

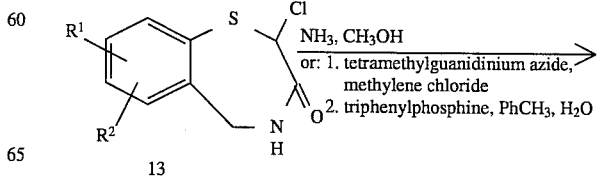

13

-continued
SCHEME 3

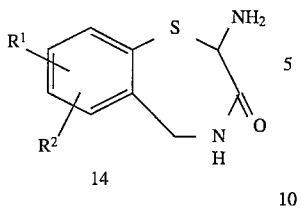

Intermediates of formula II can be further elaborated to new intermediates (formula III) which are substituted on the amino group (Scheme 4). Reductive alkylation of II with an aldehyde is carried out under conditions known in the art; for example, by catalytic hydrogenation with hydrogen in the presence of platinum, palladium or nickel catalysts or with chemical reducing agents such as sodium cyanoborohydride in a polar solvent such as methanol or ethanol.

SCHEME 4

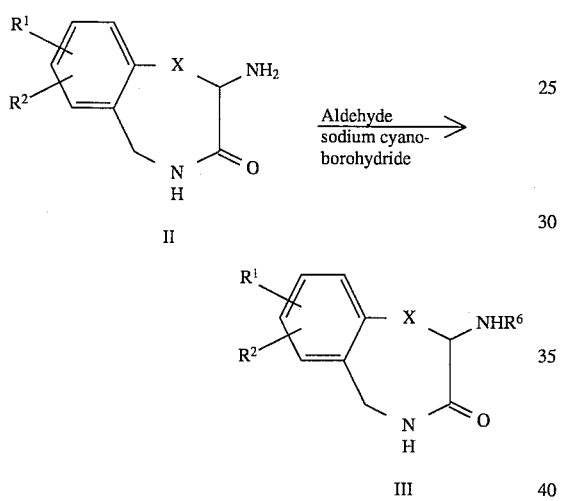

Attachment of the amino acid sidechain to intermediates of formula III is accomplished by the route shown in Scheme 5. Coupling is conveniently carried out by the use of an appropriately protected amino acid derivative, such as that illustrated by formula IV, and a coupling reagent such as benzotriazol-1-yloxytris(dimethylamino)-phosphonium hexafluorophosphate ("BOP") in an inert solvent such as methylene chloride. Separation of unwanted side products, and purification of intermediates is achieved by chromatography on silica gel, employing flash chromatography (W. C. Still, M. Kahn and A. Mitra, *J. Org. Chem.* 1978, 43, 2923.) or by medium pressure liquid chromatography.

SCHEME 5

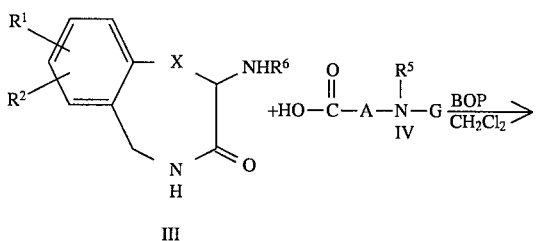

-continued
SCHEME 5

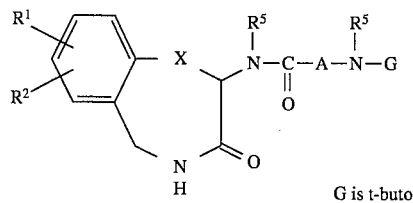

G is t-butoxycarbonyl or benzyloxycarbonyl

Sulfoxide and sulfone intermediates of formula V, wherein X is SO or $SO_2$, respectively, are prepared by oxidation of V, wherein X is sulfur, with various oxidants such as sodium periodate or m-chloroperbenzoic acid.

The protected amino acid derivatives IV are, in many cases, commercially available in t-butoxycarbonyl (BOC) or benzyloxy-carbonyl (CBz) forms. A useful method to prepare a preferred sidechain 19, is shown in Scheme 6.

SCHEME 6

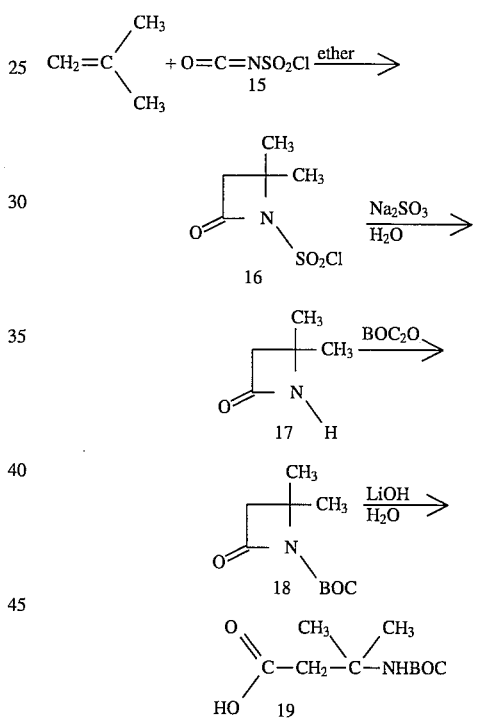

Reaction of isobutylene with N-chlorosulfonylisocyanate 15 in diethyl ether gives the azetidinone derivative 16. Removal of the chlorosulfonyl group with aqueous sodium sulfite followed by reaction with di-t-butyldicarbonate gives the BOC-protected intermediate 18. Alkaline hydrolysis gives the protected amino acid derivative 19 in good overall yield.

Intermediates of formula VII are prepared as shown in Scheme 7 by treatment of the desired lactam intermediate V with an alkylating agent VI, wherein Y is a good leaving group such as Cl, Br, I, O-methanesulfonyl or O-(p-toluenesulfonyl). Alkylation of intermediates of formula V is conveniently carried out in anhydrous dimethyl formamide (DMB in the presence of bases such as sodium hydride or potassium t-butoxide for a period of 0.5 to 24 hours at temperatures of 20°–100° C. Substituents on the alkylating agent VI may need m be protected during alkylation. A description of such protecting groups may be found in: *Protective Groups in Organic Synthesis,* T. W. Greene, John Wiley and Sons, New York, 1981.

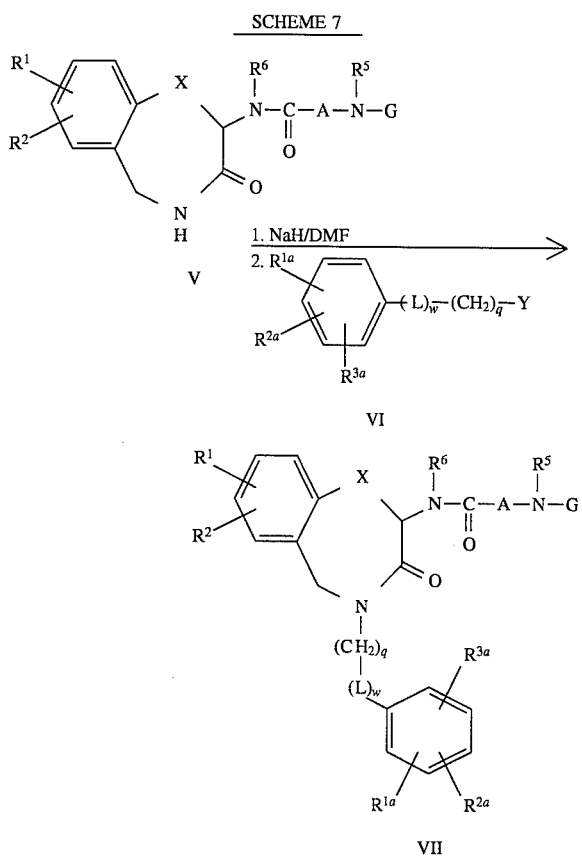

VI

VII

Y is a leaving group
G is t-butoxycarbonyl or benzyloxycarbonyl

Alkylating agents VI are, in some cases commercially available compounds or may be prepared as described in EPO publications 253,310; 291,969; 324,377 and the references cited therein.

Compounds of formula I wherein $R^{3a}$ or $R^{3b}$ is a tetrazole are prepared as described in Scheme 8 by alkylation of V with a suitably substituted alkylating agent VI containing a nitrile as tetrazole precursor. Elaboration of nitrile 20 to the desired tetrazole product 21 is carried out by treatment with trimethyltin azide in refluxing toluene.

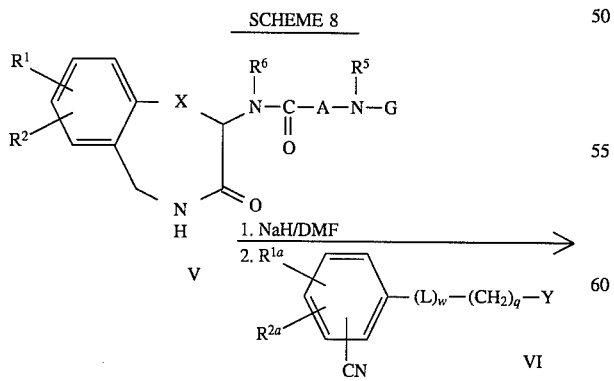

VI

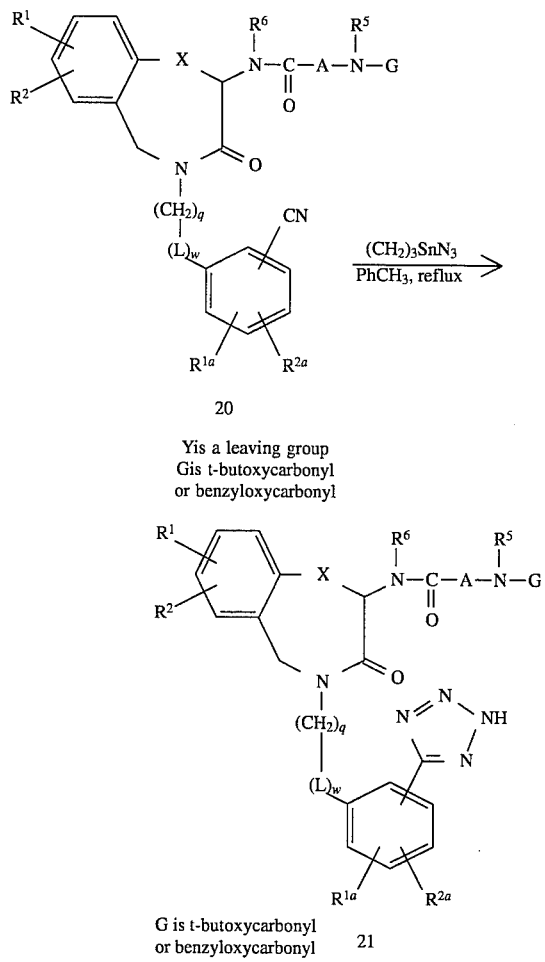

20

Y is a leaving group
G is t-butoxycarbonyl or benzyloxycarbonyl

21

G is t-butoxycarbonyl or benzyloxycarbonyl

A useful method to prepare a preferred alkylating agent 26 is shown in reaction Scheme 9, and in U.S. Pat. No. 5,039,814.

SCHEME 9

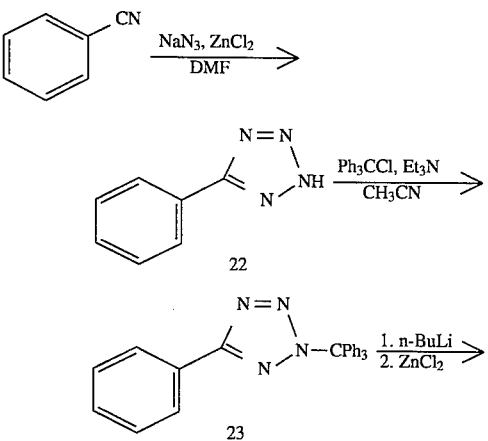

22

23

SCHEME 9 -continued

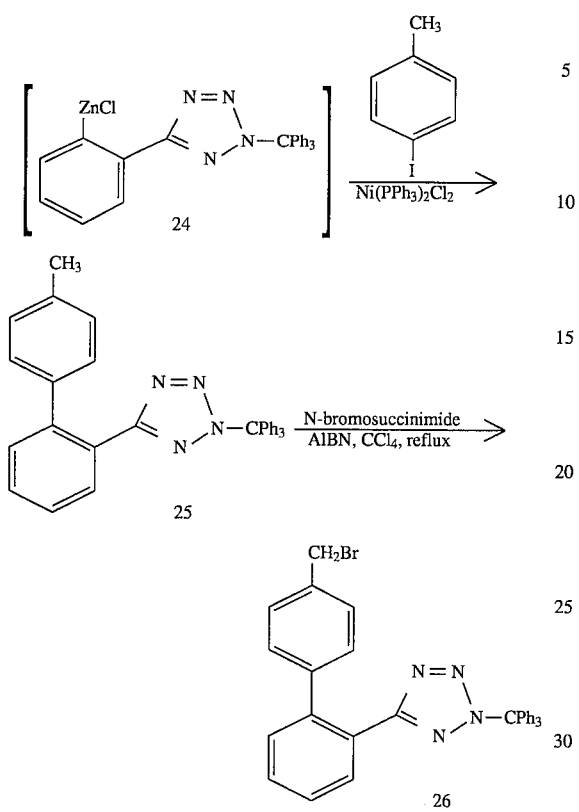

As outlined in Scheme 9, benzonitrile is treated with sodium azide and zinc chloride to give 5-phenyltetrazole 22 which is convened to the N-trityl derivative 23 by treatment with triphenylmethyl chloride and triethylamine. The zinc reagent 24 was prepared by treatment with n-butyl lithium followed by zinc chloride. Coupling with 4-iodotoluene using the catalyst bis(triphenylphosphine)nickel(II) dichloride gives the biphenyl product 25 in high yield. Treatment with N-bromosuccmimide in refluxing carbon tetrachloride in the presence of a radical initiator such as benzoyl peroxide or 2,2'-azobisisobutyronitrile (AIBN) gives bromide 26.

Compounds of formula I where $R^{3a}$ or $R^{3b}$ is a carbamate, semicarbazide or urea derivative, wherein this functionality is attached to the phenyl ring by a nitrogen atom are prepared from intermediate 27, obtained by alkylation with a derivative of formula VI wherein $R^{3a}$ or $R^{3b}$ is a nitro group as shown in Scheme 10.

SCHEME 10

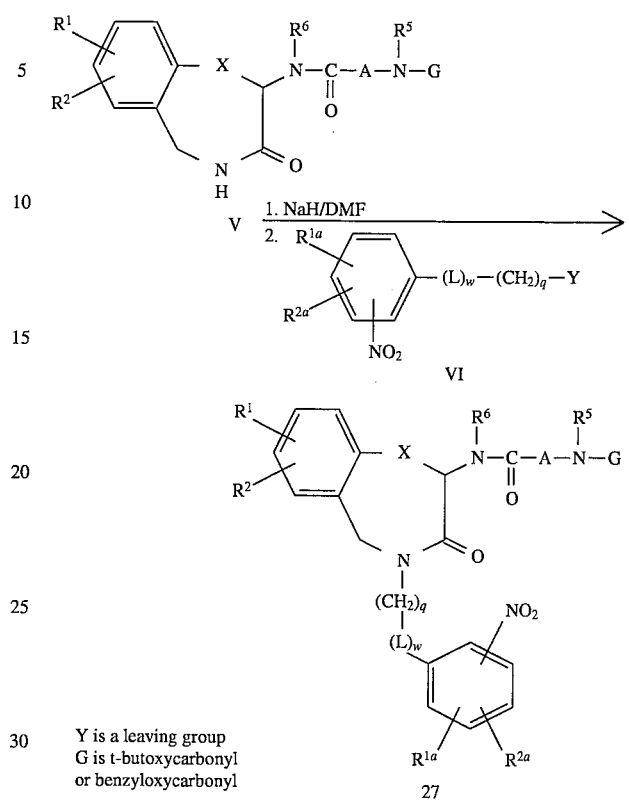

Y is a leaving group
G is t-butoxycarbonyl or benzyloxycarbonyl

A useful method of synthesizing a preferred alkylating agent 31 is shown in reaction Scheme 11.

SCHEME 11

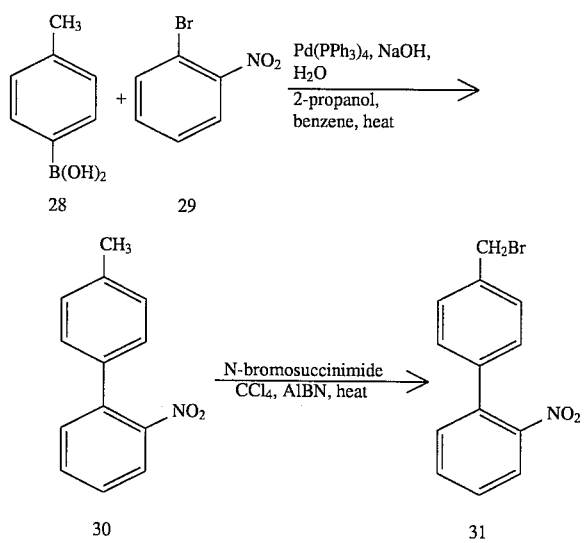

Reaction of 4-tolylboronic acid 28 with 2-bromonitrobenzene 29 in the presence of a transition metal catalyst such as (tetrakis)triphenylphosphine palladium (O) in a mixed solvent system containing aqueous sodium hydroxide, water, 2-propanol and benzene at elevated temperatures for several hours gives the coupled product 30 in good overall yield. Chromatographic purification and separation of unwanted by-products is conveniently performed on silica, eluting with common organic solvents such as hexane, ethyl acetate and methylene chloride. Conversion of 30 to the bromide derivative 31 is accomplished by the aforementioned reaction with N-bromosuccinimide.

As shown in Scheme 12, reduction of the nitro group of 27 is achieved by hydrogenation in the presence of a metal catalyst, such as palladium on carbon, in a protic solvent such as methanol or ethanol. It may be appreciated by one skilled in the art that for certain compounds where catalytic hydrogenation is incompatible with existing functionality, alternative methods of reduction are indicated, such as chemical reduction with stannous chloride under acidic conditions. It should also be noted that the protecting group G in intermediate 27 must be compatible with the experimental conditions anticipated for reduction. For example, intermediate 27 wherein G is t-butoxycarbonyl (BOC) is stable to the conditions of catalytic reduction employed in the conversion to 32. Intermediate 32 may also be further elaborated to a new intermediate 33 by reductive alkylation carried out under the aforementioned conditions.

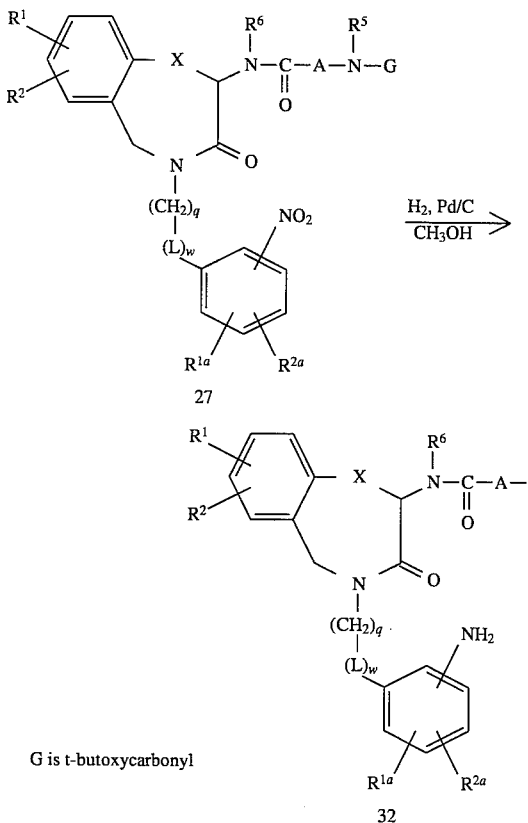

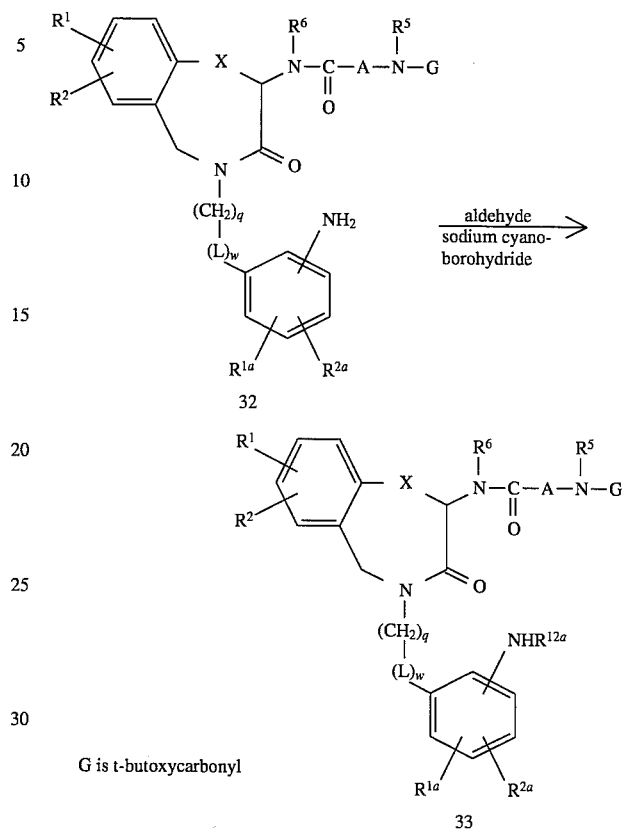

Elaboration of 33 to carbamate compound 34 is achieved by reaction with the appropriate chloroformate reagent in pyridine or in methylene chloride with triethylamine as shown in Scheme 13.

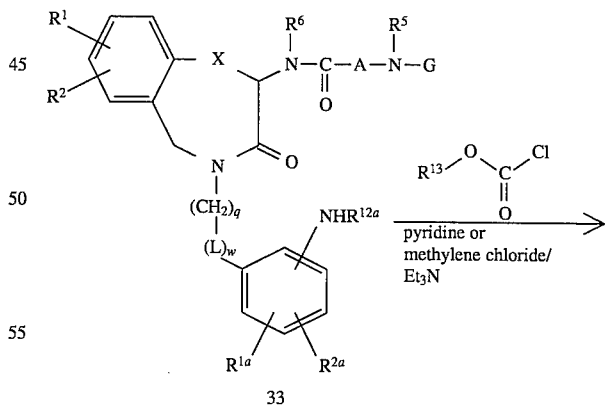

35
-continued
SCHEME 13

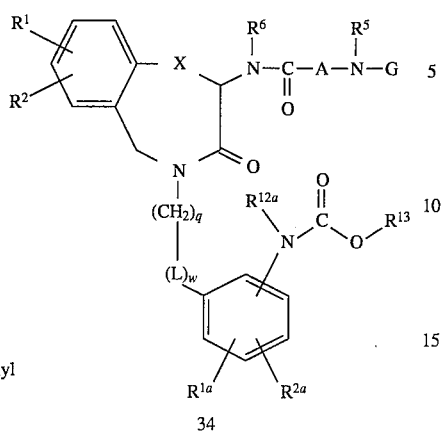

G is t-butoxycarbonyl

Transformation of amine intermediate 33 to urea derivatives is accomplished in several ways. Terminally disubstituted compounds 36 can be obtained directly by reaction of 33 with a disubstituted carbamoyl chloride 35 in an inert solvent such as methylene chloride in the presence of triethylamine or 4-dimethylaminopyridine. In addition, mono-substituted compound 38 wherein either $R^{5b}$ or $R^{12b}$ is hydrogen is obtained from 33 by reaction with an isocyanate 37 as shown in Scheme 14. Terminally unsubstituted urea 38, wherein $R^{12b}$ is hydrogen, is also prepared from amine 33 by reaction with trimethylsilyl isocyanate (37; $R^{12b}$ is $(CH_3)_3Si$).

SCHEME 14

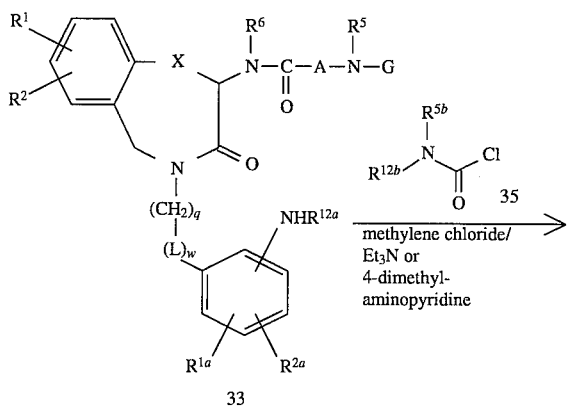

G is t-butoxycarbonyl

36
-continued
SCHEME 14

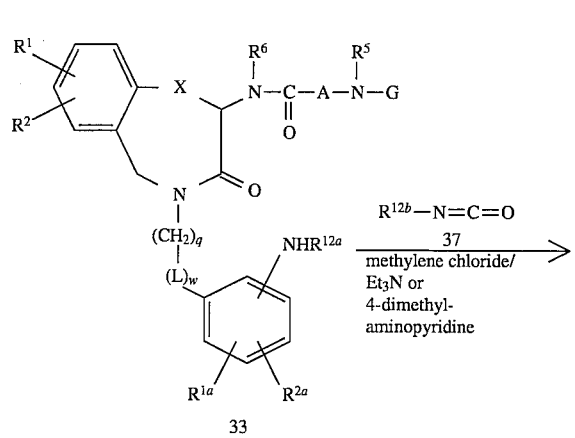

G is t-butoxycarbonyl

Alternatively, amine 32 is converted to an isocyanate 39 by treatment with phosgene or an equivalent reagent such as bis(trichloromethyl)carbonate (triphosgene) as indicated in Scheme 15. Subsequent reaction of 39 with primary or secondary amines in an inert solvent such as methylene chloride gives the corresponding urea derivative 36 in good yield. Isocyanate 39 is also converted to substituted semicarbazides 40 or hydroxy- or alkoxyureas 41 by reaction with substituted hydrazines or hydroxy- or alkoxylamines, respectively.

SCHEME 15

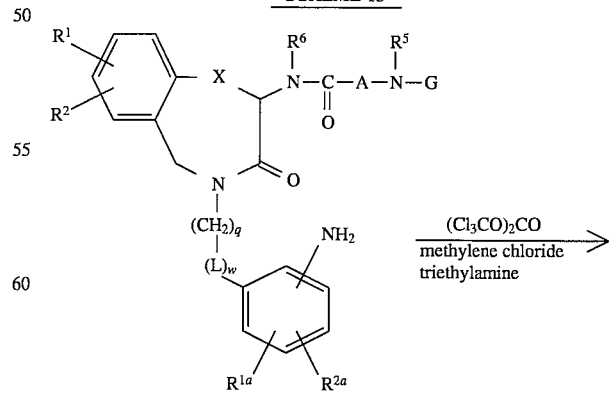

-continued
SCHEME 15
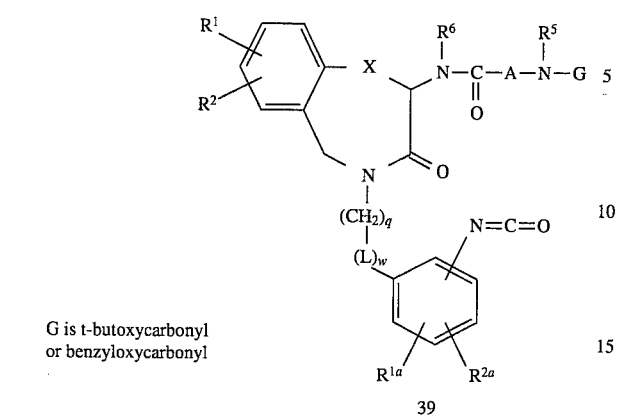
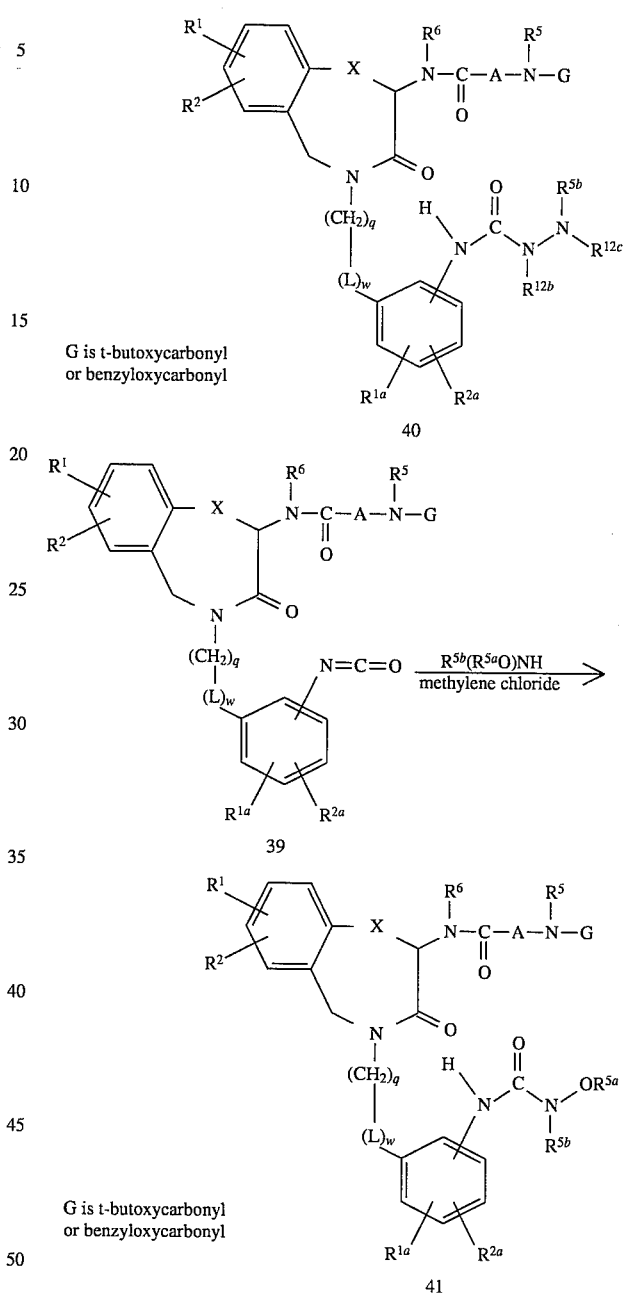
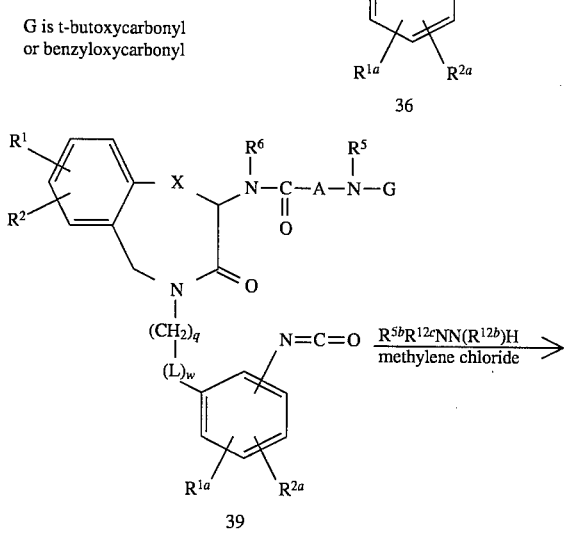
Compounds of formula I where $R^{3a}$ or $R^{3b}$ is a carbazate or carbamate derivative where attachment to the phenyl ring is through the oxygen atom of the carbazate or carbamate linkage are prepared from acetophenone intermediate 42 as indicated in Scheme 16.

SCHEME 16

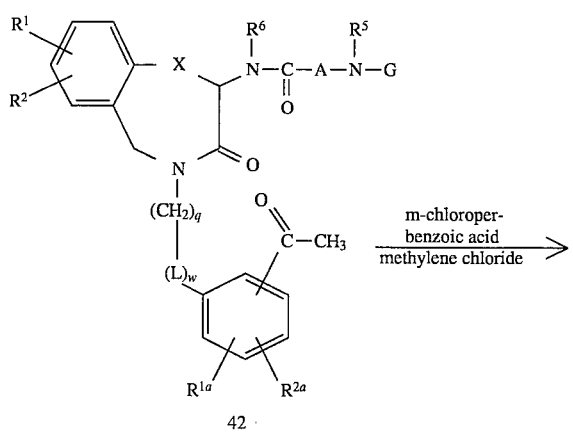

42

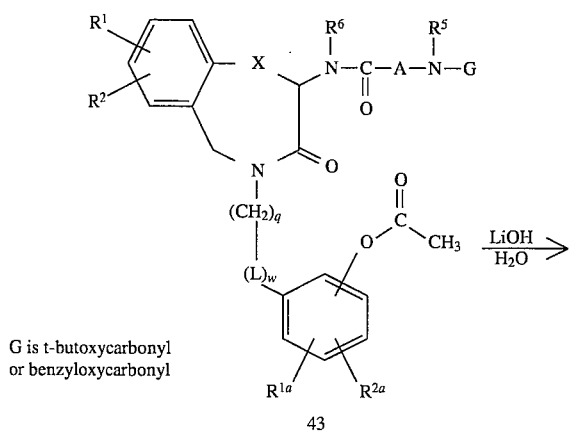

G is t-butoxycarbonyl
or benzyloxycarbonyl

43

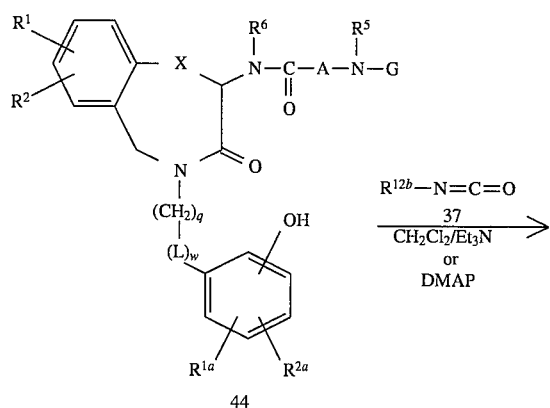

44

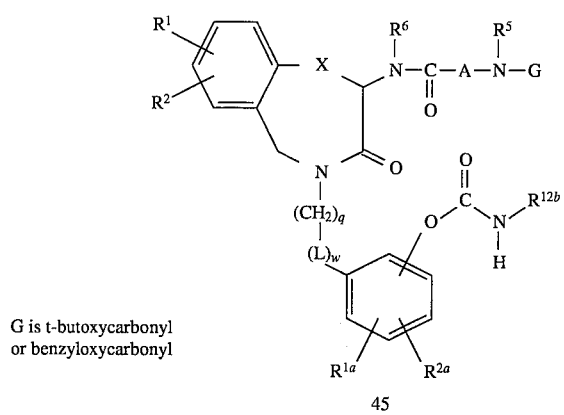

G is t-butoxycarbonyl
or benzyloxycarbonyl

45

-continued
SCHEME 16

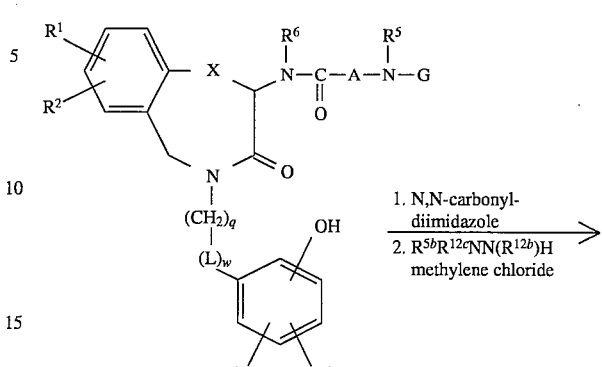

44

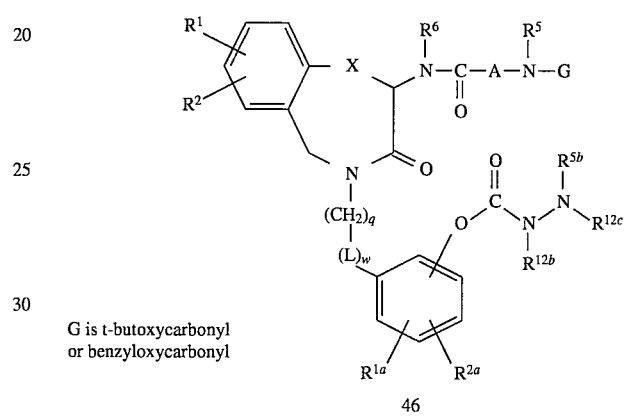

G is t-butoxycarbonyl
or benzyloxycarbonyl

46

Oxidative rearrangement of 42 through the use of a peroxy-carboxylic acid (Baeyer-Villager reaction) such as m-chloroperbenzoic acid gives the ester 43 which is hydrolyzed in the presence of a strong base such as sodium or lithium hydroxide to give phenol 44. Reaction of 44 with an isocyanate 37 leads directly to carbamate 45. Additionally, treatment of 44 with N,N'-carbonyldiimidazole in dimethylformamide can form an activated intermediate which will react with substituted hydrazine reagents to give the carbazate product 46.

Compounds of formula I wherein $R^{3a}$ or $R^{3b}$ is $R^{5b}R^{12b}NCON(R^{12a})CH_2$—, $R^{5b}R^{12b}NCSN(R^{12a})CH_2$—, $R^{5b}R^{12c}NN(R^{12b})CSN(R^{12a})CH_2$—, $R^{5b}R^{12c}NN(R^{12b})CON(R^{12a})CH_2$— or $R^{13}OCON(R^{12a})CH_2$— are prepared from the t-butyl ester intermediate 47 as described in Scheme 17. Removal of the t-butyl ester through the use of trifluoroacetic acid gives the carboxylic acid 48. It may be appreciated by one skilled in the art that the protecting group G in 47 must therefore be compatible with the strongly acidic conditions employed for ester cleavage; hence G is taken as benzyloxycarbonyl. Conversion of the carboxylic acid 48 to the benzylamine derivative 49 can be achieved by a five-step sequence consisting of: 1) formation of a mixed anhydride with isobutyl chloroformate; 2) reduction with sodium borohydride to the benzyl alcohol; 3) formation of the mesylate with methanesulfonyl chloride; 4) formation of the azide by reaction with sodium azide, and finally, 5) reduction of the azide with tin(II) chloride. The benzylamine intermediate 49 can be further elaborated to 50 by the aforementioned reductive amination procedure.

SCHEME 17

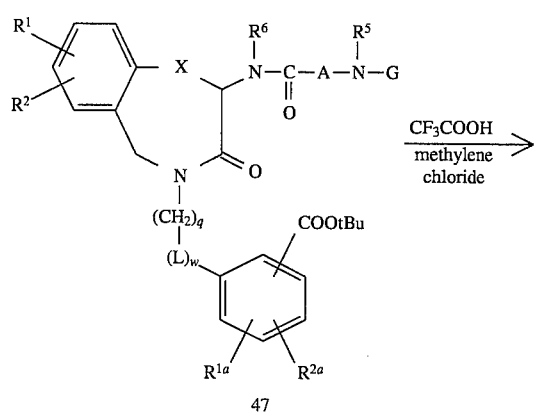

47

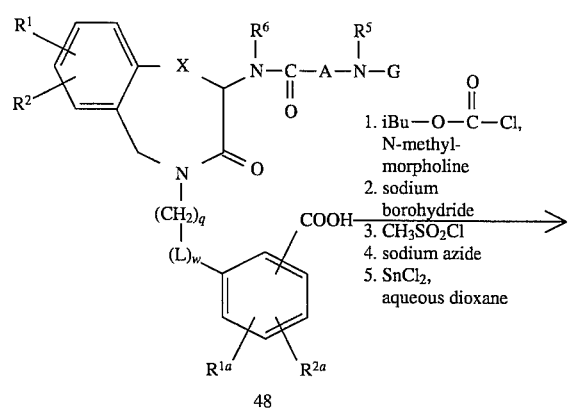

48

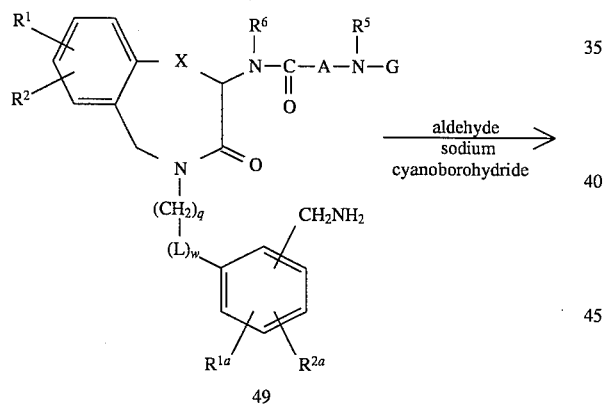

49

-continued
SCHEME 17

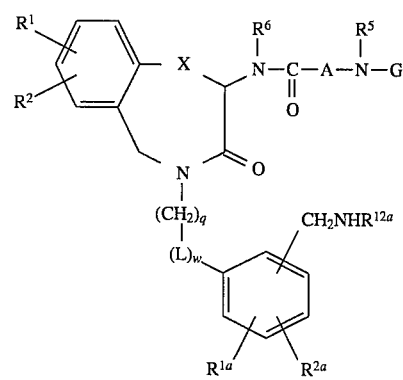

50

G is benzyloxycarbonyl

Reactions of amine 50 with the appropriate reagents to form urea-linked compounds 51 and 52, carbamate-linked compound 53 and semicarbazide compound 54 are illustrated in Scheme 18. Terminally unsubstituted urea 51, wherein $R^{12b}$ is hydrogen, is also prepared from amine 50 by reaction with trimethylsilyl isocyanate (37; $R^{12b}$ is $(CH_3)_3Si$).

SCHEME 18
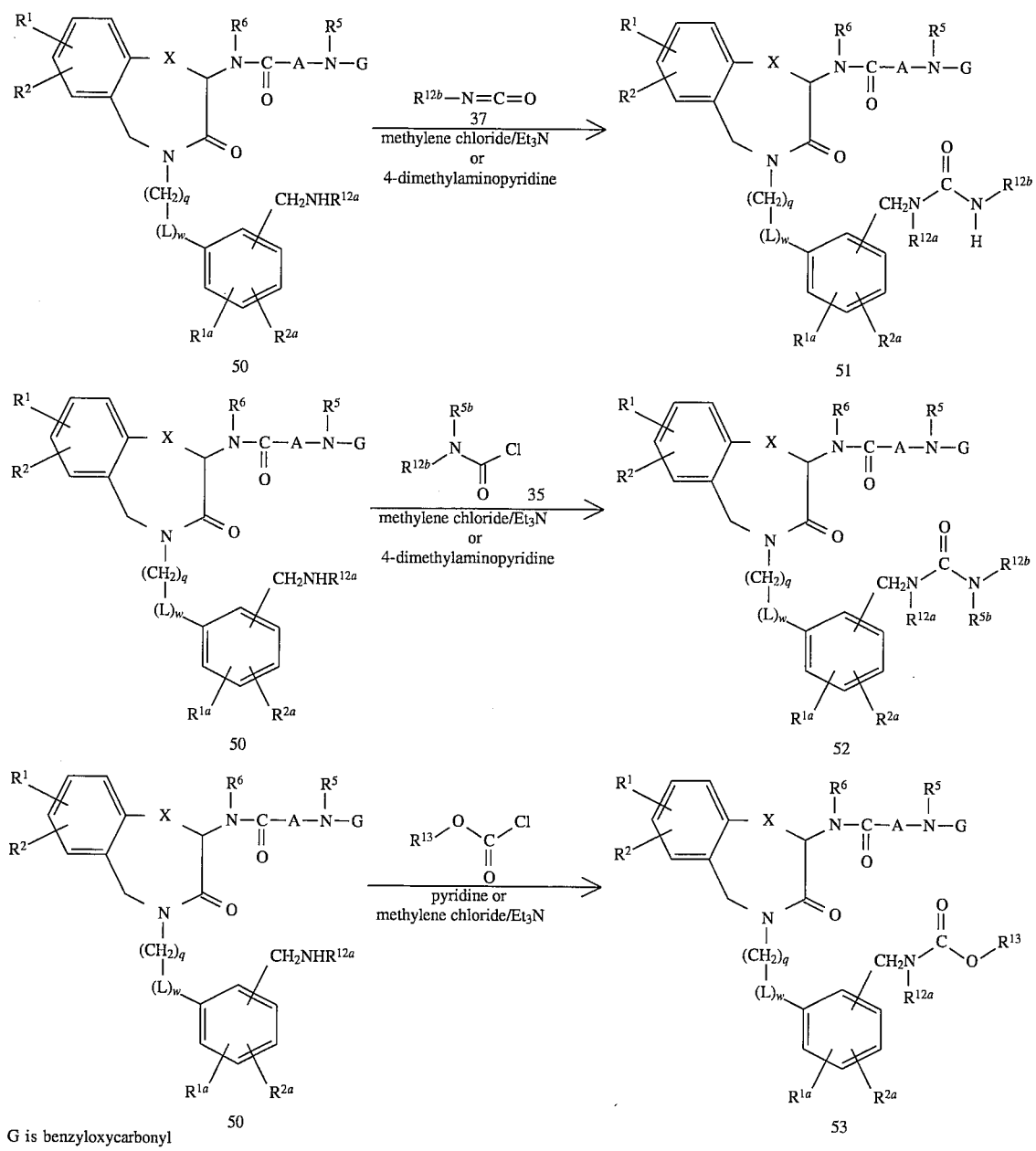
G is benzyloxycarbonyl
As shown in Scheme 19, hydrazide compound 54 can be prepared from intermediate 50 by a two-step procedure consisting of activation of the amine via treatment with N,N'-carbonyldiimidazole followed by treatment with the appropriately substituted hydrazine derivative $R^{5b}R^{12c}NN(R^{12b})H$.

SCHEME 19

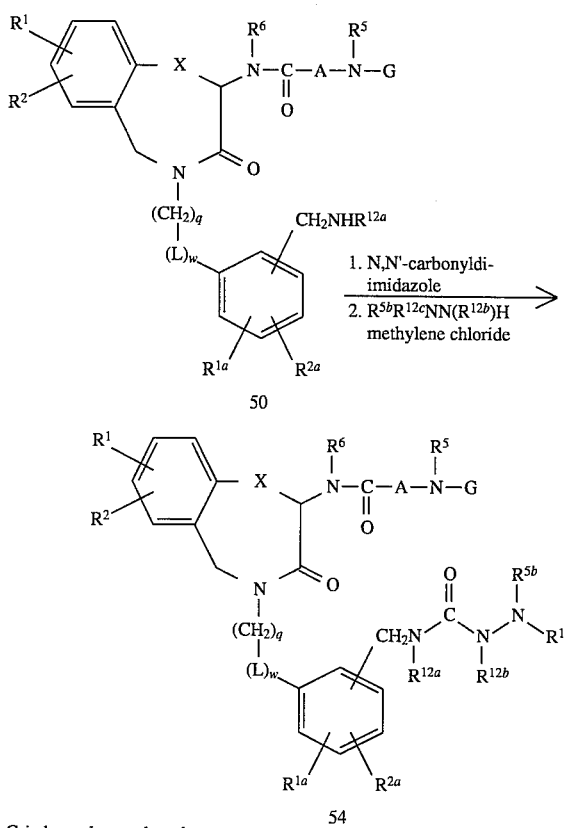

G is benzyloxycarbonyl

A useful preparation of the protected benzylamine intermediate 59 is shown in Scheme 20. Metallation of 4-bromobenzyl t-butyldiphenylsilylether 55 with n-butyllithium followed by treatment with triisopropyl borate gives the aryl boronic acid 56. Reaction of 56 with 2-bromo-N-(t-butoxycarbonyl)benzylamine 57 in the presence of tetrakis(triphenylphosphine)palladium(O) and sodium hydroxide in a mixed solvent system at elevated temperature gives the coupled product 58 in good yield. Desilylation and conversion to the O-methanesulfonate 59 is achieved by treatment with tetrabutylammonium fluoride followed by methanesulfonyl chloride. Reaction of 59 with compounds of formula V is carried out using the conditions described in Scheme 7.

SCHEME 20

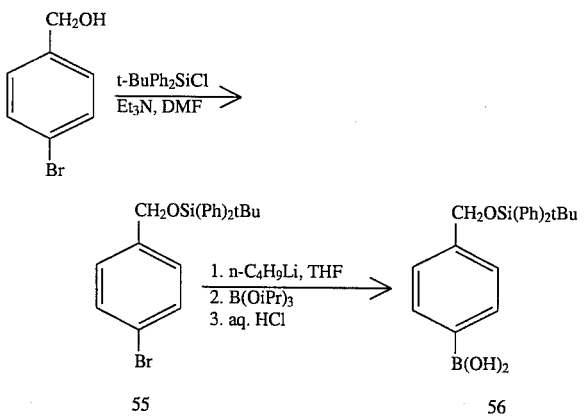

SCHEME 20 -continued

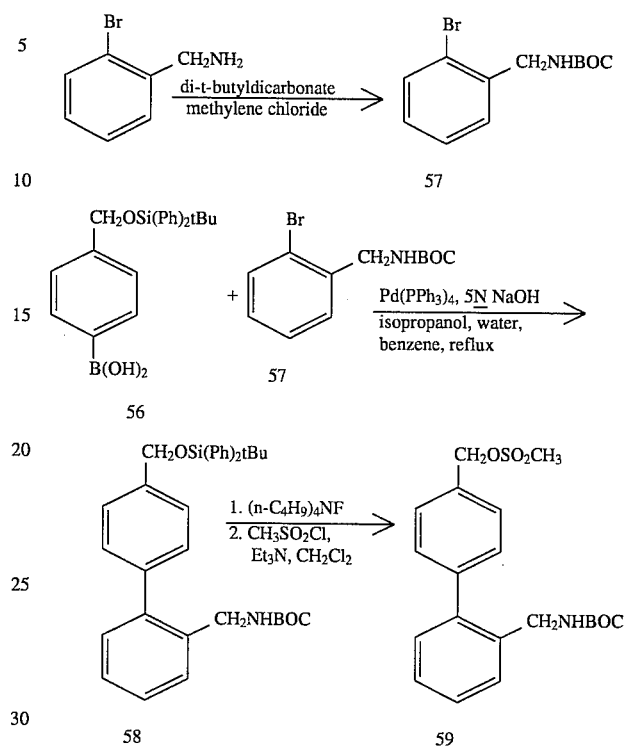

Compounds of Formula I wherein $R^{3a}$ or $R^{3b}$ is taken as $R^{5b}R^{12b}NCO$ are prepared by several methods. For example, as shown in Scheme 21, compound 60 wherein $R^{5b}$ and $R^{12b}$ are both hydrogen is conveniently prepared by hydrolysis of the nitrile precursor 20.

SCHEME 21

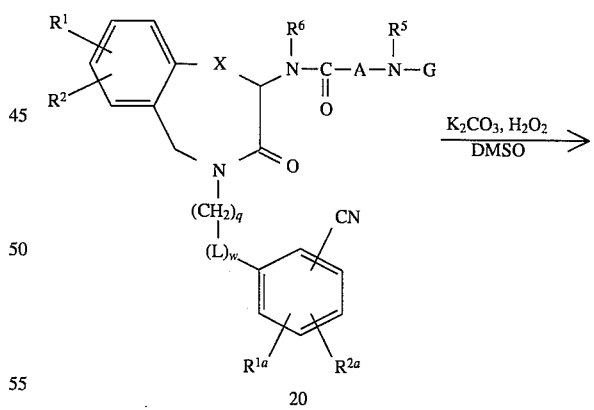

SCHEME 21 -continued

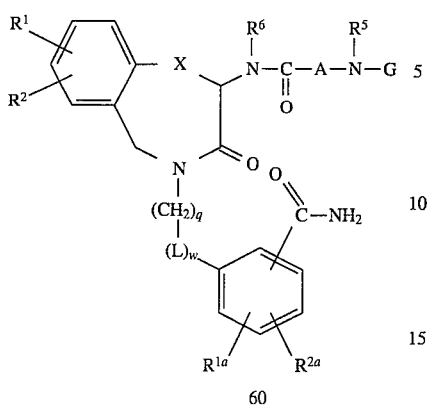

60

G is t-butoxycarbonyl or benzyloxycarbonyl

Thus, treatment of nitrile 20 with hydrogen peroxide and a strong base, such as potassium carbonate, in a polar solvent, such as dimethylsulfoxide at temperatures of 25° C. to 150° C. results in formation of the amide derivative 60. The precursor 20 is prepared from an appropriate alkylating agent VI, where $R^{3a}$ is cyano, as described in Scheme 8.

A useful method of preparing the alkylating agent 63 is outlined in Scheme 22.

SCHEME 22

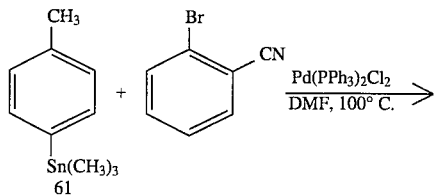

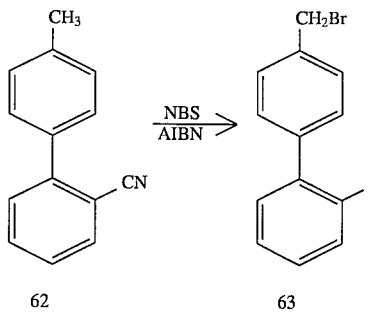

Thus, treatment of 4-(methylphenyl)trimethyl stannane 61 with 2-bromobenzonitrile in dimethylformamide at 100° C. in the presence of bis-triphenylphosphine palladium (II) chloride results in coupling to form the biphenyl nitrile 62 in high yield. Conversion to bromide 63 is achieved by the aforementioned treatment with N-bromosuccinimide.

Compounds of formula I wherein $R^{3a}$ or $R^{3b}$ is taken as $R^{5b}R^{12b}NCO-$ and $R^{5b}$ and/or $R^{12b}$ are other than hydrogen (64) are prepared from the corresponding carboxylic acid derivative 48 as shown in Scheme 23.

SCHEME 23

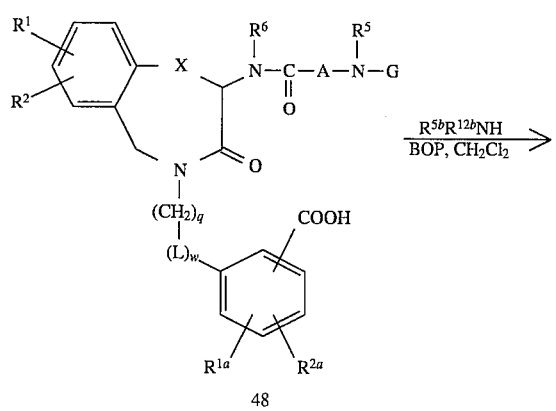

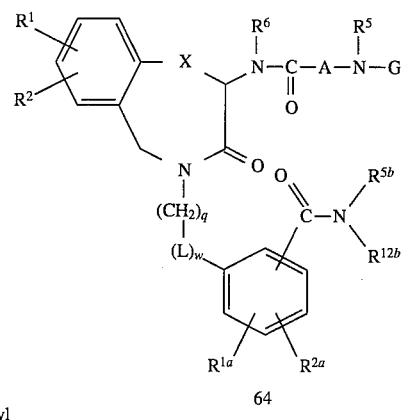

64

G is benzyloxycarbonyl

Coupling of the carboxylic acid derivative 48 with $R^{5b}R^{12b}NH$ is conveniently carried out by the use of the coupling reagent "BOP" described previously, in an inert solvent such as methylene chloride. The requisite carboxylic acid precursors are prepared as illustrated in Scheme 24 for the biphenyl compound 67.

SCHEME 24

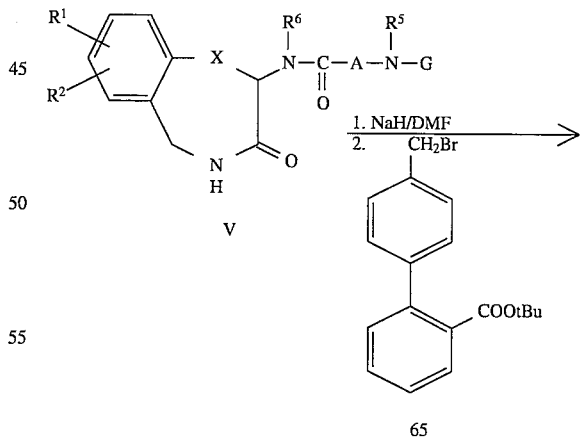

65

-continued
SCHEME 24

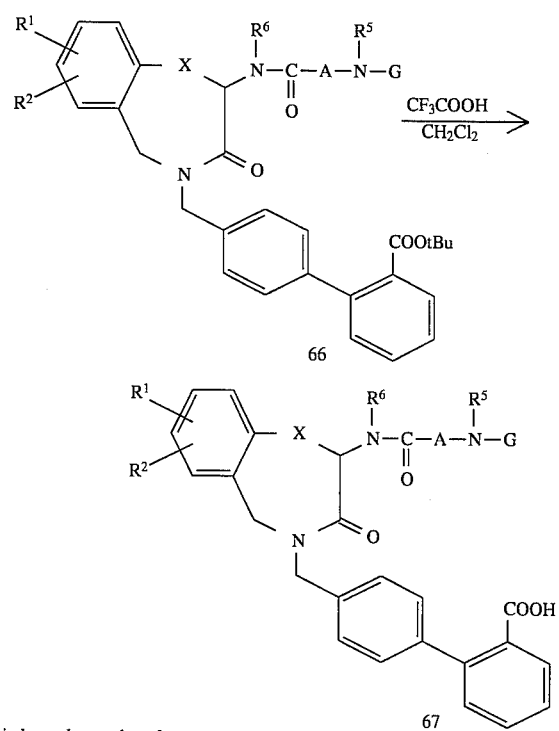

G is benzyloxycarbonyl

Alkylation of V with t-butyl 4'-bromomethyl-biphenyl-2-carboxylate 65 (prepared as described in EPO Publication 324,377) in the presence of sodium hydride as previously described in Scheme 7 gives the adduct 66 in high yield. Hydrolysis of the t-butyl ester to give the acid 67 is achieved by treatment with a strong acid, such as trifluoroacetic acid, in an inert solvent such as methylene chloride. It is noted that the protecting group G in this instance must be inert to strongly acidic conditions, for example G is benzyloxycarbonyl (CBz).

Conversion to compounds of formula I wherein $R^4$ is hydrogen is carried out by simultaneous or sequential removal of all protecting groups from intermediate VII as illustrated in Scheme 25.

SCHEME 25

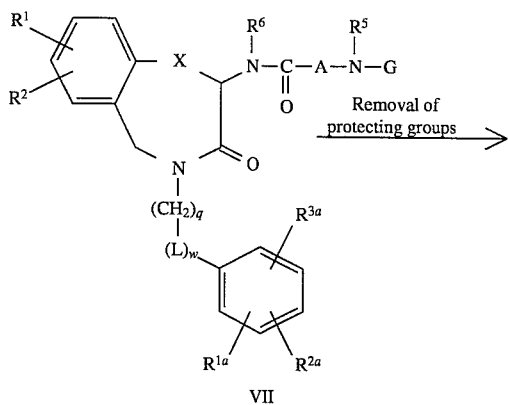

-continued
SCHEME 25

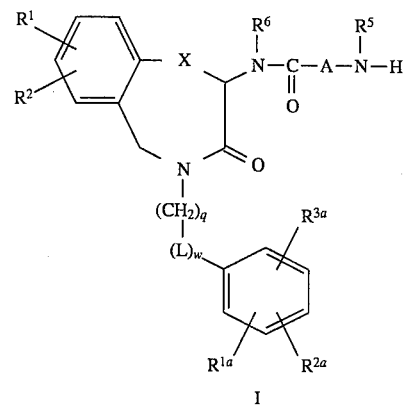

Removal of benzyloxycarbonyl (CBz) groups can be achieved by a number of methods known in the art; for example, catalytic hydrogenation with hydrogen in the presence of a platinum or palladium catalyst in a protic solvent such as methanol. In cases where catalytic hydrogenation is contraindicated by the presence of other potentially reactive functionality, removal of benzyloxycarbonyl groups can also be achieved by treatment with a solution of hydrogen bromide in acetic acid. Removal of t-butoxycarbonyl (BOC) protecting groups is carried out by treatment of a solution in a solvent such as methylene chloride or methanol, with a strong acid, such as hydrochloric acid or trifluoroacetic acid. Conditions required to remove other protecting groups which may be present can be found in *Protective Groups in Organic Synthesis* T. W. Greene, John Wiley and Sons, N.Y. 1981.

As shown in Scheme 26, compounds of formula I wherein $R^4$ is hydrogen are elaborated to new compounds by reductive alkylation with an aldehyde by the aforementioned procedures. The products, obtained as hydrochloride or trifluoroacetate salts, are conveniently purified by reverse phase high performance liquid chromatography (HPLC) or by recrystallization.

SCHEME 26

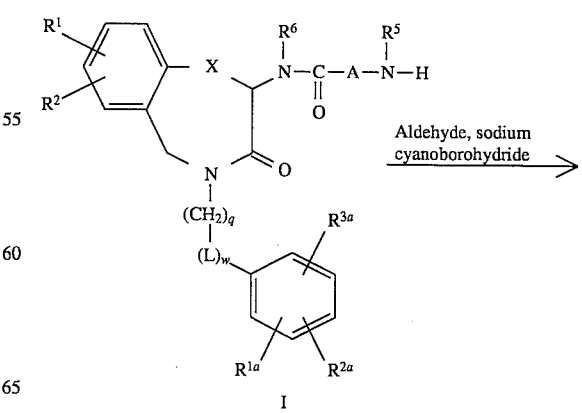

-continued
SCHEME 26

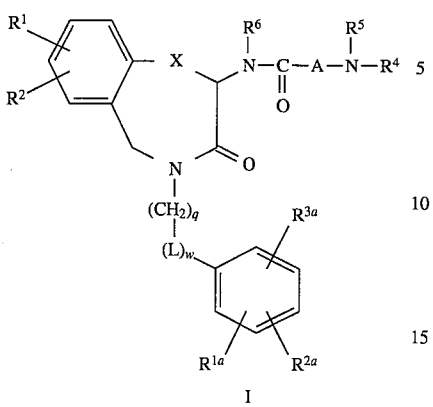

It is noted that the order of carrying out the foregoing reaction schemes is not significant and it is within the skill of one skilled in the art to vary the order of reactions to facilitate the reaction or to avoid unwanted reaction products.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive intestinal peptides, e.g., bombesin; and the thyroid hormones, e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep and the like to accelerate and increase their rate and extent of growth, and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carrier or diluent. Optionally, the active ingredient of the pharmaceutical compositions can comprise a growth promoting agent in addition to at least one of the compounds of Formula I or another composition which exhibits a different activity, e.g., an antibiotic or other pharmaceutically active material.

Growth promoting agents include, but are not limited to, TRH, diethylstilbesterol, theophylline, enkephalins, E series prostaglandins, compounds disclosed in U.S. Pat. No. 3,239, 345, e.g., zeranol, and compounds disclosed in U.S. Pat. No. 4,036,979, e.g., sulbenox or peptides disclosed in U.S. Pat. No. 4,411,890.

A further use of the disclosed novel benzo-fused lactam growth hormone secretagogues is in combination with other growth hormone secretagogues such as GHRP-6, GHRP-1 or GHRP-2 as described in U.S. Pat. No. 4,411,890; and publications WO 89/07110 and WO 89/07 111 and B-HT 920 or in combination with growth hormone releasing factor and its analogs or growth hormone and its analogs. A still further use of the disclosed novel benzo-fused lactam growth hormone secretagogues is in combination with $\alpha_2$ adrenergic agonists or $\beta_3$ adrenergic agonists in the treatment of obesity or in combination with parathyroid hormone or bisphosphonates, such as MK-217 (alendronate), in the treatment of osteoporosis. A still further use of the disclosed novel benzo-fused lactam growth hormone secretagogues is in combination with IGF-1 to reverse the catabolic effects of nitrogen wasting as described by Kupfer, et al, *J. Clin. Invest.*, 91, 391 (1993).

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses of growth hormone may be summarized as follows: stimulating growth hormone release in elderly humans; prevention of catabolic side effects of glucocorticoids; treatment of osteoporosis; stimulation of the immune system; treatment of retardation; acceleration of wound healing; accelerating bone fracture repair; treatment of growth retardation, treating renal failure or insufficiency resulting in growth retardation; treatment of physiological short stature, including growth hormone deficient children; treating short stature associated with chronic illness; treatment of obesity and growth retardation associated with obesity; treating growth retardation associated with Prader-Willi syndrome and Turner's syndrome; accelerating the recovery and reducing hospitalization of burn patients; treatment of intrauterine growth retardation, skeletal dysplasia, hypercortisolism and Cushings syndrome; induction of pulsatile growth hormone release; replacement of growth hormone in stressed patients; treatment of osteochondrodysplasias, Noonans syndrome, schizophrenia, depression, Alzheimer's disease, delayed wound healing, and psychosocial deprivation; treatment of pulmonary dysfunction and ventilator dependency; attenuation of protein catabolic response after a major operation; reducing cachexia and protein loss due to chronic illness such as cancer or AIDS. Treatment of hyperinsulinemia including nesidioblastosis; adjuvant treatment for ovulation induction; to stimulate thymic development and prevent the age-related decline of thymic function; treatment of immunosuppressed patients; improvement in muscle strength, mobility, maintenance of skin thickness, metabolic homeostasis, renal hemeostasis in the frail elderly; stimulation of osteoblasts, bone remodelling, and cartilage growth; stimulation of the immune system in companion animals and treatment of disorders of aging in companion animals; growth promotant in livestock and stimulation of wool growth in sheep.

The compounds of this invention can be administered by oral, parenteral (e.g., intramuscular, intraperitoneal, intravenous or subcutaneous injection or implant), nasal, vaginal, rectal, sublingual, or topical routes of administration and can be formulated in dosage forms appropriate for each mute of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/Kg of body weight daily are administered to patients and animals, e.g., mammals, to obtain effective release of growth hormone.

The following examples are provided for the purpose of further illustration only and are not intended to be limitations on the disclosed invention.

EXAMPLE 1

3-Amino-3-methyl-N-[2,3,4,5-tetrahydro-2-[[2 '-[[(methylamino)carbonyl]amino][1,1'-biphenyl]-4-yl]methyl]-3-oxo-1H-2-benzazepin-4(R)-yl]butanamide, trifluoroacetate Step A: t-Butyl (2S,3R,5R)-5-(2-cyanobenzyl)-6-oxo-2,3-diphenyl-4-morpholine carboxylate To a stirred solution of 9.68 g (27.4 mmol) of t-butyl (2S,3R)-(+)-6-oxo-2,3-diphenyl-4-morpholine carboxylate (Aldrich Chemical Company) and 5.91 g (30.1 mmol, 1.1 eq) of α-bromo-o-tolunitrile in 140 mL of tetrahydrofuran at −78° C. was added dropwise 28.8 mL of a 1.0M THF solution of sodium hexamethyldisilazide (28.8 mmol) over 15 min. The mixture was stirred at −78° C. for 3 h, then quenched with saturated aqueous ammonium chloride, extracted with ethyl acetate (5×150 mL) and the combined organic extracts washed with water, saturated aqueous sodium chloride, dried over anhydrous magnesium sulfate, filtered and the filtrate concentrated under reduced pressure. Chromatography on silica gel (elution with 20% ethyl acetate-hexanes) gave the product as a white solid (8.01 g, 63%). $^1$H NMR indicates this compound exists as an approximately 5:1 mixture of rotamers. $^1$H NMR (400 MHz, CDCl$_3$): major rotamer—δ0.92 (s, 9H), 3.52 (dd; 10, 14 Hz; 1H), 3.62 (dd; 5, 14 Hz; 1H), 5.08 (d, 3 Hz, 1H), 5.40 (dd; 5, 10 Hz; 1H); 5.79 (d, 3 Hz, 1H), 6.52 (d, 8 Hz, 2H), 6.92 (d, 8 Hz, 2H), 7.00–7.70 (m, 1 OH). FAB-MS: calculated for $C_{29}H_{28}N_2O_4$ 468; found 469 (M+H,30%), 369 (M-BOC, 100%).

Step B: 4(R)-[[t-Butoxycarbonyl][(1R,2S)-1,2-diphenyl-2-hydroxyethyl]]amino-2,3,4,5-tetrahydro-1H-2-benzazepin-3-one To a stirred solution of 7.94 g (17.0 mmol) of t-butyl (2S,3 R,5R)-5-(2-cyanobenzyl)-6-oxo-2,3-diphenyl-4-morpholine carboxylate and 4.94 g (17.0 mmol) of cobalt (II) nitrate hexahydrate in methanol-THF (10:1=150 mL methanol and 15 mL THF) at room temperature was added solid sodium borohydride (6.42 g, 170 mmol) in ten approximately equal portions over 1 h (Caution: each addition is accompanied by vigorous effervescence!). The mixture was stirred at room temperature for 20 h and a further addition of sodium borohydride was made (3.41 g, 84.9 mmol) in five approximately equal portions. The mixture was stirred at ambient temperature for another 24 h then acidified with 2N HCl and concentrated under reduced pressure to remove most of the methanol. The residue was then basined with concentrated aqueous ammonium hydroxide then extracted with ethyl acetate (5×150 mL). The combined organic extracts were washed with water, saturated aqueous sodium chloride, dried over anhydrous magnesium sulfate, filtered and the filtrate concentrated under reduced pressure. Chromatography on silica gel (first by elution with 20% ethyl acetate-hexanes) gave 2.02 g of recovered starting material; further elution with 50–70% ethyl acetate-hexanes gave 4.02 g (50%) of the product as a white foam. $^1$H NMR indicates this compound exists as an approximately 1:1 mixture of rotamers in CDCl$_3$ at ambient temperature. $^1$H NMR (400 MHz, CDCl$_3$): δ1.60, 1.64 (2×s, total of 9H)*, 1.74, 1.83 (2×dd; 4, 15 Hz; total of 1H)*, 3.52, 3.64 (2×t, 15 Hz, total of 1H)*, 3.75–3.82 (m, 1H)*, 4.00–4.10 (m, 1H)*, 4.69, 4.90 (2×d, 15 Hz, total of 1H)*, 5.45–5.70 (m, 2H)*, 6.08, 6.18 (2×d, 8 Hz, total of 1H)*, 7.00–7.75 (m, 14H). *Two rotamers evident. FAB-MS calculated for $C_{29}H_{32}N_2O_4$ 472; found 473 (M+H, 38%), 373 (M-BOC, 100%).

Step C: 4-Methyl-2'-nitro-1,1'-biphenyl

A vigorously stirred mixture of 4-tolylboronic acid (34 g, 0.25 mol) and 2-bromo-1-nitrobenzene (34 g, 0.168 mol) in a mixture of 5N sodium hydroxide (170 mL), water (57 mL), isopropanol (215 mL) and benzene (1080 mL) under a nitrogen atmosphere was treated with (tetrakis)triphenylphosphine palladium (O) (11.9 g). The stirred bilayer reaction mixture was heated at reflux for 3 hours. The cooled reaction mixture was filtered through Celite and the filter cake washed with fresh benzene. The organic layer was separated and washed with water (3×), dried over magnesium sulfate and filtered. The filtrate was evaporated under vacuum and the residue (46.1 g) purified by preparative high pressure liquid chromatography on silica gel, eluting with hexane/ethyl acetate (20:1) gave 28.05 g of the product. EI-MS: calculated for $C_{13}H_{11}NO_2$ 213; found 213 (M+). $^1$H NMR (400 MHz, $CDCl_3$): δ2.38 (s, 3H), 7.20 (m, 4H), 7.43 (m, 2H), 7.59 (t, 1H), 7.8 (d, 1H).

Step D: 4-Bromomethyl-2'-nitro-1,1'-biphenyl

A solution of 4-methyl-2'-nitro-1,1'-biphenyl (6.0 g, 28.2 mmol), N-bromosuccinimide (4.99 g, 28.2 mmol) and AIBN (653 mg) in 75 mL of carbon tetrachloride was heated at reflux until a negative potassium iodide test was obtained (1.5 h). The reaction mixture was cooled and filtered. The filtrate was evaporated under vacuum to yield 8.41 g of crude product. $^1$H NMR revealed the product composition was approximatly 75% monobromo and 10% dibromo, in addition to 15% of unreacted starting material. $^1$H NMR (200 MHz, $CDCl_3$): δ4.53 (s, 2H), 7.2–7.7 (m, 7H), 7.85 (m, 1H). EI-MS: calculated for $C_{14}H_{10}BrN$ 272; found 272,274 (M+).

Step E: 4(R)-[[t-Butoxycarbonyl][(1R,2S)-1,2-diphenyl-2-hydroxyethyl]]amino-2,3,4,5-tetrahydro-2-[[(2'-nitro)[1,1'-biphenyl]-4-yl]methyl]-1H-2-benzazepin-3-one To a stirred solution of 195 mg, (0.413 mmol) of the intermediate obtained in Step B in 3 mL of dry dimethylformamide at 0° C. was added in one portion 18.2 mg of 60% dispersion of sodium hydride in mineral oil (0.454 mmol, 1.1 eq). The mixture was stirred for 1 h at room temperature, then cooled to 0° C. prior to the addition of 145 mg (0.496 mmol) of 4-bromomethyl-2'-nitro-1,1'-biphenyl in 1.0 mL of dry dimethylformamide. The mixture was stirred at room temperature for 5 h, then quenched with saturated aqueous ammonium chloride and extracted with ethyl acetate (5×10 mL). The combined organic extracts were washed with water, saturated aqueous sodium chloride, dried over anhydrous magnesium sulfate, filtered and the filtrate concentrated under reduced pressure. Chromatography on silica gel, eluting with 20% ethyl acetate-hexanes, gave 230 mg (82%) of the product as a white foam. $^1$H NMR indicates this intermediate exists as an approximately 2:1 mixture of rotamers in $CDCl_3$ at ambient temperature. $^1$H NMR (400 MHz, $CDCl_3$): δ1.53 and 1.66 (major) (2×s, total of 9H)*, 3.50 and 3.62 (major) (2×t, 15 Hz, total of 1H)*, 3.75 and 4.53 (2×d, 16 Hz, 2H) (major rotamer), 3.86 and 4.88 (2×d, 15 Hz, 2H) (minor rotamer), 4.15 and 5.15 (2×d, 15 Hz, 2H) (minor rotamer), 4.20 (dd, 6 Hz, 15 Hz, 1H)*, 5.12 and 5.20 (2×d, 15 Hz, total of 2H) (major rotamer), 5.46–5.75 (m, 2H)*, 6.70–7.90 (m, 23H). *Two rotamers evident. FAB-MS calculated for $C_{42}H_{41}N_3O_6$ 683; found 684 (M+H,20%), 584 (M-BOC,82%).

Step F: 4(R)-[[t-Butoxycarbonyl][(1R,2S)-1,2-diphenyl-2-hydroxyethyl]]amino-2,3,4,5-tetrahydro-2-[[2'-[(methylaminocarbonyl)amino][1,1'-biphenyl]-4-yl]methyl]-1H-2-benzazepin-3-one A stirred solution of 263 mg (0.385 mmol) of the intermediate obtained in Step E in methanol was catalytically hydrogenated at room temperature and 1 atmosphere in the presence of 50 mg of 5% platinum on carbon catalyst for 3 hours. The mixture was filtered through Celite and evaporated under reduced pressure. The crude product was dissolved in 4 mL of dichloromethane and treated with 0.5 mL of methyl isocyanate. The mixture was stirred at room temperature overnight, then quenched with 2 mL of methanol and evaporated under reduced pressure. Chromatography on silica gel, eluting with 50% ethyl acetate-hexanes, gave 260 mg (95%) of the product 7 as a white foam. $^1$H NMR indicates this intermediate exists as an approximately 3:1 mixture of rotamers in $CDCl_3$ at ambient temperature. Partial $^1$H NMR (400 MHz, $CDCl_3$): δ1.54 and 1.65 (major) (2×s, total of 9H)*, 2.68 and 2.70 (major) (2×d, 5 Hz, total of 3H)*. *Two rotamers evident. FAB-MS: calculated for $C_{44}H_{46}N_4O_5$ 710; found 711 (M+H,17%), 611 (M-BOC, 79%).

Step G: 4,4-Dimethylazetidin-2-one

A 3-neck 3 L round bottom flask equipped with a magnetic stirrer, thermometer, cold finger condenser and nitrogen bubbler was charged with 1 L of ether. The flask was cooled to −65° C. and into it was condensed 500–600 mL of isobutylene. The cold finger condenser was replaced with a dropping funnel and 200 mL (325 g, 2.30 mol) of chlorosulfonyl isocyanate was added dropwise over 1.5 hours. The mixture was maintained at −65° C. for 1.5 hours then the dry ice/acetone cooling bath replaced with methanol/ice and the internal temperature slowly increased to −5° C. At which time the reaction initiated and the internal temperature rose to 15° C. with evolution of gas. The internal temperature remained at 15° C. for several minutes then dropped back down to −5° C. and the mixture stirred at −5° C. for 1 hour. The methanol/ice bath was removed and the reaction mixture warmed to room temperature and stirred overnight.

The reaction mixture was transferred to a 3-neck 12 L round bottom flask fitted with a mechanical stirrer and diluted with 2 L of ether. The well stirred reaction mixture was treated with 2 L of saturated aqueous sodium sulfite. After 1 hour, an additional 1 L of saturated aqueous sodium sulfite was added followed by sufficient sodium bicarbonate to adjust the pH to approximately 7. The mixture was stirred another 30 minutes then the layers allowed to separate. The ether layer was removed and the aqueous layer reextracted with 2×1 L of ether. The combined ether extracts were washed once with 500 mL of saturated aqueous sodium bicarbonate and once with 500 mL of saturated aqueous sodium chloride. The ether layer was removed, dried over magnesium sulfate, filtered and concentrated under vacuum to give 33 g of a pale yellow oil. The aqueous layer was made basic by the addition of solid sodium bicarbonate and extracted with 3×1 L of ether. The combined ether extracts were washed and dried as described above, then combined with the original 33 g of pale yellow oil and concentrated under vacuum to give 67.7 g of product. Further extraction of the aqueous layer with 4×1 L of methylene chloride and washing and drying as before gave an additional 74.1 g of product. Still further extraction of the aqueous layer with 4×1 L of methylene chloride gave an additional 21.9 g of product. The combined product (163.7 g, 1.65 mol, 72%) was used in Step H without purification. $^1$H NMR (200 MHz, $CDCl_3$): δ1.45 (s, 6H), 2.75 (d, 3Hz, 2H), 5.9 (br s, 1H).

Step H: N-(t-Butoxycarbonyl)-4,4-dimethylazetidin-2-one

A 5 L, 3-neck round bottom flask equipped with a magnetic stirrer, thermometer, nitrogen bubbler and addition funnel was charged with 88.2 g (0.89 mol) of 4,4-dimethylazetidin-2-one (Step G), 800 mL of methylene chloride, 150 mL of triethylamine (1.08 mol) and 10.9 g (0.089 mol) of 4-dimethylaminopyridine. To the stirred solution, at room temperature was added dropwise over 15 minutes a solution of 235 g (1.077 mol) of di-t-butyl-dicarbonate in 300 mL of methylene chloride. The reaction mixture was stirred at room temperature overnight, then diluted with 1 L of methylene chloride and washed with 500 mL of saturated aqueous ammonium chloride, 500 mL of water, and 500 mL of saturated aqueous sodium chloride. The organic layer was separated, dried over magnesium sulfate, filtered and concentrated under vacuum to afford 180.3 g of crude product as an orange solid. The material was used directly in Step I without purification. ¹H NMR (200 MHz, CDCl₃): δ1.50 (s, 9H), 1.54 (s, 6H), 2.77 (s, 2H).

Step I: 3-t-Butoxycarbonylamino-3-methylbutanoic acid

A 3 L, 3-neck round bottom flask equipped with a magnetic stirrer, thermometer, nitrogen bubbler and addition funnel was charged with 180.3 g (0.89 mol) of N-(t-butoxycarbonyl)-4,4-dimethylazetidin-2-one dissolved in 1 L of tetrahydrofuran. The solution was cooled to 0°–5° C. and treated dropwise with 890 mL of 1.0M aqueous lithium hydroxide over 30 minutes. The reaction mixture was stirred at 0–5° C. for 2 hours, then diluted with 1 L of ether and 1 L of water. The layers were allowed to separate and the aqueous layer was reextracted with an additional 1 L of ether. The aqueous layer was acidified by the addition of 1 L of saturated aqueous sodium bisulfate, then extracted with 1×1 L and 2×500 mL of ether. The combined organic layer and ether extracts were washed with 500 mL of saturated aqueous sodium chloride, dried over magnesium sulfate and concentrated under vacuum to give 173 g of a yellow oil that solidified upon standing. The material was slurried with warm hexane, then filtered and dried under high vacuum to afford 168.5 g (0.775 mol, 87%) of product as a white solid. ¹H NMR (200 MHz, CDCl₃): δ1.39 (s, 6H), 1.44 (s, 9H), 2.72 (s, 2H). FAB-MS: calculated for $C_{10}H_{19}NO_4$ 217; found 218 (M+H,54%).

Step J: 3-Amino-3-methyl-N-[2,3,4,5-tetrahydro-2-[[2'-[[(methylamino)carbonyl]amino][1,1'-biphenyl]-4-yl]methyl]- 3-oxo-1H-2-benzazepin-4(R)-yl]butanamide, trifluoroacetate To a stirred solution of 160 mg (0.225 mmol) of the intermediate obtained in Step F in 3 mL of dichloromethane at room temperature was added 1 mL of trifluoroacetic acid. The mixture was stirred at room temperature for 2 h after which TLC analysis (75% ethyl acetate-hexanes) and subsequent analysis of the NMR of crude material indicated complete removal of the BOC protective group. The mixture was concentrated under reduced pressure and then dissolved in 2 mL of methanol and catalytically hydrogenated at room temperature and 40 psi in the presence of 100 mg of palladium (II) chloride for 41 hours. The mixture was filtered through Celite and the filtrate evaporated under reduced pressure to give the crude product (163 mg) as a white solid. Without purification, the crude product was dissolved in 3 mL of dichloromethane and treated with triethylamine (0.184 mL, 1.32 mmol), 3-t-butoxycarbonylamino-3-methylbutanoic acid (96 mg, 0.44 mmol) and benzotriazol-1-yloxytris(dimethylamino)-phosphonium hexafluorophosphate (282 mg, 0.638 mmol). The mixture was stirred at room temperature for 16 h, then diluted with 20 mL of ethyl acetate, washed with 1N HCl, water, saturated aqueous sodium chloride, dried over anhydrous magnesium sulfate, filtered and the filtrate concentrated under reduced pressure. The crude product was dissolved in 4 mL of dichloromethane and treated with 2 mL of trifluoroacetic acid. The mixture was stirred at room temperature for 2 h then evaporated under vacuum. Purification by reverse phase medium pressure liquid chromatography on C-8 eluting with methanol/0.1% aqueous trifluoroacetic acid (60:40) and combination and lyophilization of the pure fractions gave the title compound as a white solid (8 mg). ¹H NMR (400 MHz, CD₃OD): δ1.43 (s, 3H), 1.45 (s, 3H), 2.62 (d, 16 Hz, 1H), 2.66 (d, 16 Hz, 1H), 2.68 (s, 3H), 3.13 (dd; 16, 18 Hz; 1H), 3.35 (dd; 5, 18 Hz; 1H), 4.08 (d, 16 Hz, 1H), 4.60 (d, 15 Hz, 1H), 4.84 (d, 15 Hz, 1H), 5.27 (d, 16 Hz, 1H), 5.55 (dd; 5, 16 Hz; 1H), 6.96–7.32 (m, 11H), 7.64 (d, 8 Hz, 1H). FAB-MS: calculated for $C_{30}H_{35}N_5O_3$ 513; found 514 (M+H, 100%).

EXAMPLE 2

2-Amino-2-methyl-N-[2,3,4,5-tetrahydro-2-[[2'-[[(methylamino)carbonyl]amino][1,1'-biphenyl]-4-yl]methyl]-3-oxo-1 H-2-benzazepin-4(R)-yl]propanamide, trifluoroacetate The title compound was prepared from N-BOC-α-methylalanine and 4(R)-[[t-butoxycarbonyl][(1R,2S)-1,2-diphenyl- 2-hydroxyethyl]]amino-2,3,4,5-tetrahydro-2-[[2'-[(methylaminocarbonyl)amino]-[1,1'-biphenyl]-4-yl]methyl]-1H-2-benzazepin-3-one (Example 1, Step F) by the procedures described in Example 1. ¹H NMR (400 MHz, CD₃OD): δ1.65 (s, 3H), 1.70 (s, 3H), 2.67 (s, 3H), 3.15–3.38 (m, 2H), 4.09 (d, 16 Hz, 1H), 4.57 (d, 15 Hz, 1H), 4.85 (d, 15 Hz, 1H), 5.25 (d, 16 Hz, 1H), 5.52 (dd; 6, 15 Hz; 1H), 6.98–7.90 (m, 12H ). FAB-MS: calculated for $C_{29}H_{33}N_5O_3$ 499; found 500 (M+H, 100%).

EXAMPLE 3

2-Amino-2-methyl-N-[2,3,4,5-tetrahydro-2-[[2'-[[[(methylamino)carbonyl]amino]methyl][1,1'-biphenyl]-4-yl]methyl]-3-oxo-1 H-2-benzazepin-4(R)-yl]propanamide, trifluoroacetate Step A: 4-Bromobenzyl-t-butyldiphenylsilyl ether To a solution of 28.2 g (0.150 mol) of 4-bromobenzyl alcohol in 470 mL of dry dimethylformamide under nitrogen atmosphere was added 31.4 mL (0.225 mol) of triethylamine. The reaction mixture was cooled to 0° C. and 43 mL (0.17 mol) of t-butylchlorodiphenylsilane was added dropwise by addition funnel. The reaction mixture was stirred at ambient temperature overnight then poured into a separatory funnel containing 1 L of diethyl ether and 500 mL of water. To this mixture was added 125 mL of 2N aqueous hydrochloric acid. The layers were separated and the aqueous layer was extracted with diethyl ether (2×350 mL). The organic extracts were combined, washed with water (2×250 mL) and dried over magnesium sulfate. The solids were removed by filtration and the solvent removed under vacuum to give an oil which crystallized on standing. The flask containing the crude product was placed in the freezer overnight then triturated with a minimal amount of methanol and filtered. The solid was air dried for several hours then dried under vaccuum overnight to afford 59.5 g (93%) of product as an off-white solid (mp 44°–47° C.). ¹H NMR (200 MHz, CDCl₃): δ1.15 (s, 9H), 4.76 (s, 2H), 7.25 (d, 8 Hz, 2H), 7.45 (m, 8H), 7.75 (m, 4H). FAB-MS: calculated for $C_{23}H_{25}BrOSi$ 424; found 425 (M+H, 7%).

Step B: 4-(t-Butyldiphenylsiloxymethyl)phenylboronic acid

To a solution of 20 g (47 mmol) of 4-bromobenzyl-t-butyldiphenyl silyl ether (Step A) in 200 mL of dry tetrahydrofuran under a nitrogen atmosphere at –78° C. was added dropwise by syringe 19.74 mL (49.35 mmol) of a 2.5M solution of n-butyllithium in hexanes over twenty minutes. The resulting mixture was stirred for thirty minutes, then 11.6 mL (50.3 mmol) of triisopropyl borate was added by syringe. The reaction mixture was stirred at –78° C. for thirty minutes then slowly warmed to room temperature and stirred for an additional two hours. The reaction mixture was then quenched by the addition of 750 mL of water containing 100 mL of concentrated hydrochloric acid and 500 mL of diethyl ether. The mixture was stirred for one hour and then the organic layer was separated. The aqueous layer was extracted with diethyl ether (2×400 mL). The combined ether extracts were washed with saturated aqueous sodium chloride (4×100 mL), dried over magnesium sulfate and filtered. The solvent was removed under vacuum to give an oil which was crystallized by dissolving in hexanes and evaporation of the solvent under vacuum to afford 15.6 g (85%) of product as a whim solid (mp 171°–174° C.). $^1$H NMR (200 MHz, CDCl$_3$): δ1.11 (s, 9H), 4.86 (s, 2H), 7.40 (m, 6H), 7.58 (d, 8Hz, 2H), 7.70 (m, 4H), 8.22 (d, 8Hz, 2H). FAB-MS: calculated for $C_{23}H_{27}BrO_3Si$ 390; found 372 (M-H$_2$O).

Step C: N-(t-Butoxycarbonyl)-2-bromobenzylamine

To a slurry of 8.88 g (39.9 mmol) of 2-bromobenzylamine hydrochloride in 100 mL of dry methylene chloride under a nitrogen atmosphere was added by syringe 12.24 mL (87.80 mmol) of triethylamine. The resulting solution was stirred at 0° C. for five minutes then treated with 9.6 g (44 mmol) of di-t-butyldicarbonate. The reaction was stirred at room temperature for two hours then diluted with 350 mL of methylene chloride., The solution was washed with water (2×150 mL), saturated aqueous ammonium chloride (150 mL), saturated aqueous sodium bicarbonate (4×150 mL) and saturated aqueous sodium chloride (150 mL), dried over sodium sulfate and filtered. The solvent was removed under vacuum to give an oil which was crystallized by dissolving in hot hexanes, filtering and cooling the solution. The product was filtered and dried under vacuum to afford 8.66 g (90%) of the product as a white solid (mp 51°–53° C.). $^1$H NMR (200 MHz, CDCl$_3$): δ1.41 (s, 9H), 4.37 (d, 5Hz, 2H), 5.00 (s, 1H), 7.10 (m, 1H), 7.25 (m, 1H), 7.35 (m, 1H), 7.40 (d, 6Hz, 1H). FAB-MS: calculated for $C_{12}H_{16}BrNO_2$ 285; found 286 (M+H).

Step D: 2'-[(t-Butoxycarbonylamino)methyl]-4-[(t-butyldiphenylsiloxy)methyl]-1,1'-biphenyl To a solution of 3.2 g (8.2 mmol) of 4-(t-butyldiphenylsilyoxymethyl)phenylboronic acid (Step B) in 64 mL of benzene was added 2.2 mL of water, 6.4 mL of 5N aqueous sodium hydroxide, and 8.3 mL of isopropanol. To this mixture was added 180 mg (0.16 mmol) of tetrakis(triphenylphosphine) palladium and 2.20 g (7.81 mmol) of N-(t-butoxycarbonyl)-2-bromobenzylamine (Step C). The resulting mixture was heated under nitrogen at reflux for 2 hours then cooled to room temperature. The reaction mixture was diluted with 100 mL of water, transferred to a separatory funnel and extracted with is ether (3×150 mL). The combined ether extracts were washed with saturated aqueous sodium bicarbonate (100 mL) and saturated aqueous sodium chloride (100 mL), dried over magnesium sulfate and filtered. The solvent was removed under vacuum to give a crude product which was purified by column chromatography on silica gel eluting with hexanes/ethyl acetate (9:1) to afford 4.31 g (100%) of the product as a clear oil. $^1$H NMR (200 MHz, CDCl$_3$): δ1.11 (s, 9H), 1.41 (s, 9H), 4.27 (d, 6Hz, 2H), 4.45 (m, 1H), 4.81 (s, 2H), 7.20–7.49 (m, 14H), 8.72 (m, 4H). FAB-MS: calculated for $C_{35}H_{41}NO_3Si$ 551; found 552 (M+H).

Step E: 2'-[(t-Butoxycarbonylamino)methyl]-1,1'-biphenyl- 4-methanol

To a solution of 3.85 g (7.00 mmol) of 2'-[(t-butoxycarbonylamino)methyl]-4-[(t-butyldiphenylsiloxy)methyl]-1,1'-biphenyl (Step D) in 25 mL of dry tetrahydrofuran under a nitrogen atmosphere was added by syringe 10.5 mL (0.530 mmol) of a 1.0M solution of tetra-n-butylammonium fluoride in tetrahydrofuran. The reaction mixture was stirred for two hours then diluted with 700 mL of diethyl ether. The mixture was washed with water (3×150 mL), saturated aqueous sodium bicarbonate (50 mL), saturated aqueous sodium chloride (50 mL), then dried over magnesium sulfate and filtered. The solvent was removed under vacuum to give an oil which was purified by column chromatography on silica gel eluting with hexanes/ethyl acetate (55:45) to afford 2.02 g (92%) of the product as a white solid (mp 89°–93° C.). $^1$H NMR (200 MHz, CDCl$_3$): δ1.40 (s, 9H), 2.50 (s, 2H), 4.20 (s, 2H), 4.70 (s, 2H), 7.18–7.45 (m, 8H). FAB-MS: calculated for $C_{19}H_{23}NO_3$ 313; found 314 (M+H).

Step F: 2'-[(t-Butoxycarbonylamino)methyl]-1,1'-biphenyl- 4-methanol, methanesulfonate ester To solution of 53 mg (0.17 mmol) of 2'-[(t-butoxycarbonylamino)methyl]-1,1'-biphenyl-4-methanol (Step E) in 1 mL of dry methylene chloride under nitrogen atmosphere at 0° C. was added by syringe 0.035 mL (0.25 mmol) of triethylamine followed by 0.016 mL (0.20 mmol) of methanesulfonyl chloride. The reaction mixture was stirred for 2 hours at 0° C. then diluted with 75 mL of methylene chloride, washed with water, saturated aqueous sodium bicarbonate, saturated aqueous sodium chloride, dried over sodium sulfate and filtered. The solvent was removed under vacuum to give 61 mg (97%) of the product as a white solid which was used in the next step without further purification. $^1$H NMR (200 MHz, CDCl$_3$): δ1.38 (s, 9H), 2.95 (s, 3H), 4.20 (d, 5Hz, 2H), 4.65 (s, 1H), 5.25 (s, 2H), 7.18–7.50 (m, 8H). FAB-MS: calculated for $C_{20}H_{25}NO_5S$ 391; found 392 (M+H).

Step G: 4(R)-Amino-2,3,4,5-tetrahydro-1H-2-benzazepin-3-one

A solution of 478 mg (1.01 mmol) of 4(R)-[[t-butoxycarbonyl][(1R,2S)-1,2-diphenyl-2-hydroxyethyl]]amino- 2,3,4, 5-tetrahydro-1H-2-benzazepin-3-one (Example 1, Step B) in 5 mL of methylene chloride at room temperature was treated with 0.5 mL of trifluoroacetic acid. The mixture was stired at room temperature for 3 hours then all volatiles removed under vacuum. The residue was dissolved in 5 mL of water and the solution made basic (pH 10–11) by the addition of solid sodium carbonate. The mixture was extracted with chloroform (5×) and the combined extracts dried over anhydrous potassium carbonate, filtered and solvents removed under vacuum to give 372 mg (1.00 mmol, 99%) of 4(R)-[[(1R,2S)-1,2-diphenyl- 2-hydroxyethyl]]amino-2,3,4,5-tetrahydro-1H-2-benzazepin-3-one which was used in the next step without purification.

A solution of 372 mg (1.00 mmol) of the intermediate obtained above in 30 mL of ethanol was hydrogenated at 40 psi and ambient temperature in the presence of 1.0 g of palladium (II) chloride for 100 hours. The mixture was filtered through Celite and solvent removed under vacuum to give the product. $^1$H NMR (400 MHz, CDCl$_3$): δ2.97 (dd; 10, 16 Hz; 1H), 3.20 (dd; 6, 16 Hz; 1H), 4.07 (d, 16 Hz, 1H), 4.18 (dd; 6, 10 Hz; 1H), 4.73 (d, 16 Hz, 1H), 7.17 (m, 4H).

Step H: 4(R)-Benzyloxycarbonylamino-2,3,4,5-tetrahydro-1 H-2-benzazepin-3-one

A solution of 210 mg (1.19 mmol) of 4(R)-amino-2,3,4, 5-tetrahydro- 1H-2-benzazepin-3-one in 5 mL of tetrahydrofuran was treated with 5 mL of 10% aqueous potassium carbonate followed by 0.20 mL (0.24 g, 1.3 mmol, 1.1 eq) of 95% benzyl chloroformate. The mixture was stirred vigorously at room temperature for 6 hours then diluted with 20 mL of ether and the mixture transferred to a separatory funnel. The lower aqueous layer was removed and washed with several portions of ether. The combined ether washes and ether layer were washed, with saturated aqueous sodium chloride, dried over magnesium sulfate, filtered and solvents removed under vacuum to give 365 mg (1.14 mmol, 96%) of the product. $^1$H NMR (400 MHz, CDCl$_3$): δ3.08 (dd; 12, 16 Hz; 1H), 3.27 (dd; 7, 16 Hz; 1H), 4.06 (d, 16 Hz, 1H), 4.75 (d, 16 Hz, 1H), 5.00 (dd; 7, 12 Hz; 1H), 5.12 (s, 2H), 7.1–7.4 (m, 9H).

Step I: 4(R)-Benzyloxycarbonylamino-2,3,4,5-tetrahydro-2-[[2'-[[(t-butoxycarbonyl)amino]methyl][1,1'-biphenyl]- 4-yl]-methyl]-1H-2-benzazepin-3-one Prepared from 4(R)-benzyloxycarbonylamino-2,3,4,5-tetrahydro-1 H-2-benzazepin-3-one (Step H) and 2'-[(t-butoxycarbonylamino)methyl]-1,1'-biphenyl-4-methanol, methanesulfonate ester (Step F) by the procedure described in Example 1, Step E. $^1$H NMR (400 MHz, CDCl$_3$): δ1.40 (s, 9H), 3.02 (dd; 12, 16 Hz; 1H), 3.55 (dd; 5, 16 Hz; 1H), 3.87 (d, 18 Hz, 1H), 4.18 (d, 6 Hz, 2H), 4.43 (d, 15 Hz, 1H), 4.60 (br t, 6 Hz, 1H), 4.95 (d, 15 Hz, 1H), 5.07 (d, 18 Hz, 1H), 5.13 (s, 2H), 5.29 (dd; 5, 12 Hz; 1H), 6.25 (d, 6 Hz, 1H), 6.87 (d, 8 Hz, 1H), 7.04 (t, 8 Hz, 1H), 7.10 (d, 8 Hz, 1H), 7.13–7.45 (m, 14 H). FAB-MS: calculated for C$_{37}$H$_{39}$N$_3$O$_5$ 605; found 612 (M+Li,100%).

Step J: 4(R)-Benzyloxycarbonylamino-2,3,4,5-tetrahydro-2-[[2'-[[(methylamino)carbonyl]amino][1,1'-biphenyl]-4-yl]-methyl]-1H-2-benzazepin-3-one A solution of 400 mg (0.79 mmol) of the intermediate obtained in Step I in 6 mL of methylene chloride was treated with 2 mL of trifluoroacetic acid and the resulting solution stirred at room temperature for 3 hours. All volatiles were removed under vacuum and the residue redissolved in 5 mL of methylene chloride and treated with 0.56 mL of triethylamine and 0.3 mL of methyl isocyanate. The mixture was stirred at room temperature, for 2 hours then all volatiles removed under vacuum and the residue taken up in ethyl acetate and washed with 2N aqueous hydrochloric acid, saturated aqueous sodium bicarbonate and saturated aqueous sodium chloride. The organic layer was removed, dried over magnesium sulfate and the residue chromatographed on silica, eluting with ethyl acetate/hexanes (3:1) to give the product a colorless solid. $^1$H NMR (400 MHz, CDCl$_3$): δ2.70 (s, 3H), 3.01 (dd; 12, 16 Hz; 1H), 3.54 (dd; 5, 16 Hz; 1H), 3.87 (d, 18 Hz, 1H), 4.26 (s,2H), 4.39 (d, 15 Hz, 1H), 4.97 (d, 15 Hz, 1H), 5.07 (d, 18 Hz, 1H), 5.13 (s; 2H), 5.30 (dd; 5, 12 Hz; 1H), 6.24 (d, 6 Hz, 1H), 6.88 (d, 8 Hz, 1H), 7.04'(t, 8 Hz, 1H), 7.10 (d, 8 Hz, 1H), 7.15–7.40 (m, 13H), 7.45 (d, 8 Hz, 1H). FAB-MS: calculated for C$_{34}$H$_{34}$N$_4$O$_4$ 562; found 563 (M+H,100%).

Step K: 4(R)-Amino-2,3,4,5-tetrahydro-2-[[2'-[[(methylamino)carbonyl]amino][1,1'-biphenyl-4-yl]methyl]-1 H-2-benzazepin-3-one A solution of 310 mg (0.552 mmol) of the intermediate obtained in Step J in 5 mL of ethanol with 0.1 mL of trifluoroacetic acid was hydrogenated at 40 psi and ambient temperature in the presence of 100 mg of 10% palladium on carbon for 4 hours. The mixture was filtered through Celite and solvent removed under vacuum to give the product. $^1$H NMR (400 MHz, CD$_3$OD): δ2.69 (s, 3H), 3.24 (m, 1H), 3.44 (dd; 6, 16 Hz; 1H), 4.11 (s, 2H), 4.13 (d, 17 Hz, 1H), 4.68 (d, 14 Hz, 1H), 4.86 (d, 14 Hz, 1H), 5.14 (d, 17 Hz, 1H), 5.18 (d, 17 Hz, 1H), 6.95 (d, 8 Hz, 1H), 7.07 (t, 8 Hz, 1H), 7.15–7.25 (m, 5H), 7.28 (m, 1H), 7.28 (d, 8 Hz, 2H), 7.33 (t, 8 Hz, 1H), 7.38 (d, 8 Hz, 1H).

Step L: 2-t-Butoxycarbonylamino-2-methyl-N-[2,3,4,5-tetrahydro-2-[[2'-[[[(methylamino)carbonyl]amino]methyl] [1,1 '-biphenyl]-4-yl]methyl]-3-oxo- 1H-2-benzazepin-4 (R)-yl]-propanamide A solution of 158 mg (0.37 mmol) of the intermediate obtained in Step K in 2.5 mL of methylene chloride and 0.5 mL of dimethylformamide was treated with 112 mg (0.55 mmol, 1.5 eq) of N-t-butoxycarbonyl-2-methylalanine, 0.21 mL of triethylamine ( 149 mg, 1.48 mmol, 4 eq.), and 261 mg (0.59 mmol, 1.6 eq) of benzotriazol-1-yloxytris(dimethylamino)phosphonium hexafluorophosphate. The mixture was stirred at room temperature for 2 hours, then diluted with 20 mL of ethyl acetate and washed three times with 5% aqueous citric acid, twice with saturated aqueous sodium bicarbonate and once with saturated aqueous sodium chloride. The organic layer was removed, dried over magnesium sulfate, filtered and the filtrate concentrated under vacuum. The residue was purified by silica gel chromatography on silica, eluting with methylene chloride/methanol/ammonium hydroxide (96:3.5:0.5), to afford 250 mg (0.41 mmol, 111%) of the product as a white solid, contaminated with residual solvent. FAB-MS: calculated for C$_{35}$H$_{43}$N$_5$O$_5$ 613; found 614 (M+H,25%), 514 (M-BOC, 100%).

Step M: 2-Amino-2-methyl-N-[2,3,4,5-tetrahydro-2-[[2'-[[[(methylamino)carbonyl]amino]methyl][1,1'-biphenyl]-4-yl]methyl]-3-oxo-1H-2-benzazepin-4(R)-yl]propanamide, trifluoroacetate.

A solution of 250 mg of the intermediate obtained in Step L in 3 mL of methylene chloride was treated with 1 mL of trifluoroacetic acid and the resulting solution stirred at room temperature for 3 hours. All volatiles were removed under vacuum and the residue purified by reverse phase medium pressure liquid chromatography on C-8 eluting with methanol/0.1% aqueous trifluoroacetic acid (60:40) and combination and lyophilization of the pure fractions gave the title compound as a white solid (100 mg). $^1$H NMR (400 MHz, CD3OD): δ1.66 (s, 3H), 1.70 (s, 3H), 2.69 (s, 3H), 3.2 (m, 2H), 4.11 (d, 17 Hz, 1H), 4.13 (s, 2H), 4.70 (d, 14 Hz, 1H), 4.78 (d, 14 Hz, 1H), 5.27 (d, 17 Hz, 1H), 5.53 (dd; 6,14 Hz; 1H), 6.95 (d, 8 Hz, 1H), 7.04 (t, 8 Hz, 1H), 7.12 (d, 8 Hz, 1H), 7.18 (m, 5H), 7.26 (m, 1H), 7.26 (d, 8 Hz, 2H), 7.33 (t, 8 Hz, 1H), 7.38 (d, 8 Hz, 1H). FAB-MS: calculated for C$_{30}$H$_{35}$N$_5$O$_3$ 513; found 514 (M+H,100%).

EXAMPLE 4

3-Amino-3-methyl-N-[2,3,4,5-tetrahydro-2-[[2'-[[[(methylamino)carbonyl]amino]methyl][1,1'-biphenyl]-4-yl]methyl]-3-oxo-1H- 2-benzazepin-4(R)-yl]butanamide, trifluoroacetate The title compound was prepared from 4(R)-amino-2,3, 4,5-tetrahydro-2-[[2'-[[(methylamino)carbonyl]amino][1,1 '-biphenyl]-4-yl]methyl]-1H-2-benzazepin-3-one (Example 3, Step K) and 3-t-butoxycarbonylamino-3-methylbutanoic acid (Example 1, Step I) by the procedures described in Example 3, Steps L and M. $^1$H NMR (400 MHz, CD$_3$OD): δ1.44 (s, 3H), 1.45 (s, 3H), 2.64 (d, 7 Hz, 2H), 2.70 (s, 3H), 3.12 (m, 1H), 3.33 (m, 1H), 4.10 (d, 17 Hz, 1H), 4.12 (s, 2H), 4.67 (d, 14 Hz, 1H), 4.82 (d, 14 Hz, 1H), 5.27 (d, 17 Hz, 1H), 5.56 (dd; 6,14 Hz; 1H), 6.93 (d, 8 Hz, 1H), 7.03 (t, 8 Hz, 1H), 7.13 (m, 5H), 7.26 (d, 8 Hz, 2H), 7.28 (m, 1H), 7.32 (t, 8 Hz, 1H), 7.38 (d, 8 Hz, 1H). FAB-MS: calculated for C$_{31}$H$_{37}$N$_5$O$_3$ 527; found 528 (M+H,2%).

EXAMPLE 5

Utilizing the procedures described in Examples 1 to 4 and general methods of organic synthesis described in the chemical literature and familiar to one skilled in the art, the following compounds of Formula 1 can be prepared from the appropriately substituted starting materials and reagents.

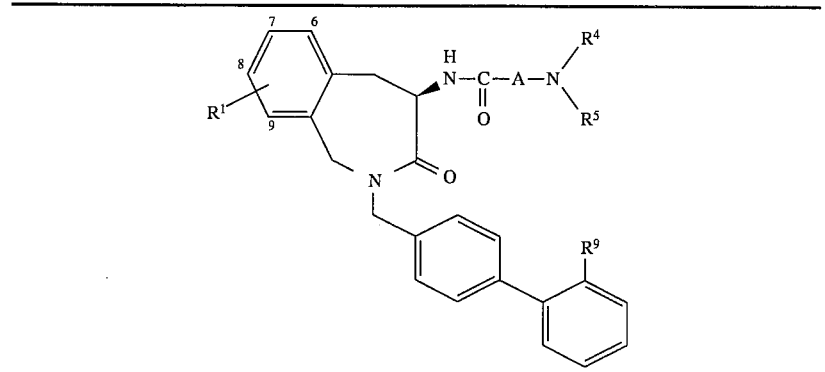
| R¹ | R⁹ | A | R⁴ | R⁵ |
|---|---|---|---|---|
| H | tetrazol-5-yl-NH | -CH₂-C(CH₃)₂- | -CH₂-CH(OH)-CH(OH)-CH₂OH | H |
| H | tetrazol-5-yl-NH | -CH₂-C(CH₃)₂- | -CH₂CH₂OH | H |
| H | tetrazol-5-yl-NH | -CH₂-C(CH₃)₂- | -CH₂C(OH)(CH₃)₂ | H |
| H | tetrazol-5-yl-NH | -CH₂-C(CH₃)₂- | -CH₂CH₂CH(OH)CH₃ | H |
| H | tetrazol-5-yl-NH | -CH₂-C(CH₃)₂- | -CH₂-C₆H₅ | H |
| H | tetrazol-5-yl-NH | -CH₂-C(CH₃)₂- | -CH₂CH₂CH₃ | H |
| H | tetrazol-5-yl-NH | -CH₂-C(CH₃)₂- | -CH₂-CH(OH)-CH₃ | H |
| 6-F | tetrazol-5-yl-NH | -CH₂-C(CH₃)₂- | H | H |
| 7-F | tetrazol-5-yl-NH | -CH₂-C(CH₃)₂- | H | H |

-continued

[Structure: benzazepinone core with R¹ substituent on fused benzene (positions 6,7,8,9), α-carbon bearing NH-C(=O)-A-N(R⁴)(R⁵), and N-CH₂-biphenyl with R⁹ substituent]

| R¹ | R⁹ | A | R⁴ | R⁵ |
|---|---|---|---|---|
| 7-CF₃ | tetrazole (NH) | -CH₂-C(CH₃)(CH₃)- | H | H |
| 7-OCH₃ | tetrazole (NH) | -CH₂-C(CH₃)(CH₃)- | H | H |
| 7-OH | tetrazole (NH) | -CH₂-C(CH₃)(CH₃)- | H | H |
| 7-SCH₃ | tetrazole (NH) | -CH₂-C(CH₃)(CH₃)- | H | H |
| 7-S(O)CH₃ | tetrazole (NH) | -CH₂-C(CH₃)(CH₃)- | H | H |
| 8-OCH₃ | tetrazole (NH) | -CH₂-C(CH₃)(CH₃)- | H | H |
| 8-F | tetrazole (NH) | -CH₂-C(CH₃)(CH₃)- | H | H |
| 8-Cl | tetrazole (NH) | -CH₂-C(CH₃)(CH₃)- | H | H |

-continued
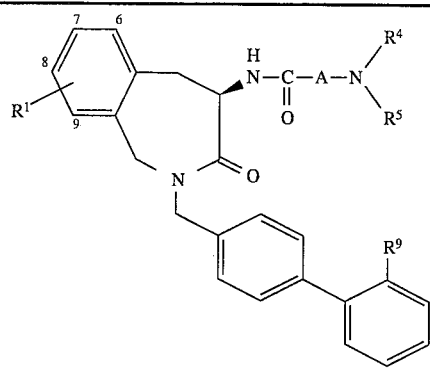
| R¹ | R⁹ | A | R⁴ | R⁵ |
|---|---|---|---|---|
| 8-I | tetrazole | —CH₂—C(CH₃)(CH₃)— | H | H |
| H | tetrazole | —C(CH₃)(CH₃)— | H | H |
| H | tetrazole | —C(H)(CH₃)— (S) | H | H |
| H | tetrazole | —C(CH₃)(H)— (R) | H | H |
| H | tetrazole | —C(H)(CH₂OH)— | H | H |
| H | tetrazole | —C(CH₃)(CH₂OH)— | H | H |
| H | tetrazole | —C(H)(CH₃)— | CH₃ | H |
| H | tetrazole | —CH₂—C(CH₃)(CH₂OH)— | H | H |
| H | tetrazole | —CH₂—C(HOCH₂)(CH₃)— | H | H |

-continued
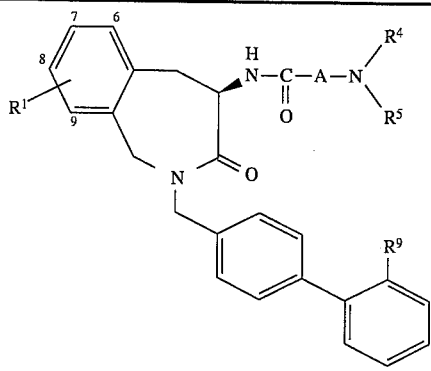
| R¹ | R⁹ | A | R⁴ | R⁵ |
|---|---|---|---|---|
| H | 5-tetrazolyl(NH) | −CH₂−C(HOCH₂)(CH₃)− | −CH₂CH(OH)CH₃ | H |
| H | 5-tetrazolyl(NH) | −CH₂−C(HOCH₂)(CH₃)− | −CH₂CH(OH)CH₂OH | H |
| H | 5-tetrazolyl(NH) | −C(H)(CH₂−phenyl)− | H | H |
| H | 5-tetrazolyl(NH) | −C(H)(CH₂−indol-3-yl)− | H | H |
| H | 5-tetrazolyl(NH) | −C(H)(CH₂−imidazol-4-yl)− | H | H |
| H | 5-tetrazolyl(NH) | 4-piperidinyl (NH) | — | — |
| H | 5-tetrazolyl(NH) | 3-piperidinyl (NH) | — | — |
| H | 5-tetrazolyl(NH) | quinuclidin-3-yl | — | — |

EXAMPLE 6

Utilizing the procedures described in Examples 1 to 4 and general methods of organic synthesis described in the chemical literature and familiar to one skilled in the art, the following compounds of Formula 1 can be prepared from the appropriately substituted starting materials and reagents.

| $R^1$ | $R^9$ | A | $R^4$ |
|---|---|---|---|
| H | tetrazol-5-yl (NH) | -C(CH$_3$)$_2$- | -CH$_2$-phenyl |
| H | tetrazol-5-yl (NH) | -CH$_2$-C(CH$_3$)$_2$- | -CH$_2$-CH(OH)-CH$_2$OH |
| 7-F | tetrazol-5-yl (NH) | -C(CH$_3$)$_2$- | -CH$_2$-phenyl |
| 7-F | tetrazol-5-yl (NH) | -CH$_2$-C(CH$_3$)$_2$- | -CH$_2$-CH(OH)-CH$_2$OH |
| H | -C(O)-NHCH$_3$ | -C(CH$_3$)$_2$- | -CH$_2$-phenyl |
| H | -C(O)-NHCH$_3$ | -CH$_2$-C(CH$_3$)$_2$- | -CH$_2$-CH(OH)-CH$_3$ |
| 7-F | -C(O)-NHCH$_3$ | -C(CH$_3$)$_2$- | -CH$_2$-phenyl |
| H | -C(O)-NHCH$_3$ | -CH$_2$-C(CH$_3$)$_2$- | -CH$_2$-CH(OH)-CH$_2$OH |
| 7-F | tetrazol-5-yl (NH) | -C(CH$_3$)(H)- | H |

-continued
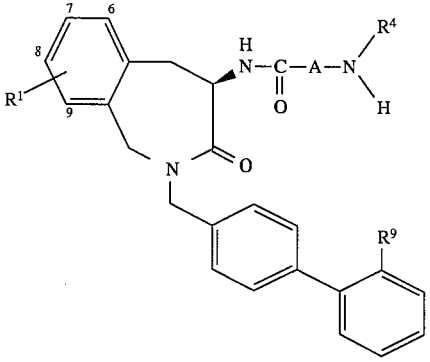
| R¹ | R⁹ | A | R⁴ |
|---|---|---|---|
| 7-F | 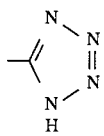 | 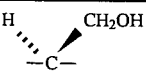 H, CH₂OH | H |
| 7-F | 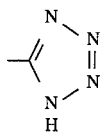 | 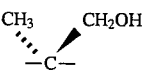 CH₃, CH₂OH | H |
| H |  -C(O)-NHCH₃ | 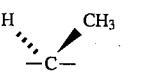 H, CH₃ | H |
| H |  -C(O)-NHCH₃ | 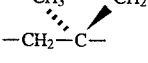 CH₃, CH₂OH, -CH₂-C- | H |
| H |  -C(O)-NHCH₃ | 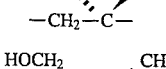 HOCH₂, CH₃, -CH₂-C- | H |
| H |  -C(O)-NHCH₃ | 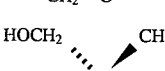 HOCH₂, CH₃, -CH₂-C- | H |
| H |  -C(O)-NHCH₃ | 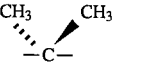 HOCH₂, CH₃, -CH₂-C- | H |
| H | 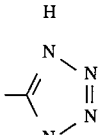 | 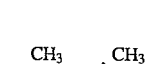 CH₃, CH₃ | 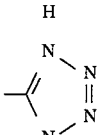 -CH₂-Ph |
| H | 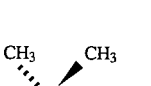 | CH₃, CH₃, -CH₂-C- | OH, -CH₂-CH-CH₂OH |
| 7-F | 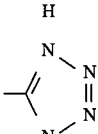 | CH₃, CH₃, -C- | 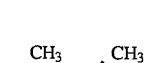 -CH₂-Ph |
| 7-F |  | CH₃, CH₃, -CH₂-C- | OH, -CH₂-CH-CH₂OH |

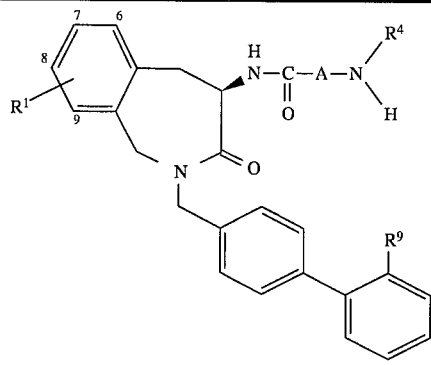

| R¹ | R⁹ | A | R⁴ |
|---|---|---|---|
| H | −C(=O)−NHCH₃ | −C(CH₃)(CH₃)− | −CH₂−C₆H₅ |
| H | −C(=O)−NHCH₃ | −CH₂−C(CH₃)(CH₃)− | −CH₂−CH(OH)−CH₃ |
| 7-F | −C(=O)−NHCH₃ | −C(CH₃)(CH₃)− | −CH₂−C₆H₅ |
| H | −C(=O)−NHCH₃ | −CH₂−C(CH₃)(CH₃)− | −CH₂−CH(OH)−CH₂OH |
| H | −NH−C(=O)−NHCH₃ | −C(CH₃)(CH₃)− | H |
| H | −NH−C(=O)−NHCH₃ | −CH₂−C(CH₃)(CH₃)− | −CH₂−CH(OH)−CH₃ |
| 7-F | −NH−C(=O)−NHCH₃ | −C(CH₃)(CH₃)− | H |
| H | −NH−C(=O)−NHCH₃ | −CH₂−C(CH₃)(CH₃)− | −CH₂−CH(OH)−CH₂OH |
| H | −CH₂NH−C(=O)−NHCH₃ | −C(CH₃)(CH₃)− | H |
| H | −CH₂NH−C(=O)−NHCH₃ | −CH₂−C(CH₃)(CH₃)− | −CH₂−CH(OH)−CH₃ |
| 7-F | −CH₂NH−C(=O)−NHCH₃ | −C(CH₃)(CH₃)− | H |
| H | −CH₂NH−C(=O)−NHCH₃ | −CH₂−C(CH₃)(CH₃)− | −CH₂−CH(OH)−CH₂OH |

EXAMPLE 7

Utilizing the procedures described in Examples 1 to 4 and general methods of organic synthesis described in the chemical literature and familiar to one skilled in the art, the following compounds of Formula 1 can be prepared from the appropriately substituted starting materials and reagents.

| R¹ | R⁹ | A | R⁴ | R⁵ |
|---|---|---|---|---|
| H | tetrazole-NH | $-CH_2-C(CH_3)_2-$ | $-CH_2-CH(OH)-CH(OH)-CH_2OH$ | H |
| H | tetrazole-NH | $-CH_2-C(CH_3)_2-$ | $-CH_2CH_2OH$ | H |
| H | tetrazole-NH | $-CH_2-C(CH_3)_2-$ | $-CH_2C(OH)(CH_3)_2$ | H |
| H | tetrazole-NH | $-CH_2-C(CH_3)_2-$ | $-CH_2CH_2CH(OH)CH_3$ | H |
| H | tetrazole-NH | $-CH_2-C(CH_3)_2-$ | $-CH_2$-phenyl | H |
| H | tetrazole-NH | $-CH_2-C(CH_3)_2-$ | $-CH_2CH_2CH_3$ | H |
| H | tetrazole-NH | $-CH_2-C(CH_3)_2-$ | $-CH_2-CH(OH)-CH_3$ | H |
| 7-F | tetrazole-NH | $-CH_2-C(CH_3)_2-$ | H | H |
| 8-F | tetrazole-NH | $-CH_2-C(CH_3)_2-$ | H | H |

-continued

[Structure: benzothiepine core with R¹ substituent at position 6/7, sulfur at position 2 connected to CH(CH₃)-NH-C(O)-A-N(R⁴)(R⁵), and N-CH₂-biphenyl-R⁹ group; positions 7, 8, 9 labeled on aromatic ring]

| R¹ | R⁹ | A | R⁴ | R⁵ |
|---|---|---|---|---|
| 8-CF₃ | tetrazole-NH | -CH₂-C(CH₃)₂- | H | |
| 8-OCH₃ | tetrazole-NH | -CH₂-C(CH₃)₂- | H | H |
| 8-OH | tetrazole-NH | -CH₂-C(CH₃)₂- | H | H |
| 8-SCH₃ | tetrazole-NH | -CH₂-C(CH₃)₂- | H | H |
| 8-S(O)CH₃ | tetrazole-NH | -CH₂-C(CH₃)₂- | H | H |
| 7-OCH₃ | tetrazole-NH | -CH₂-C(CH₃)₂- | H | H |
| 7-F | tetrazole-NH | -CH₂-C(CH₃)₂- | H | H |
| 7-Cl | tetrazole-NH | -CH₂-C(CH₃)₂- | H | H |

-continued
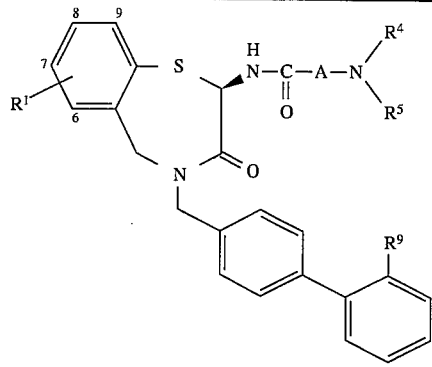
| R¹ | R⁹ | A | R⁴ | R⁵ |
|---|---|---|---|---|
| 7-I | tetrazole-NH | -CH$_2$-C(CH$_3$)(CH$_3$)- | H | H |
| H | tetrazole-NH | -C(CH$_3$)(CH$_3$)- | H | H |
| H | tetrazole-NH | -C(H)(CH$_3$)- | H | H |
| H | tetrazole-NH | -C(CH$_3$)(H)- | H | H |
| H | tetrazole-NH | -C(H)(CH$_2$OH)- | H | H |
| H | tetrazole-NH | -C(CH$_3$)(CH$_2$OH)- | H | H |
| H | tetrazole-NH | -C(H)(CH$_3$)- | CH$_3$ | H |
| H | tetrazole-NH | -CH$_2$-C(CH$_3$)(CH$_2$OH)- | H | H |
| H | tetrazole-NH | -CH$_2$-C(HOCH$_2$)(CH$_3$)- | H | H |

-continued
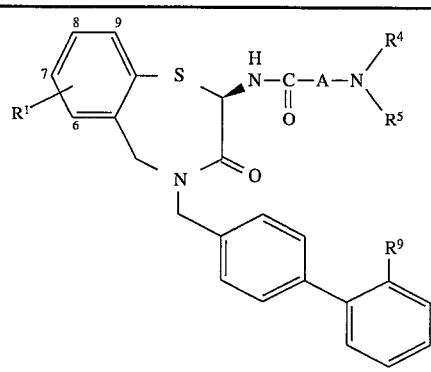
| R¹ | R⁹ | A | R⁴ | R⁵ |
|---|---|---|---|---|
| H | 5-tetrazolyl(NH) | —CH₂—C(HOCH₂)(CH₃)— | —CH₂CH(OH)CH₃ | H |
| H | 5-tetrazolyl(NH) | —CH₂—C(HOCH₂)(CH₃)— | —CH₂CH(OH)CH₂OH | H |
| H | 5-tetrazolyl(NH) | —C(H)(CH₂Ph)— | H | H |
| H | 5-tetrazolyl(NH) | —C(H)(CH₂-3-indolyl)— | H | H |
| H | 5-tetrazolyl(NH) | —C(H)(CH₂-imidazolyl)— | H | H |
| H | 5-tetrazolyl(NH) | 4-piperidinyl (NH) | — | — |
| H | 5-tetrazolyl(NH) | 3-piperidinylmethyl (NH) | — | — |
| H | 5-tetrazolyl(NH) | quinuclidinyl | — | — |

EXAMPLE 8
Utilizing the procedures described in Examples 1 to 4 and general methods of organic synthesis described in the chemical literature and familiar to one skilled in the art, the following compounds of Formula 1 can be prepared from the appropriately substituted starting materials and reagents.
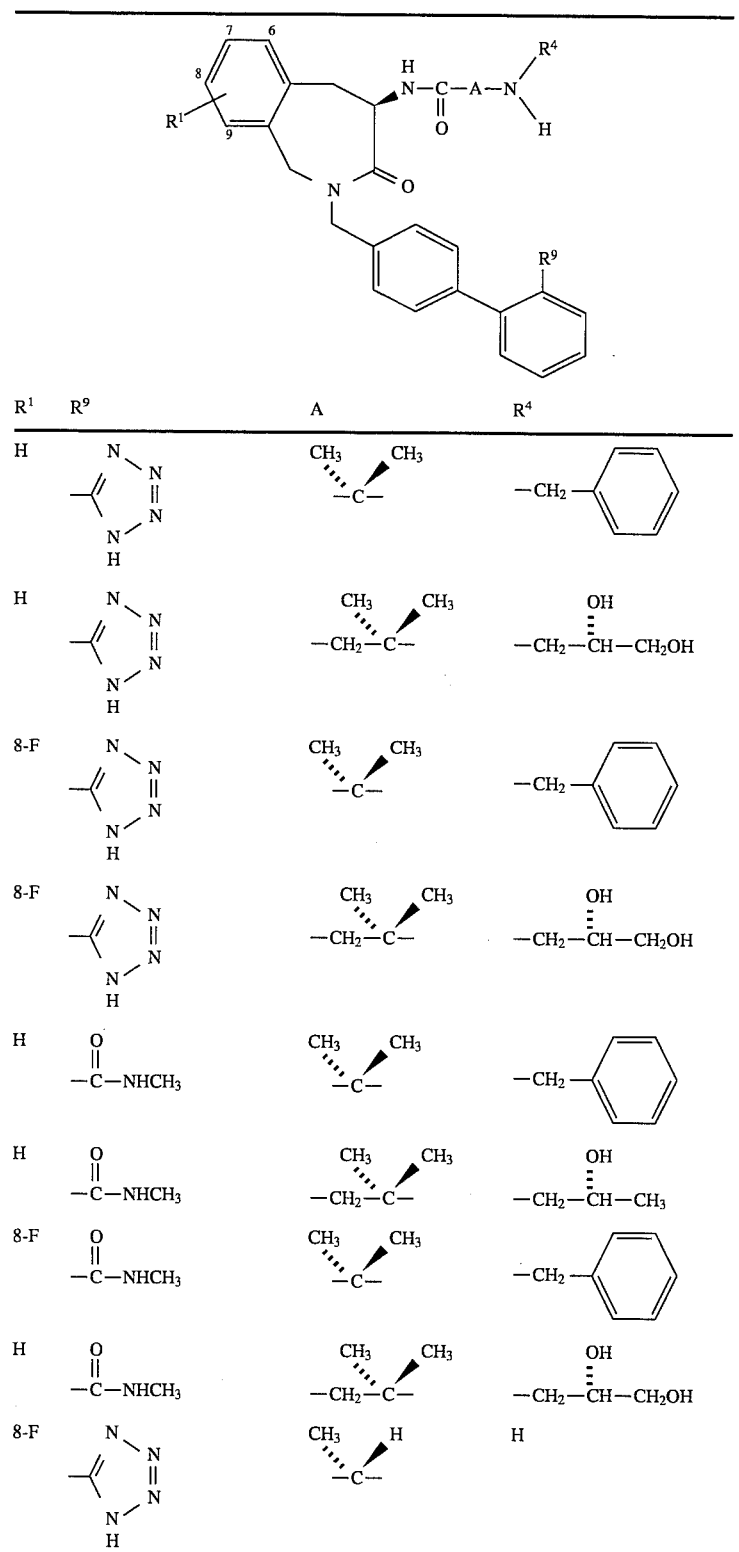

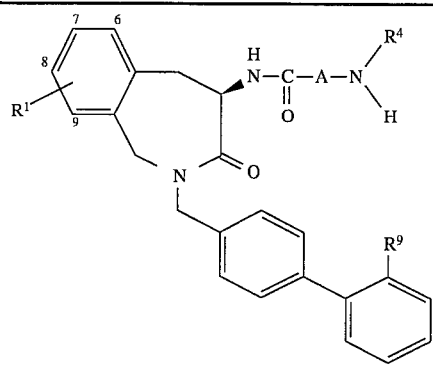
| R¹ | R⁹ | A | R⁴ |
|---|---|---|---|
| 8-F | tetrazole-NH | -C(H)(CH₂OH)- | H |
| 8-F | tetrazole-NH | -C(CH₃)(CH₂OH)- | H |
| H | -C(O)-NHCH₃ | -C(H)(CH₃)- | H |
| H | -C(O)-NHCH₃ | -CH₂-C(CH₃)(CH₂OH)- | H |
| H | -C(O)-NHCH₃ | -CH₂-C(HOCH₂)(CH₃)- | H |
| H | -C(O)-NHCH₃ | -CH₂-C(HOCH₂)(CH₃)- | H |
| H | -C(O)-NHCH₃ | -CH₂-C(HOCH₂)(CH₃)- | H |
| H | tetrazole-NH | -C(CH₃)(CH₃)- | -CH₂-C₆H₅ |
| H | tetrazole-NH | -CH₂-C(CH₃)(CH₃)- | -CH₂-CH(OH)-CH₂OH |
| 8-F | tetrazole-NH | -C(CH₃)(CH₃)- | -CH₂-C₆H₅ |
| 8-F | tetrazole-NH | -CH₂-C(CH₃)(CH₃)- | -CH₂-CH(OH)-CH₂OH |

-continued
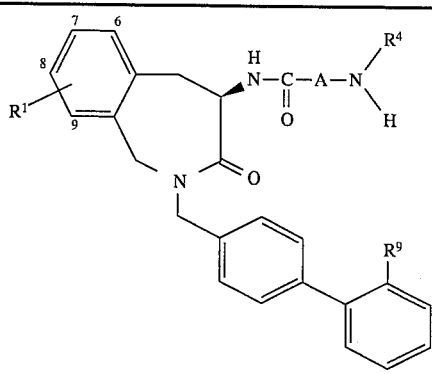
| R¹ | R⁹ | A | R⁴ |
|---|---|---|---|
| H | 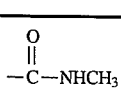 |  |  |
| H | 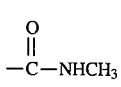 | 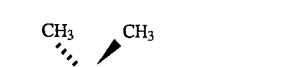 | 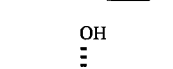 |
| 8-F | 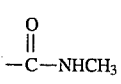 | 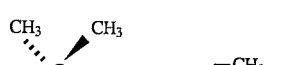 | 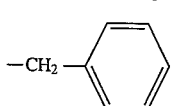 |
| H | 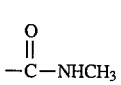 | 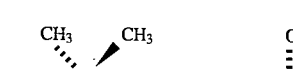 | 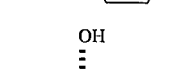 |
| H | 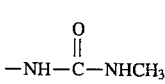 | 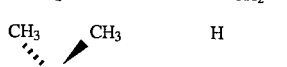 | H |
| H | 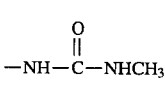 | 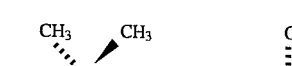 | 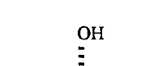 |
| 8-F | 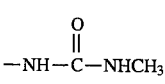 | 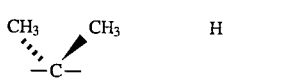 | H |
| H | 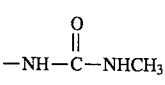 | 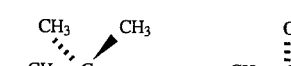 | 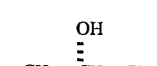 |
| H | 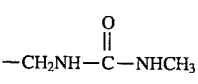 | 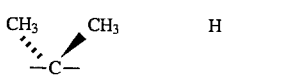 | H |
| H | 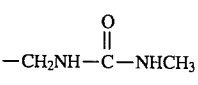 | 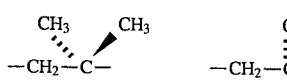 | 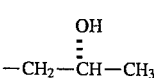 |
| 8-F | 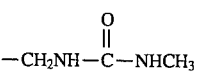 | 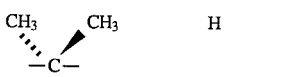 | H |
| H | 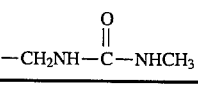 | 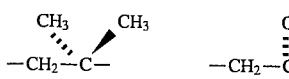 | 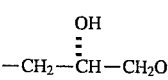 |

What is claimed is:

1. A compound having the formula:

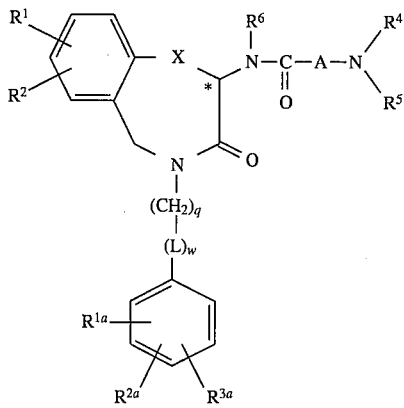

where L is:

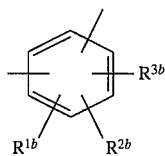

q is 0 to 4;

w is 0 or 1;

X is $CH_2$ or $S(O)_m$ where m is 0 to 2;

$R^1$, $R^2$, $R^{1a}$, $R^{2a}$, $R^{1b}$ and $R^{2b}$ are independently selected from: hydrogen, halogen, $C_1$-$C_7$ alkyl, $C_1$-$C_3$ perfluoroalkyl, $C_1$-$C_3$ perfluoroalkoxy, —$S(O)_m R^{7a}$, cyano, nitro, $R^{7b}O(CH_2)_v$—, $R^{7b}COO(CH_2)_v$—, $R^{7b}OCO(CH_2)_v$—, $R^{5b}R^{12b}N(CH_2)_v$—, $R^{7b}CON(R^{12b})(CH_2)_v$—, $R^{5b}R^{12b}NCO(CH_2)_v$—, phenyl, and substituted phenyl where the substituents on phenyl are selected from: 1 to 3 of halogen, $C_1$-$C_6$ alkyl, $C_1$-$C_6$ alkoxy, or hydroxy, wherein v is 0 to 3 and m is 0 to 2;

$R^{7a}$ and $R^{7b}$ are independently selected from: hydrogen, $C_1$-$C_3$ perfluoroalkyl, $C_1$-$C_6$ alkyl, phenyl or substituted phenyl, where the substitutents on phenyl are selected from: 1 to 3 of halogen, $C_1$-$C_6$ alkyl, $C_1$-$C_6$ alkoxy or hydroxy, substituted $C_1$-$C_6$ alkyl where the substitutents on alkyl are phenyl or substituted phenyl, where the substitutents on phenyl are selected from: 1 to 3 of halogen, $C_1$-$C_6$ alkyl, $C_1$-$C_6$ alkoxy or hydroxy;

$R^{3a}$ and $R^{3b}$ are independently selected from: hydrogen, $R^9$, $C_1$-$C_6$ alkyl substituted with $R^9$, phenyl substituted with $R^9$, or phenoxy substituted with $R^9$;

$R^9$ is selected from:

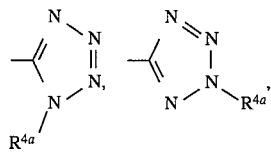

$R^{7b}O(CH_2)_v$—, $R^{7b}COO(CH_2)_v$—, $R^{7b}OCO(CH_2)_v$—, $R^{7b}CO(CH_2)_v$—, $R^{7b}O(CH_2)_vCO$—, $R_{5b}R^{12b}N(CH_2)_v$—, $R^{5b}R^{12b}NCO(CH_2)_v$—, $R^{5b}R^{12b}NCS(CH_2)_v$—, $R^{5b}R^{12c}NN(R^{12b})CO(CH_2)_v$—, $R^{5b}R^{12a}NN(R^{12b})CS(CH_2)_v$—, $R^{5b}R^{12b}NCON(R^{12a})(CH_2)_v$—, $R^{5b}R^{12b}NCSN(R^{12a})(CH_2)_v$—, $R^{5b}R^{12c}NN(R^{12b})CSN(R^{12a})(CH_2)_v$—, $R_{5b}R_{12c}NN(R^{12b})CON(R^{12a})(CH_2)_v$—, $R_{5b}R_{12c}NN(R^{12b})COO(CH_2)_v$—, $R^{5b}R^{12b}NCOO(CH_2)_v$— or $R^{13}OCON(R^{12a})(CH_2)_v$—, where v is 0 to 3;

$R^{12a}$, $R^{12b}$ and $R^{12c}$ are independently selected from: $R^{5a}$, $OR^{5a}$ or $COR^{5a}$, wherein $R^{12a}$ and $R^{12b}$, or $R^{12b}$ and $R^{12c}$, or $R^{12a}$ and $R^{12c}$, or $R^{12b}$ and $R^{5b}$, or $R^{12c}$ and $R^{5b}$, or $R^{13}$ and $R^{12a}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 3, and $R^1$ and $R^{10}$ are as defined;

$R^{13}$ is selected from: $C_1$-$C_3$ perfluoroalkyl, $C_1$-$C_6$ alkyl, phenyl, substituted phenyl where the substituents on phenyl are selected from: 1 to 3 of halogen, $C_1$-$C_6$ alkyl, $C_1$-$C_6$ alkoxy or hydroxy, and substituted $C_1$-$C_6$ alkyl, where the substitutents on alkyl are selected from: hydroxy, —$NR^{10}R^{11}$, carboxy, phenyl and substituted phenyl, wherein the substituents on phenyl are selected from: 1 to 3 of halogen, $C_1$-$C_6$ alkyl, $C_1$-$C_6$ alkoxy or hydroxy;

$R^{10}$ and $R^{11}$ are independently selected from: hydrogen, $C_1$-$C_6$ alkyl, phenyl, phenyl $C_1$-$C_6$ alkyl, $C_1$-$C_5$ alkoxycarbonyl or $C_1$-$C_5$ alkanoyl-$C_1$-$C_6$ alkyl;

$R^4$, $R^{4a}$, $R^5$, $R^{5a}$ and $R^{5b}$ are independently selected from:
hydrogen;
phenyl;
substituted phenyl where the substituents on phenyl are selected from: 1 to 5 of hydroxy, $C_1$-$C_6$ alkoxy, $C_3$-$C_7$ cycloalkyl, fluoro, phenyl independently disubstituted with $R^1$ and $R^2$, and phenyl($C_1$-$C_3$ alkoxy) wherein the phenyl is independently disubstituted with $R^1$ and $R^2$;
$C_1$-$C_{10}$ alkyl;
substituted $C_1$-$C_{10}$ alkyl, where the substituents on the alkyl are selected from: 1 to 5 of hydroxy, $C_1$-$C_6$ alkoxy, $C_3$-$C_7$ cycloalkyl, fluoro, phenyl independently disubstituted with $R^1$ and $R^2$, phenyl($C_1$-$C_3$ alkoxy) wherein the phenyl is independently disubstituted with $R^1$ and $R^2$, $C_1$-$C_{20}$-alkanoyloxy, $C_1$-$C_5$ alkoxycarbonyl, carboxy, formyl, and —$NR^{10}R^{11}$;
$C_3$-$C_{10}$ alkenyl; substituted $C_3$-$C_{10}$ alkenyl, where the substituents on the alkenyl are selected from: 1 to 5 of hydroxy, $C_1$-$C_6$ alkoxy, $C_3$-$C_7$ cycloalkyl, fluoro, phenyl independently disubstituted with $R^1$ and $R^2$, phenyl($C_1$-$C_3$ alkoxy) wherein the phenyl is independently disubstituted with $R^1$ and $R^2$, $C_1$-$C_{20}$-alkanoyloxy, $C_1$-$C_5$ alkoxycarbonyl, carboxy, formyl, and —$NR^{10}R^{11}$;
$C_3$-$C_{10}$ alkynyl; and
substituted $C_3$-$C_{10}$ alkynyl where the substituents on the alkynyl are selected from: 1 to 5 of hydroxy, $C_1$-$C_6$ alkoxy, $C_3$-$C_7$ cycloalkyl, fluoro, phenyl independently disubstituted with $R^1$ and $R^2$, phenyl($C_1$-$C_3$ alkoxy) wherein the phenyl is independently disubstituted with $R^1$ and $R^2$, $C_1$-$C_{20}$-alkanoyloxy, $C_1$-$C_5$ alkoxycarbonyl, carboxy, formyl, and —$NR^{10}R^{11}$; where $R^1$, $R^2$, $R^{10}$ and $R^{11}$ are as defined above; or where $R^4$ and $R^5$ can be taken together to form —$(CH_2)_r$—B—$(CH_2)_s$— where B is $CHR^1$, O, $S(O)_m$ or N-$R^{10}$, r and s are independently 1 to 3, m is 0, 1 or 2 and $R^1$ and $R^{10}$ are as defined above;

$R^6$ is selected from: hydrogen, $C_1$-$C_{10}$ alkyl, phenyl or phenyl $C_1$-$C_{10}$ alkyl;

A is:

$$-(CH_2)_x-\underset{R^{8a}}{\overset{R^8}{C}}-(CH_2)_y-$$

where x and y are independently 0–3;

R$^8$ and R$^8$a are independently selected from: hydrogen, C$_1$-C$_{10}$ alkyl, trifluoromethyl, phenyl, and substituted C$_1$-C$_{10}$ alkyl, where the substitutents on alkyl are selected from: 1 to 3 of imidazolyl, indolyl, hydroxy, fluoro, —S(O)$_m$R$^{7a}$, C$_1$-C$_6$ alkoxy, C$_3$-C$_7$ cycloalkyl, phenyl independently disubstituted with R$^1$ and R$^2$, phenyl(C$_1$-C$_3$ alkoxy) wherein the phenyl is independently disubstituted with R$^1$ and R$^2$, C$_1$-C$_5$ alkanoyloxy, C$_1$-C$_5$ alkoxycarbonyl, carboxy, formyl, or —NR$^{10}$R$^{11}$ where R$^1$, R$^2$, R$^{7a}$, R$^{10}$, R$^{11}$ and m are as defined above; or R$^8$ and R$^{8a}$ can be taken together to form —(CH$_2$)$_t$— where t is 2 to 6; and R$^8$ and R$^{8a}$ can independently be joined to R$^5$ to form alkylene bridges between the terminal nitrogen and the alkyl portion of the A group wherein the bridge contains from one to five carbon atoms; and pharmaceutically acceptable salts thereof.

2. The compound of claim 1 wherein:

q is 0 to 2;

w is 0 or 1;

X is CH$_2$ or S(O)$_m$, where m is 0 to 2;

R$^1$, R$^2$, R$^{1a}$, R$^{2a}$, R$^{1b}$ and R$^{2b}$ are independently selected from: hydrogen, halogen, C$_1$-C$_7$ alkyl, C$_1$-C$_3$ perfluoroalkyl, —S(O)$_m$R$^{7a}$, R$^{7b}$O(CH$_2$)$_v$—, R$^{7b}$COO(CH$_2$)$_v$—, R$^{7b}$OCO(CH$_2$)$_v$—, phenyl, and substituted phenyl where the substituents on phenyl are selected from: 1 to 3 of halogen, C$_1$-C$_6$ alkyl, C$_1$-C$_6$ alkoxy, or hydroxy, wherein v is 0 to 3;

R$^{7a}$ and R$^{7b}$ are independently selected from: hydrogen, C$_1$-C$_3$ perfluoroalkyl, phenyl, C$_1$-C$_6$ alkyl, and substituted C$_1$-C$_6$ alkyl where the substitutent on alkyl is phenyl;

R$^{3a}$ and R$^{3b}$ are independently selected from: hydrogen, R$^9$, C$_1$-C$_6$ alkyl substituted with R$^9$, phenyl substituted with R$^9$, or phenoxy substituted with R$^9$;

R$^9$ is selected from:

[structures]

R$^{7b}$O(CH$_2$)$_v$—, R$^{7b}$COO(CH$_2$)$_v$—, R$^{7b}$OCO(CH$_2$)$_v$—, R$^{7b}$CO(CH$_2$)$_v$—, R$^{5b}$R$^{12b}$N(CH$_2$)$_v$—, R$^{5b}$R$^{12b}$NCO(CH$_2$)$_v$—, R$^{5b}$R$^{12b}$NCS(CH$_2$)$_v$—, R$^{5b}$R$^{12c}$NN(R$^{12b}$)CO(CH$_2$)$_v$—, R$^{5b}$R$^{12b}$NCON(R$^{12a}$)(CH$_2$)$_v$—, R$^{5b}$R$^{12b}$NCSN(R$^{12a}$)(CH$^2$)$_v$—, R$^{5b}$R$^{12c}$NN(R$^{12b}$)CSN(R$^{12a}$)(CH$_2$)$_v$—, R$^{5b}$R$^{12c}$NN(R$^{12b}$)CON(R$^{12a}$)(CH$^2$)$_v$—, R$^{5b}$R$^{12c}$NN(R$^{12b}$)COO(CH$_2$)$_v$—, R$^{5b}$R$^{12b}$NCOO(CH$_2$)$_v$— or R$^{13}$OCON(R$^{12a}$)(CH$_2$)$_v$—, where v is 0 to 3;

R$^{12a}$, R$^{12b}$ and R$^{12c}$ are independently selected from: R$^{5a}$, OR$^{5a}$ or COR$^5$, wherein R$^{12a}$ and R$^{12b}$, or R$^{12b}$ and R$^{12c}$, or R$^{12a}$ and R$^{12c}$, or R$^{12b}$ and R$^{5b}$, or R$^{12c}$ and R$^{5b}$, or R$^{13}$ and R$^{12a}$ can be taken together to form —(CH$_2$)$_r$—B—(CH$_2$)$_s$— where B is CHR$^1$, O, S(O)$_m$ or NR$^{10}$, m is 0, 1 or 2, r and s are independently 0 to 3, and R$^1$ and R$^{10}$ are as defined;

R$^{13}$ is selected from: C$_1$-C$_3$ perfluoroalkyl, C$_1$-C$_6$ alkyl, phenyl, substituted phenyl where the substituents on the phenyl are selected from 1 to 3 of halogen, C$_1$-C$_6$ alkyl, C$_1$-C$_6$ alkoxy or hydroxy, and substituted C$_1$-C$_6$ alkyl, where the substituents on alkyl are selected from: hydroxy, —NR$^{10}$R$^{11}$, carboxy, phenyl, or substituted phenyl, where the substituents on the phenyl are selected from 1 to 3 of halogen, C$_1$-C$_6$ alkyl, C$_1$-C$_6$ alkoxy or hydroxy;

R$^{10}$ and R$^{11}$ are independently selected from: hydrogen, C$_1$-C$_6$ alkyl, phenyl C$_1$-C$_6$ alkyl, or C$_1$-C$_5$ alkanoyl-C$_1$-C$_6$ alkyl;

R$^4$, R$^{4a}$, R$^5$, R$^{5a}$ and R$^{5b}$ are independently selected from: hydrogen;

phenyl;

substituted phenyl, where the substituents on the phenyl are selected from: 1 to 5 of hydroxy, C$_1$-C$_6$ alkoxy, C$_3$-C$_7$ cycloalkyl, fluoro, phenyl independently disubstituted with R$^1$ and R$^2$, phenyl (C$_1$-C$_3$ alkoxy) wherein the phenyl is independently disubstituted with R$^1$ and R$^2$, C$_1$-C$_{20}$-alkanoyloxy, C$_1$-C$_5$ alkoxycarbonyl, carboxy or formyl;

C$_1$-C$_{10}$ alkyl;

substituted C$_1$-C$_{10}$ alkyl where the substituents on the alkyl are selected from: 1 to 5 of hydroxy, C$_1$-C$_6$ alkoxy, C$_3$-C$_7$ cycloalkyl, fluoro, phenyl independently disubstituted with R$^1$ and R$^2$, phenyl (C$_1$-C$_3$ alkoxy) wherein the phenyl is independently disubstituted with R$^1$ and R$^2$, C$_1$-C$_{20}$-alkanoyloxy, C$_1$-C$_5$ alkoxycarbonyl, carboxy or formyl; or where R$^4$ and R$^5$ can be taken together to form —(CH$_2$)$_r$—B—(CH$_2$)$_s$— where B is CHR$^1$, O, S(O)$_m$ or N-R$^{10}$, r and s are independently 1 to 3, m is 0, 1 or 2 and R$^1$ and R$^{10}$ are as defined above;

R$^6$ is selected from: hydrogen, C$_1$-C$_{10}$ alkyl or phenyl C$_1$-C$_{10}$ alkyl;

A is selected from:

$$-(CH_2)_x-\underset{R^{8a}}{\overset{R^8}{C}}-(CH_2)_y-$$

where x and y are independently 0–2;

R$^8$ and R$^{8a}$ are independently selected from: hydrogen, C$_1$-C$_{10}$ alkyl, and substituted C$_1$-C$_{10}$ alkyl, where the substitutents are on alkyl are selected from: 1 to 3 of imidazolyl, indolyl, hydroxy, fluoro, —S(O)$_m$R$^{7a}$, C$_1$-C$_6$ alkoxy, C$_3$-C$_7$ cycloalkyl, phenyl independently disubstituted with R$^1$ and R$^2$, phenyl (C$_1$-C$_3$ alkoxy) wherein the phenyl is independently disubstituted with R$^1$ and R$^2$, C$_1$-C$_5$ alkanoyloxy, C$_1$-C$_5$ alkoxycarbonyl, carboxy, formyl or —NR$^{10}$R$^{11}$ where R$^1$, R$^2$, R$^{7a}$, R$^{10}$, R$^{11}$ and m are as defined above; or R$^8$ and R$^{8a}$ can be taken together to form —(CH$_2$)$_t$— where t is 2 to 4; and R$^8$ and R$^{8a}$ can independently be joined to R$^5$ to form alkylene bridges between the terminal nitrogen and the alkyl portion of the A group wherein the bridge contains from one to five carbon atoms; and pharmaceutically acceptable salts thereof.

3. The compound of claim 2 wherein:

q is 0 to 2;

95 w is 0 or 1;

X is $CH_2$ or $S(O)_m$, where m is 0 or 1;

$R^1$, $R^2$, $R^{1a}$, $R^{2a}$, $R^{1b}$ and $R^{2b}$ are independently selected from: hydrogen, halogen, $C_1$-$C_7$ alkyl, $C_1$-$C_3$ perfluoroalkyl, —$S(O)_mR^{7a}$, $R^{7b}O(CH_2)_v$—, $R^{7b}COO(CH_2)_v$—, $R^{7b}OCO(CH_2)_v$—, phenyl, and substituted phenyl where the substituents on phenyl are selected from: 1 to 3 of halogen, $C_1$-$C_6$ alkyl, $C_1$-$C_6$ alkoxy, or hydroxy, and where v is 0 to 2;

$R^{7a}$ and $R^{7b}$ are independently selected from: hydrogen, $C_1$-$C_6$ alkyl, or substituted $C_1$-$C_6$ alkyl where the substitutent on alkyl is phenyl;

$R^{3a}$ and $R^{3b}$ are independently selected from: hydrogen, $R^9$, $C_1$-$C_6$ alkyl substituted with $R^9$, or phenoxy substituted with $R^9$;

$R^9$ is selected from:

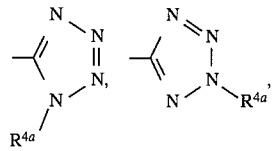

$R^{7b}O(CH_2)_v$—, $R^{7b}COO(CH_2)_v$—, $R^{7b}OCO(CH_2)_v$—, $R^{7b}CO(CH_2)_v$—, $R^{5b}R^{12b}N(CH_2)_v$—, $R^{5b}R^{12b}NCO(CH_2)_v$—, $R^{5b}R^{12c}NN(R^{12b})CO(CH_2)_v$—, $R^{5b}R^{12b}NCON(R^{12a})(CH_2)_v$—, $R^{5b}R^{12c}NN(R^{12b})CSN(R^{12a})(CH_2)_v$—, $R^{5b}R^{12c}NN(R^{12b})CON(R^{12a})(CH_2)_v$—, $R^{5b}R^{12c}NN(R^{12b})COO(CH_2)_v$—, $R^{5b}R^{12b}NCOO(CH_2)_v$— or $R^{13}OCON(R^{12a})(CH^2)_v$—, where v is 0 to 2;

$R^{12a}$, $R^{12b}$ and $R^{12c}$ are independently selected from: $R^{5a}$ or $OR^{5a}$, wherein $R^{12a}$ and $R^{12b}$, or $R^{12b}$ and $R^{12c}$, or $R^{12a}$ and $R^{12c}$, or $R^{12b}$ and $R^{5b}$, or $R^{12c}$ and $R^{5b}$, or $R^{13}$ and $R^{12a}$ can be taken together to form —$(CH_2)_r$—$_B$—$(CH_2)_s$— where B is $CHR^1$, O, $S(O)_m$ or $NR^{10}$, m is 0, 1 or 2, r and s are independently 0 to 2 and $R^1$ and $R^{10}$ are as defined;

$R^{13}$ is selected from: $C_1$-$C_6$ alkyl, phenyl, substituted phenyl where the substituents on the phenyl are selected from: 1 to 3 of halogen, $C_1$-$C_6$ alkyl, $C_1$-$C_6$ alkoxy or hydroxy, and substituted $C_1$-$C_6$ alkyl, where the substitutents on the alkyl are selected from: phenyl and substituted phenyl, where the substituents on the phenyl are selected from: 1 to 3 of halogen, $C_1$-$C_6$ alkyl, $C_1$-$C_6$ alkoxy or hydroxy;

$R^{10}$ and $R^{11}$ are independently selected from: hydrogen, $C_1$-$C_6$ alkyl, phenyl $C_1$-$C_6$ alkyl, or $C_1$-$C_5$ alkanoyl-$C_1$-$C_6$ alkyl;

$R^4$, $R^{4a}$, $R^5$, $R^{5a}$ and $R^{5b}$ are independently selected from: hydrogen; $C_1$-$C_{10}$ alkyl; and substituted $C_1$-$C_{10}$ alkyl where the substituents on the alkyl are selected from: 1 to 5 of hydroxy, $C_1$-$C_6$ alkoxy, fluoro, phenyl independently disubstituted with $R^1$ and $R^2$, $C_1$-$C_{20}$-alkanoyloxy, $C_1$-$C_5$ alkoxycarbonyl or carboxy, where $R^1$ and $R^2$ are as defined above;

$R^6$ is hydrogen or $C_1$-$C_{10}$ alkyl;

96

A is:

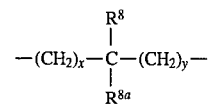

where x and y are independently 0–1;

$R^8$ and $R^{8a}$ are independently selected from: hydrogen, $C_1$-$C_{10}$ alkyl, and substituted $C_1$-$C_{10}$ alkyl, where the substitutents are selected from: 1 to 3 of imidazolyl, indolyl, hydroxy, fluoro, —$S(O)_mR^{7a}$, $C_1$-$C_6$ alkoxy, $C_3$-$C_7$ cycloalkyl, phenyl independently disubstituted with $R^1$ and $R^2$, phenyl ($C_1$-$C_3$ alkoxy) wherein the phenyl is independently disubstituted with $R^1$ and $R^2$, $C_1$-$C_5$ alkanoyloxy, $C_1$-$C_5$ alkoxycarbonyl, carboxy, formyl or —$NR_{10}R^{11}$ where $R^1$, $R^2$, $R^{7a}$, $R^{10}$, $R^{11}$ and m are as defined above; or $R^8$ and $R^{8a}$ can be taken together to form —$(CH_2)_t$— where t is 2; and $R^8$ and $R^{8a}$ can independently be joined to $R^5$ to form alkylene bridges between the terminal nitrogen and the alkyl portion of the A group wherein the bridge contains from one to five carbon atoms; and pharmaceutically acceptable salts thereof.

4. The compound of claim 3 wherein:

q is 1;

w is 1;

X is $CH_2$ or $S(O)_m$, where m is 0 or 1;

$R^1$, $R^2$, $R^{1a}$, $R^{2a}$, $R^{1b}$ and $R^{2b}$ are independently selected from: hydrogen, halogen, $C_1$-$C_7$ alkyl, $C_1$-$C_3$ perfluoroalkyl, —$S(O)_mR^{7a}$, $R^{7b}O(CH_2)_v$—, $R^{7b}COO(CH_2)_v$—, phenyl, and substituted phenyl where the substituents on phenyl are selected from: 1 to 3 of halogen, $C_1$-$C_6$ alkyl, $C_1$-$C_6$ alkoxy, or hydroxy, and wherein v is 0 or 1;

$R^{7a}$ and $R^{7b}$ are independently selected from: hydrogen, $C_1$-$C_6$ alkyl, or substituted $C_1$-$C_6$ alkyl where the substitutent on the alkyl is phenyl;

$R^{3a}$ and $R^{3b}$ are independently selected from: hydrogen, $R^9$, or $C_1$-$C_6$ alkyl substituted with $R^9$;

$R^9$ is selected from:

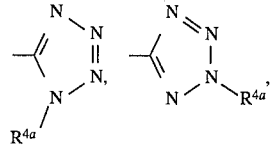

$R^{7b}O(CH_2)_v$—, $R^{7b}COO(CH_2)_v$—, $R^{7b}OCO(CH_2)_v$—, $R^{7b}CO(CH_2)_v$—, $R^{5b}R^{12b}N(CH_2)_v$—, $R^{5b}R^{12b}NCO(CH_2)_v$—, $R^{5b}R^{12c}NN(R^{12b})CO(CH_2)_v$—, $R^{5b}R^{12b}NCON(R^{12a})(CH_2)_v$—, $R^{5b}R^{12c}NN(R^{12b})CON(R^{12a})(CH_2)_v$—, $R^{5b}R^{12c}NN(R^{12b})COO(CH_2)_v$—, $R^{5b}R^{12b}NCOO(CH_2)_v$— or $R^{13}OCON(R^{12a})(CH_2)_v$—, where v is 0 to 2;

$R^{12a}$, $R^{12b}$ and $R^{12c}$ are independently $R^{5a}$; wherein $R^{12a}$ and $R^{12b}$, or $R^{12b}$ and $R^{12c}$, or $R^{12a}$ and $R^{12c}$, or $R^{12b}$ and $R^{5b}$, or $R^{12c}$ and $R^{5b}$, or $R^{13}$ and $R^{12a}$ can be taken together to form —$(CH_2)_r$—$_B$—$(CH_2)_s$— where B is $CHR^1$, O, $S(O)_m$ or $NR^{10}$, m is 0, 1 or 2, r and s are independently 0 to 2 and $R^1$ and $R^{10}$ are as defined;

$R^{13}$ is selected from: $C_1$-$C_6$ alkyl, phenyl, substituted phenyl where the substituents on the phenyl are selected from: 1 to 3 of halogen, $C_1$-$C_6$ alkyl, $C_1$-$C_6$ alkoxy or hydroxy, and substituted $C_1$-$C_6$ alkyl, where the substitutents on the alkyl are selected from phenyl or substituted phenyl, where the substituents on the phenyl are selected from: 1 to 3 of halogen, $C_1$-$C_6$ alkyl, $C_1$-$C_6$ alkoxy or hydroxy;

$R^{10}$ and $R^{11}$ are independently selected from: hydrogen, $C_1$-$C_6$ alkyl, or $C_1$-$C_5$ alkanoyl-$C_1$-$C_6$ alkyl; $R^4$, $R^{4a}$, $R^5$, $R^{5a}$ and $R^{5b}$ are independently selected from: hydrogen;

$C_1$-$C_{10}$ alkyl;

and substituted $C_1$-$C_{10}$alkyl where the substituents on the alkyl are selected from: 1 to 3 of hydroxy, $C_1$-$C_3$ alkoxy, fluoro, phenyl independently disubstituted with $R^1$ and $R^2$, $C_1$-$C_{20}$-alkanoyloxy, $C_1$-$C_5$ alkoxycarbonyl or carboxy; where $R^1$ and $R^2$ are as defined above;

$R^6$ is hydrogen;

A is:

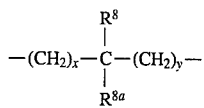

where x and y are independently 0–1;

$R^8$ and $R^{8a}$ are independently selected from: hydrogen, $C_1$-$C_{10}$ alkyl, and substituted $C_1$-$C_{10}$ alkyl, where the substitutents on alkyl are selected from: 1 to 3 of imidazolyl, indolyl, hydroxy, fluoro, —$S(O)_mR^{7a}$, $C_1$-$C_6$ alkoxy, $C_3$-$C_7$ cycloalkyl, phenyl independently disubstituted with $R^1$ and $R^2$, $C_1$-$C_5$ alkanoyloxy, $C_1$-$C_5$ alkoxycarbonyl or carboxy, where $R^1$, $R^2$, $R^{7a}$, and m are as defined above; or $R^8$ and $R^{8a}$ can be taken together to form —$(CH_2)_t$— where t is 2; and $R^8$ and $R^{8a}$ can independently be joined to $R^5$ to form alkylene bridges between the terminal nitrogen and the alkyl portion of the A group wherein the bridge contains from one to five carbon atoms; and pharmaceutically acceptable salts thereof.

5. The stereospecific compound of claim 1 having the following structural formula:

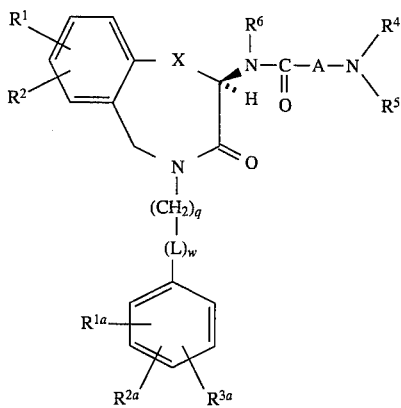

where $R^1$, $R^2$, $R^{1a}$, $R^{2a}$, $R^{3a}$, $R^4$, $R^5$, $R^6$, A, L, X, q and w are as defined in claim 1.

6. A compound which is selected from the group consisting of:

3-Amino-3-methyl-N-[2,3,4,5-tetrahydro-3-oxo-2-[[2'-(1H-tetrazol- 5-yl)[1,1'-biphenyl]-4-yl]methyl]-1H-2-benzazepin-4(R)-yl]butanamide;

2Amino-2-methyl-N-[2,3,4,5-tetrahydro-3-oxo-2-[[2'-(1H-tetrazol- 5-yl)[1,1'-biphenyl]-4-yl]methyl]-1H-2-benzazepin-4(R)-yl]propanamide;

3-[2(R)-Hydroxypropyl]amino-3-methyl-N-[2,3,4,5-tetrahydro-3-oxo- 2-[[2'-(1H-tetrazol-5-yl)[1,1'-biphenyl]-4-yl]methyl]-1H-2-benzazepin- 4(R)-yl]butanamide;

3-[2(S),3-Dihydroxypropyl]amino-3-methyl-N-[2,3,4,5-tetrahydro- 3-oxo-2[[2'-(1H-tetrazol-5-yl)[1,1'-biphenyl]- 4-yl]methyl]-1H-2-benzazepin-4(R)-yl]butanamide;

3-Amino-3-methyl-N-[2,3,4,5-tetrahydro-7-methoxy-3-oxo-2-[[2'-( 1H-tetrazol-5-yl)[1,1'-biphenyl]-4-yl]methyl]-1H-2-benzazepin- 4(R)-yl]-butanamide;

2-Amino-2-methyl-N-[2,3,4,5-tetrahydro-7-methoxy-3-oxo-2-[[2'-( 1H-tetrazol-5-yl)[1,1'-biphenyl]-4-yl]methyl]-1H-2-benzazepin-4(R)-yl]-propanamide;

3-[2(R)-Hydroxypropyl]amino-3-methyl-N-[2,3,4,5-tetrahydro- 7-methoxy-3-oxo-2-[[2'-(1H-tetrazol-5-yl)[1,1'-biphenyl]-4-yl]methyl]- 1H-2-benzazepin-4(R)-yl]butanamide;

3-[2(S),3-Dihydroxypropyl]amino-3-methyl-N-[2,3,4,5-tetrahydro- 7-methoxy-3-oxo-2-[[2'-(1H-tetrazol-5-yl)[1,1'-biphenyl]-4-yl]methyl]- 1H-2-benzazepin-4(R)-yl]butanamide;

3-Amino-3-methyl-N-[2,3,4,5-tetrahydro-7-methylthio-3-oxo-2-[[2'-( 1H-tetrazol-5-yl)[1,1'-biphenyl]-4-yl]methyl]-1H-2-benzazepin-4(R)-yl]butanamide;

2-Amino-2-methyl-N-[2,3,4,5-tetrahydro-7-methylthio-3-oxo-2-[[2'-( 1H-tetrazol-5-yl)[1,1'-biphenyl]-4-yl]methyl]-1H-2-benzazepin-4(R)-yl]propanamide;

3-[2(R)-Hydroxypropyl]amino-3-methyl-N-[2,3,4,5-tetrahydro- 7-methylthio-3-oxo-2-[[2'-(1H-tetrazol-5-yl)[1,1'-biphenyl]-4-yl]methyl]- 1H-2-benzazepin-4(R)-yl]butanamide;

3-[2(S),3-Dihydroxypropyl]amino-3-methyl-N-[2,3,4,5-tetrahydro- 7-methylthio-3-oxo-2-[[2'-(1H-tetrazol-5-yl)[1,1'-biphenyl]-4-yl]methyl]- 1H-2-benzazepin-4(R)-yl]butanamide;

3-Amino-3-methyl-N-[2,3,4,5-tetrahydro-7-fluoro-3-oxo-2-[[2'-( 1H-tetrazol-5-yl)[1,1'-biphenyl]-4-yl]methyl]-1H-2-benzazepin-4(R )-yl]-butanamide;

2-Amino-2-methyl-N-[2,3,4,5-tetrahydro-7-fluoro-3-oxo-2-[[2'-( 1H-tetrazol-5-yl)[1,1'-biphenyl]-4-yl]methyl]-1H-2-benzazepin-4(R)-yl]-propanamide;

3-[2(R)-Hydroxypropyl]amino-3-methyl-N-[2,3,4,5-tetrahydro-7-fluoro- 3-oxo-2-[[2'-(1H-tetrazol-5-yl)[1,1'-biphenyl]-4-yl]methyl]-1H- 2-benzazepin-4(R)-yl]butanamide;

3-[2(S),3-Dihydroxypropyl]amino-3-methyl-N-[2,3,4,5-tetrahydro- 7-fluoro-3-oxo-2-[[2'-(1H-tetrazol-5-yl)[1,1'-biphenyl]-4-yl]methyl]- 1H-2-benzazepin-4(R)-yl]butanamide;

N-Ethyl-4'-[[4(R)-[(3-amino-3-methyl-1-oxobutyl)amino]- 2,3,4,5-tetrahydro-3-oxo-1H-2-benzazepin-2-yl]methyl][1,1'-biphenyl]-2-carboxamide;

N-Ethyl-4'-[[4(R)-[(2-amino-2-methyl-1-oxopropyl)amino]- 2,3,4,5-tetrahydro-3-oxo-1H-2-benzazepin-2-yl]methyl][1,1'-biphenyl]-2-carboxamide;

N-Ethyl-4'-[[4(R)-[[[[2(R)-hydroxypropyl]amino]-3-methyl- 1-oxo-butyl]amino]-2,3,4,5-tetrahydro-3-oxo-1H-2-benzazepin-2-yl]methyl]-[1,1'-biphenyl]-2-carboxamide;

N-Ethyl-4'-[[4(R)-[[[[2(S),3-dihydroxypropyl]amino]-3-methyl- 1-oxo-butyl)amino]-2,3,4,5-tetrahydro-3-oxo- 1H-2-benzazepin-2-yl]methyl]-[1,1'-biphenyl]-2-carboxamide;

N-Ethyl-4'-[[4(R)-[(2-amino-2-methyl-1-oxopropyl)amino]- 2,3,4,5-tetrahydro-7-methylthio-3-oxo-1H-2-benzazepin-2-yl]methyl][1,1'-biphenyl]- 2-carboxamide;

N-Ethyl-4'-[[4(R)-[[[[2(R)-hydroxypropyl]amino]-3-methyl- 1-oxobutyl]-amino]-2,3,4,5-tetrahydro-7-methylthio-3-oxo-1H-2-benzazepin- 2-yl]-methyl][1,1'-biphenyl]-2-carboxamide;

N-Ethyl-4'-[[4(R)-[[[[2(S),3-dihydroxypropyl]amino]-3-methyl- 1-oxo-butyl)amino]-2,3,4,5-tetrahydro-7-methylthio-3-oxo- 1H-2-benzazepin- 2-yl]methyl][1,1'-biphenyl]-2-carboxamide;

N-Ethyl-4'-[[4(R)-[(3-amino-3-methyl-1-oxobutyl)amino]- 2,3,4,5-tetrahydro-7-methoxy-3-oxo-1H-2-benzazepin-2-yl]methyl][1,1'-biphenyl]- 2-carboxamide;

N-Ethyl-4'-[[4(R)-[[[[2(R)-hydroxypropyl]amino]-3-methyl- 1-oxobutyl]-amino]-2,3,4,5-tetrahydro-7-methoxy-3-oxo-1H-2-benzazepin- 2-yl]-methyl][1,1'-biphenyl]-2-carboxamide;

N-Ethyl-4'-[[4(R)-[[[[2(S),3-dihydroxypropyl]amino]-3-methyl- 1-oxo-butyl)amino]-2,3,4,5-tetrahydro-7-methoxy-3-oxo-1H-2-benzazepin- 2-yl]methyl][1,1'-biphenyl]-2-carboxamide;

N- Ethyl-4'-[[4 (R)-[(3-amino-3-methyl-1-oxobutyl)amino]- 2,3,4,5-tetrahydro-7-fluoro-3-oxo-1H-2-benzazepin-2-yl]methyl][1,1'-biphenyl]- 2-carboxamide;

N-Ethyl-4'-[[4(R)-[[[[2(R)-hydroxypropyl]amino]-3-methyl- 1-oxobutyl]-amino]-2,3,4,5-tetrahydro-7-fluoro-3-oxo-1H-2-benzazepin- 2-yl]-methyl][1,1'-biphenyl]-2-carboxamide;

N-Ethyl-4'-[[4(R)-[[[[2(S),3-dihydroxypropyl]amino]-3-methyl- 1-oxo-butyl)amino]-2,3,4,5-tetrahydro-7-fluoro-3-oxo-1H-2-benzazepin- 2-yl]methyl][1,1'-biphenyl]-2-carboxamide;

2-Amino-2-methyl-N-[2,3,4,5-tetrahydro-3-oxo-2-[[2'-hydroxymethyl-[1,1'-biphenyl]-4-yl]methyl]-1H-2-benzazepin-4(R)-yl]propanamide;

3-[2(R)-Hydroxypropyl]amino-3-methyl-N-[2,3,4,5-tetrahydro-3-oxo- 2-[[2'-hydroxymethyl[1,1'-biphenyl]-4-yl]methyl]-1H-2-benzazepin- 4(R)-yl]butanamide;

3-[2(S),3-Dihydroxypropyl]amino-3-methyl-N-[2,3,4,5-tetrahydro- 3-oxo-2-[[2'-hydroxymethyl[1,1'-biphenyl]-4-yl]methyl]-1H- 2-benzazepin-4(R)-yl]butanamide;

3-Amino-3-methyl-N-[2,3,4,5-tetrahydro-7-methylthio-3-oxo-2-[[2'-hydroxymethyl[1,1'-biphenyl]-4-yl]methyl]-1H-2-benzazepin-4(R)-yl]-butanamide;

3-[2(R)-Hydroxypropyl]amino-3-methyl-N-[2,3,4,5-tetrahydro- 7-methoxy-3-oxo-2-[[2'-hydroxymethyl[1,1'-biphenyl]-4-yl]methyl]-1H- 2-benzazepin-4(R)-yl]butanamide;

3-[2(S),3-Dihydroxypropyl]amino-3-methyl-N-[2,3,4,5-tetrahydro- 7-trifluoromethyl-3-oxo-2-[[2'-hydroxymethyl[1,1'-biphenyl]- 4-yl]-methyl]-1H-2-benzazepin-4(R)-yl]butanamide;

3-Amino-3-methyl-N-[2,3,4,5-tetrahydro-2-[[2'-[[(methylamino)-carbonyl]amino][1,1'-biphenyl]-4-yl]methyl]-3-oxo-1H- 2-benzazepin-(R)-yl]butanamide;

3-[2(R)-Hydroxypropyl]amino-3-methyl-N-[2,3,4,5-tetrahydro-2-[[2'-[(methylamino)carbonyl]amino][1,1'-biphenyl]-4-yl]methyl]-3-oxo- 1H-2-benzazepin-4(R)-yl]butanamide;

3-[2(S),3-Dihydroxypropyl]amino-3-methyl-N-[2,3,4,5-tetrahydro-2-[[2'-[[(methylamino)carbonyl]amino][1, 1'-biphenyl]-4-yl]methyl]-3-oxo- 1H-2-benzazepin-4(R)-yl]butanamide;

2-Amino-2-methyl-N-[2,3,4,5-tetrahydro-7-fluoro-2-[[2'-[[(methyl-amino)carbonyl]amino][1,1'-biphenyl]-4-yl]methyl]-3-oxo-1H- 2-benzazepin-4(R)-yl]propanamide;

3-[2(R)-Hydroxypropyl]amino-3-methyl-N-[2,3,4,5-tetrahydro- 7-fluoro-2-[[2'-[[(methylamino)carbonyl]amino][1,1'-biphenyl]-4-yl]methyl]- 3-oxo-1H-2-benzazepin-4(R)-yl]butanamide;

3-[2(S),3-Dihydroxypropyl]amino-3-methyl-N-[2,3,4,5-tetrahydro- 7-fluoro-2-[[2'-[[(methylamino)carbonyl]amino][1,1'-biphenyl]- 4-yl]-methyl]-3-oxo-1H-2-benzazepin-4(R)-yl]butanamide;

3-Amino-3-methyl-N-[2,3,4,5-tetrahydro-7-methylthio-2-[[2'-[[(methyl-amino)carbonyl]amino][1,1'-biphenyl]-4-yl]methyl]-3-oxo-1H- 2-benzazepin-4(R)-yl]butanamide;

2-Amino-2-methyl-N-[2,3,4,5-tetrahydro-7-methylthio-2-[[2'-[[(methyl-amino)carbonyl]amino][1,1'-biphenyl]-4-yl]methyl]- 3-oxo-1H- 2-benzazepin-4(R)-yl]propanamide;

3-[2(S),3-Dihydroxypropyl]amino-3-methyl-N-[2,3,4,5-tetrahydro- 7-methylthio-2-[[2'-[[(methylamino)carbonyl]amino][1,1'-biphenyl]- 4-yl]-methyl]-3-oxo-1H-2-benzazepin-4(R)-yl]butanamide;

2-Amino-2-methyl-N-[2,3,4,5-tetrahydro-7-methoxy-2-[ [2'-[[(methyl-amino)carbonyl]amino][1,1'-biphenyl]-4-yl]methyl]-3-oxo-1H- 2-benzazepin-4(R)-yl]propanamide;

3-[2(R)-Hydroxypropyl]amino-3-methyl-N-[2,3,4,5-tetrahydro- 7-methoxy-2-[[2'-[[(methylamino)carbonyl]amino][1,1'-biphenyl]- 4-yl]-methyl]-3-oxo-1H-2-benzazepin-4(R)-yl]butanamide;

3-[2(S),3-Dihydroxypropyl]amino-3-methyl-N-[2,3,4,5-tetrahydro- 7-methoxy-2-[[2'-[[(methylamino)carbonyl]amino][1,1'-biphenyl]- 4-yl]-methyl]-3-oxo-1H-2-benzazepin-4(R )-yl]butanamide;

3-[2(R)-Hydroxypropyl]amino-3-methyl-N-[2,3,4,5-tetrahydro-2-[[2'-[(morpholinocarbonyl)amino][1,1'-biphenyl]-4-yl]methyl]-3-oxo-1H- 2-benzazepin-4(R)-yl]butanamide;

3-[2(S),3-Dihydroxypropyl]amino-3-methyl-N-[2,3,4,5-tetrahydro-2-[[2'-[(morpholinocarbonyl)amino][1,1'-biphenyl]-4-yl]methyl]-3-oxo-1H- 2-benzazepin-4(R)-yl]butanamide;

3-[2(R)-Hydroxypropyl]amino-3-methyl-N-[2,3,4,5-tetrahydro-2-[[2'-[[(2-hydroxyethylamino)carbonyl]amino][1,1'-biphenyl]-4-yl]methyl]- 3-oxo-1H-2-benzazepin-4(R)-yl]butanamide;

3-[2(S),3-Dihydroxypropyl]amino-3-methyl-N-[2,3,4,5-tetrahydro-2-[[( 2-hydroxyethylamino)carbonyl]amino][1,1'-biphenyl]-4-yl]methyl]- 3-oxo-1H-2-benzazepin-4(R)-yl]butanamide;

2-Amino-2-methyl-N-[2,3,4,5-tetrahydro-2-[[2'-[[[(methylamino)-carbonyl]amino]methyl][1,1'-biphenyl]-4-yl]methyl]-3-oxo-1H- 2-benzazepin-4(R )-yl]propanamide;

2-Amino-2-methyl-N-[2,3,4,5-tetrahydro-2-[[2'-[[[(methylamino)-carbonyl]amino]methyl][1,1'-biphenyl]-4-yl]methyl]-7-methylthio- 3-oxo-1H-2-benzazepin-4(R)-yl]propanamide;

2-Amino-2-methyl-N-[2,3,4,5-tetrahydro-2-[[2'-[[[(methylamino)-carbonyl]amino]methyl][1,1'-biphenyl]-4-yl]methyl]-7-methoxy- 3-oxo-1H-2-benzazepin-4(R)-yl]propanamide;

2-Amino-2-methyl-N-[2,3,4,5-tetrahydro-2-[[2'-[[[(methylamino)-carbonyl]amino]methyl][1,1'-biphenyl]-4-yl]methyl]-7-fluoro-3-oxo- 1H-2-benzazepin-4(R)-yl]propanamide;

3-Amino-3-methyl-N-[2,3,4,5-tetrahydro-2-[[2'-[[[(methylamino)-carbonyl]amino]methyl][1,1'-biphenyl]-4-yl]methyl]-3-oxo-1H- 2-benzazepin-4(R)-yl]butanamide;

3- Amino-3-methyl-N-[2,3,4,5-tetrahydro-2-[[2' -[[[(methylamino)-carbonyl]amino]methyl][1,1'-biphenyl]-4-yl]methyl]-7-methoxy- 3-oxo-1H-2-benzazepin-4(R)-yl]butanamide;

3-Amino-3-methyl-N-[2,3,4,5-tetrahydro-2-[[2'-[[[(methylamino)-carbonyl]amino]methyl][1,1'-biphenyl]-4-yl]methyl]- 7-trifluoromethyl-3-oxo-1H-2-benzazepin-4(R )-yl]butanamide;

3-[2(R)-Hydroxypropyl]amino-3-methyl-N-[2,3,4,5-tetrahydro-2-[[2'-[[[(methylamino)carbonyl]amino]methyl][1,1'-biphenyl]-4-yl]methyl]- 3-oxo-1H-2-benzazepin-4(R)-yl]butanamide;

3-[2(R)-Hydroxypropyl]amino-3-methyl-N-[2,3,4,5-tetrahydro-2-[[2'-[[[(methylamino)carbonyl]amino]methyl][1,1'-biphenyl]-4-yl]methyl]- 7-methylthio-3-oxo-1H-2-benzazepin-4(R)-yl]butanamide;

3-[2(R)-Hydroxypropyl]amino-3-methyl-N-[2,3,4,5-tetrahydro-2-[[2'-[[[(methylamino)carbonyl]amino]methyl][1,1'-biphenyl]-4-yl]methyl]- 7-fluoro-3-oxo-1H-2-benzazepin-4(R)-yl]butanamide;

3-[2(S),3-Dihydroxypropyl]amino-3-methyl-N-[2,3,4,5-tetrahydro-2-[[2'-[[[(methylamino)carbonyl]amino]methyl][1,1'-biphenyl]-4-yl]methyl]- 3-oxo-1H-2-benzazepin-4(R)-yl]butanamide;

3-[2(S),3-Dihydroxypropyl]amino-3-methyl-N-[2,3,4,5-tetrahydro-2-[[2'-[[[(methylamino)carbonyl]amino]methyl][1,1'-biphenyl]-4-yl]methyl]- 7-methoxy-3-oxo-1H-2-benzazepin-4(R)-yl]butanamide;

3-[2(S),3-Dihydroxypropyl]amino-3-methyl-N-[2,3,4,5-tetrahydro-2-[[2'-[[[(methylamino)carbonyl]amino]methyl][1,1'-biphenyl]-4-yl]methyl]- 7-trifluoromethyl-3-oxo-1H-2-benzazepin-4(R)-yl]butanamide;

2-Amino-2-methyl-N-[2,3,4,5-tetrahydro-2-[[2'-[[(aminocarbonyl)-amino]methyl][1,1'-biphenyl]-4-yl]methyl]-3-oxo-1H- 2-benzazepin-4(R)-yl]propanamide;

2-Amino-2-methyl-N-[2,3,4,5-tetrahydro-2-[[2'-[[(aminocarbonyl)-amino]methyl][1,1'-biphenyl]-4-yl]methyl]-7-methylthio-3-oxo-1H- 2-benzazepin-4(R)-yl]propanamide;

3- Amino-3-methyl-N-[2,3,4,5-tetrahydro-2-[[2'-[[(aminocarbonyl)-amino]methyl][1,1'-biphenyl]-4-yl]methyl]-3-oxo-1H-2-benzazepin- 4(R)-yl]butanamide;

3-Amino-3-methyl-N-[2,3,4,5-tetrahydro-2-[[2'-[[(aminocarbonyl)-amino]methyl][1,1'-biphenyl]-4-yl]methyl]-7-methylthio-3-oxo-1H- 2-benzazepin-4(R)-yl]butanamide;

3-Amino-3-methyl-N-[2,3,4,5-tetrahydro-2-[[2'-[[(aminocarbonyl)-amino]methyl][1,1'-biphenyl]-4-yl]methyl]-7-fluoro-3-oxo-1H- 2-benzazepin-4(R)-yl]butanamide;

3-[2(R)-Hydroxypropyl]amino-3-methyl-N-[2,3,4,5-tetrahydro-2-[[2'-[[(aminocarbonyl)amino]methyl][1,1'-biphenyl]-4-yl]methyl]-3-oxo- 1H-2-benzazepin-4(R)-yl]butanamide;

3-[2(R)-Hydroxypropyl]amino-3-methyl-N-[2,3,4,5-tetrahydro-2-[[2'-[[(aminocarbonyl)amino]methyl][1,1'-biphenyl]-4-yl]methyl]- 7-methylthio-3-oxo-1H-2-benzazepin-4(R)-yl]butanamide;

3-[2(R)-Hydroxypropyl]amino-3-methyl-N-[2,3,4,5-tetrahydro-2-[[2'-[[(aminocarbonyl)amino]methyl][1,1'-biphenyl]-4-yl]methyl]-7-fluoro- 3-oxo-1H-2-benzazepin-4(R)-yl]butanamide;

3-[2(S),3-Dihydroxypropyl]amino-3-methyl-N-[2,3,4,5-tetrahydro-2-[[2'-[[(aminocarbonyl)amino]methyl][1,1'-biphenyl]-4-yl]methyl]-3-oxo- 1H-2-benzazepin-4(R)-yl]butanamide;

3-[2(S),3-Dihydroxypropyl]amino-3-methyl-N-[2,3,4,5-tetrahydro-2-[[2'-[[(aminocarbonyl)amino]methyl][1,1'-biphenyl]-4-yl]methyl]- 7-methoxy-3-oxo-1H-2-benzazepin-4(R)-yl]butanamide;

3-[2(S),3-Dihydroxypropyl]amino-3-methyl-N-[2,3,4,5-tetrahydro-2-[[2'-[[(aminocarbonyl)amino]methyl][1,1'-biphenyl]-4-yl]methyl]-7-fluoro- 3-oxo-1H-2-benzazepin-4(R)-yl]butanamide;

2-Amino-2-methyl-N-[2,3,4,5-tetrahydro-2-[[2'-[[[(ethylamino)-carbonyl]amino]methyl][1,1'-biphenyl]-4-yl]methyl]-3-oxo-1H- 2-benzazepin-4(R )-yl]propanamide;

2-Amino-2-methyl-N-[2,3,4,5-tetrahydro-2-[[2'-[[[(ethylamino)-carbonyl]amino]methyl][1,1'-biphenyl]-4-yl]methyl]-7-methylthio- 3-oxo-1H-2-benzazepin-4(R)-yl]propanamide;

2-Amino-2-methyl-N-[2,3,4,5-tetrahydro-2-[[2'-[[[(ethylamino)-carbonyl]amino]methyl][1,1'-biphenyl]-4-yl]methyl]-7-fluoro-3-oxo- 1H-2-benzazepin-4(R)-yl]propanamide;

3-Amino-3-methyl-N-[2,3,4,5-tetrahydro-2-[[2'-[[[(ethylamino)-carbonyl]amino]methyl][1,1'-biphenyl]-4-yl]methyl]-3-oxo-1H- 2-benzazepin-4(R)-yl]butanamide;

3-Amino-3-methyl-N-[2,3,4,5-tetrahydro-2-[[2'-[[[(ethylamino)-carbonyl]amino]methyl][1,1'-biphenyl]-4-yl]methyl]-7-methoxy- 3-oxo-1H-2-benzazepin-4(R)-yl]butanamide;

3-Amino-3-methyl-N-[2,3,4,5-tetrahydro-2-[[2'-[[[(ethylamino)-carbonyl]amino]methyl][1,1'-biphenyl]-4-yl]methyl]-7-fluoro-3-oxo- 1H-2-benzazepin-4(R)-yl]butanamide;

3-[2(R)-Hydroxypropyl]amino-3-methyl-N-[2,3,4,5-tetrahydro-2-[[2'-[[[(ethylamino)carbonyl]amino]methyl][1,1'-biphenyl]-4-yl]methyl]- 3-oxo-1H-2-benzazepin-4(R)-yl]butanamide;

3-[2(R)-Hydroxypropyl]amino-3-methyl-N-[2,3,4,5-tetrahydro-2-[[2'-[[[(ethylamino)carbonyl]amino]methyl][1,1'-biphenyl]-4-yl]methyl]- 7-methylthio-3-oxo-1H-2-benzazepin-4(R)-yl]butanamide;

3-[2(R)-Hydroxypropyl]amino-3-methyl-N-[2,3,4,5-tetrahydro-2-[[2'-[[[(ethylamino)carbonyl]amino]methyl][1,1'-biphenyl]-4-yl]methyl]- 7-methoxy-3-oxo-1H-2-benzazepin-4(R)-yl]butanamide;

3-[2(R)-Hydroxypropyl]amino-3-methyl-N-[2,3,4,5-tetrahydro-2-[[2'-[[[(ethylamino)carbonyl]amino]methyl][1,1'-biphenyl]-4-yl]methyl]- 7-fluoro-3-oxo-1H-2-benzazepin-4(R )-yl]butanamide;

3-[2(S),3-Dihydroxypropyl]amino-3-methyl-N-[2,3,4,5-tetrahydro-2-[[2'-[[[(ethylamino)carbonyl]amino]methyl][1,1'-biphenyl]-4-yl]methyl]- 3-oxo-1H-2-benzazepin-4(R)-yl]butanamide;

3-[2(S),3-Dihydroxypropyl]amino-3-methyl-N-[2,3,4,5-tetrahydro-2-[[2'-[[[(ethylamino)carbonyl]amino]methyl][1,1'-biphenyl]-4-yl]methyl]- 7-methylthio-3-oxo-1H-2-benzazepin-4(R)-yl]butanamide;

3-[2(S),3-Dihydroxypropyl]amino-3-methyl-N-[2,3,4,5-tetrahydro-2-[[2'-[[[(ethylamino)carbonyl]amino]methyl][1,1'-biphenyl]-4-yl]methyl]- 7-methoxy-3-oxo-1H-2-benzazepin-4(R)-yl]butanamide;

3-[2(S),3-Dihydroxypropyl]amino-3-methyl-N-[2,3,4,5-tetrahydro-2-[[2'-[[[(ethylamino)carbonyl]amino]methyl][1,1'-biphenyl]-4-yl]methyl]- 7-fluoro-3-oxo-1H-2-benzazepin-4(R)-yl]butanamide;

2-Amino-2-methyl-N-[2,3,4,5-tetrahydro-2-[[2'-[[[[(2-hydroxyethyl)-amino]carbonyl]amino]methyl][1,1'-biphenyl]-4-yl]methyl]-3-oxo-1H- 2-benzazepin-4(R)-yl]propanamide;

2-Amino-2-methyl-N-[2,3,4,5-tetrahydro-2-[[2'-[[[[(2-hydroxyethyl)-amino]carbonyl]amino]methyl][1,1'-biphenyl]-4-yl]methyl]- 7-methyl-thio-3-oxo-1H-2-benzazepin-4(R)-yl]propanamide;

2-Amino-2-methyl-N-[2,3,4,5-tetrahydro-2-[[2'-[[[[(2-hydroxyethyl)-amino]carbonyl]amino]methyl][1,1'-biphenyl]-4-yl]methyl]- 7-methoxy-3-oxo-1H-2-benzazepin-4(R )-yl]propanamide;

2-Amino-2-methyl-N-[2,3,4,5-tetrahydro-2-[[2'-[[[[(2-hydroxyethyl)-amino]carbonyl]amino]methyl][1,1'-biphenyl]-4-yl]methyl]-7-fluoro- 3-oxo-1H-2-benzazepin-4(R )-yl]propanamide;

3-Amino-3-methyl-N-[2,3,4,5-tetrahydro-2-[[2'-[[[[(2-hydroxyethyl)-amino]carbonyl]amino]methyl][1,1'-biphenyl]-4-yl]methyl]-3-oxo-1H- 2-benzazepin-4(R)-yl]butanamide;

3-Amino-3-methyl-N-[2,3,4,5-tetrahydro-2-[[2'-[[[[(2-hydroxyethyl)-amino]carbonyl]amino]methyl][1,1'-biphenyl]-4-yl]methyl]- 7-methyl-thio-3-oxo-1H-2-benzazepin-4(R)-yl]butanamide;

3-Amino-3-methyl-N-[2,3,4,5-tetrahydro-2-[[2'-[[[[(2-hydroxyethyl)-amino]carbonyl]amino]methyl][1,1'-biphenyl]-4-yl]methyl]- 7-methoxy-3-oxo-1H-2-benzazepin-4(R)-yl]butanamide;

3-Amino-3-methyl-N-[2,3,4,5-tetrahydro-2-[[2'-[[[[(2-hydroxyethyl)-amino]carbonyl]amino]methyl][1,1'-biphenyl]-4-yl]methyl]-7-fluoro- 3-oxo-1H-2-benzazepin-4(R)-yl]butanamide;

3-[2(R)- Hydroxypropyl]amino-3-methyl-N-[2,3,4,5-tetrahydro-2-[[2'-[[[[(2-hydroxyethyl)amino]carbonyl]amino]methyl][1,1'-biphenyl]- 4-yl]-methyl]-3-oxo-1H-2-benzazepin-4(R)-yl]butanamide;

3-[2(R)-Hydroxypropyl]amino-3-methyl-N-[2,3,4,5-tetrahydro-2-[[2'-[[[[(2-hydroxyethyl)amino]carbonyl]amino]methyl][1,1'-biphenyl]- 4-yl]-methyl]-7-methylthio-3-oxo-1H-2-benzazepin-4(R)-yl]butanamide;

3-[2(R)-Hydroxypropyl]amino-3-methyl-N-[2,3,4,5-tetrahydro-2-[[2'-[[[[(2-hydroxyethyl)amino]carbonyl]amino]methyl][1,1'-biphenyl]- 4-yl]-methyl]-7-methoxy-3-oxo-1H-2-benzazepin-4(R)-yl]butanamide;

3-[2(R)-Hydroxypropyl]amino-3-methyl-N-[2,3,4,5-tetrahydro-2-[[2'-[[[[(2-hydroxyethyl)amino]carbonyl]amino]methyl][1,1'-biphenyl]- 4-yl]-methyl]-7-fluoro-3-oxo-1H-2-benzazepin-4(R)-yl]butanamide;

3-[2(S),3-Dihydroxypropyl]amino-3-methyl-N-[2,3,4,5-tetrahydro-2-[[2'-[[[[(2-hydroxyethyl)amino]carbonyl]amino]methyl][1,1'-biphenyl]- 4-yl]methyl]-3-oxo-1H-2-benzazepin-4(R)-yl]butanamide;

3-[2(S),3-Dihydroxypropyl]amino-3-methyl-N-[2,3,4,5-tetrahydro-2-[[2'-[[[[(2-hydroxyethyl)amino]carbonyl]amino]methyl][1,1'-biphenyl]- 4-yl]methyl]-7-methylthio-3-oxo-1H-2-benzazepin-4(R)-yl]butanamide;

3-[2(S),3-Dihydroxypropyl]amino-3-methyl-N-[2,3,4,5-tetrahydro-2-[[2'-[[[[(2-hydroxyethyl)amino]carbonyl]amino]methyl][1,1'-biphenyl]- 4-yl]methyl]-7-methoxy-3-oxo-1H-2-benzazepin-4(R)-yl]butanamide;

3-[2(S),3-Dihydroxypropyl]amino-3-methyl-N-[2,3,4,5-tetrahydro-2-[[2'-[[[[(2-hydroxyethyl)amino]carbonyl]amino]methyl][1,1'-biphenyl]- 4-yl]methyl]-7-fluoro-3-oxo-1H-2-benzazepin-4(R)-yl]butanamide;

2-Amino-2- methyl-N-[2,3,4,5-tetrahydro-2-[[(methylamino)carbonyl ]-amino]prop-2-yl][1,1'-biphenyl]-4-yl]methyl]-3-oxo-1H-2-benzazepin- 4(R)-yl]propanamide;

2-Amino-2-methyl-N-[2,3,4,5-tetrahydro-2-[[2'-[1-[[(methylamino)-carbonyl]amino]ethyl][1,1'-biphenyl]-4-yl]methyl]-3-oxo-1H-2-benzazepin- 4(R)-yl]propanamide;

2-Amino-2-methyl-N-[2,3,4,5-tetrahydro-2-[[2'-[[(methoxycarbonyl)-amino]methyl][1,1'-biphenyl]-4-yl]methyl]-3-oxo-1H- 2-benzazepin-(R)-yl]propanamide;

3-Amino-3-methyl-N-[2,3,4,5-tetrahydro-2-[[2'-[[(methoxycarbonyl)-amino]methyl][1,1'-biphenyl]-4-yl]methyl]-3-oxo-1H- 2-benzazepin-(R)-yl]butanamide;

3-[2(R)-Hydroxypropyl]amino-3-methyl-N-[2,3,4,5-tetrahydro-2-[[2'-[(methoxycarbonyl)amino]methyl][1,1'-biphenyl]-4-yl]methyl]- 3-oxo-H-2-benzazepin-4(R)-yl]butanamide;

3-[2(S),3-Dihydroxypropyl]amino-3-methyl-N-[2,3,4,5-tetrahydro-2-[[2'-[(methoxycarbonyl)amino]methyl][1,1'-biphenyl]-4-yl]methyl]- 3-oxo-H-2-benzazepin-4(R )-yl]butanamide;

2-Amino-2-methyl-N-[2,3,4,5-tetrahydro-3-oxo-4-[[2'-(1H-tetrazol- 5-yl)[1,1'-biphenyl]-4-yl]methyl]-1,4-benzothiazepin-2(R)-yl]-propanamide;

3-Amino-3-methyl-N-[2,3,4,5-tetrahydro-3-oxo-4-[[2'-(1H-tetrazol- 5-yl)[1,1'-biphenyl]-4-yl]methyl]-1,4-benzothiazepin-2(R)-yl]butanamide;

3-[2(R)-Hydroxypropyl]amino-3-methyl-N-[2,3,4,5-tetrahydro-3-oxo- 4-[2'-(1H-tetrazol-5-yl)[1,1'-biphenyl]-4-yl]methyl]- 1,4-benzothiazepin-(R)-yl]butanamide;

3-[2(S),3-Dihydroxypropyl]amino-3-methyl-N-[2,3,4,5-tetrahydro- 3-oxo-4-[[2'-(1H-tetrazol-5-yl)[1,1'-biphenyl]-4-yl]methyl]- 1,4-benzothiazepin-(R)-yl]butanamide;

3-[2(R)-Hydroxypropyl]amino-3-methyl-N-[2,3,4,5-tetrahydro- 8-methoxy-3-oxo-4-[[2'-(1H-tetrazol-5-yl)[1,1'-biphenyl]- 4-yl]methyl]-1,4-benzothiazepin-2(R)-yl]butanamide;

3-[2(S),3-Dihydroxypropyl]amino-3-methyl-N-[2,3,4,5-tetrahydro- 8-methoxy-3-oxo-4-[[2'-(1H-tetrazol-5-yl)[1,1'-biphenyl]- 4-yl]methyl]-1,4-benzothiazepin-2(R)-yl]butanamide;

2-Amino-2-methyl-N-[2,3,4,5-tetrahydro-8-fluoro-3-oxo-4-[[2'-( 1H-tetrazol-5-yl)[1,1'-biphenyl]-4-yl]methyl]-1,4-benzothiazepin-2(R)-yl]-propanamide;

3-[2(S),3-Dihydroxypropyl]amino-3-methyl-N-[2,3,4,5-tetrahydro- 8-fluoro-3-oxo-4-[[2'-(1H-tetrazol-5-yl)[1,1'-biphenyl]- 4-yl]methyl]-1,4-benzothiazepin-2(R)-yl]butanamide;

3-Amino-3-methyl-N-[2,3,4,5-tetrahydro-8-methylthio-3-oxo-4-[[2'-( 1H-tetrazol-5-yl)[1,1'-biphenyl]-4-yl]methyl]- 1,4-benzothiazepin- 2(R)-yl]butanamide;

3-[2(R)-Hydroxypropyl]amino-3-methyl-N-[2,3,4,5-tetrahydro- 8-methylthio-3-oxo-4-[[2'-(1H-tetrazol-5-yl)[1,1'-biphenyl]- 4-yl]methyl]-1,4-benzothiazepin-2(R)-yl]butanamide;

N-Ethyl-4'-[[2(R)-[(2-amino-2-methyl-1-oxopropyl)amino]- 2,3,4,5-tetrahydro-3-oxo-1,4-benzothiazepin-4-yl]methyl][1,1'-biphenyl]-2-carboxamide;

N-Ethyl-4'-[[2(R)-[[[[2(S),3-dihydroxypropyl]amino]-3-methyl- 1-oxobutyl]amino]-2,3,4,5-tetrahydro-3-oxo-1,4-benzothiazepin- 4-yl]-methyl][1,1'-biphenyl]-2-carboxamide;

N-Ethyl-4'-[[2(R)-[[[[2(R)-hydroxypropyl]amino]-3-methyl- 1-oxobutyl]-amino]-2,3,4,5-tetrahydro-8-fluoro-3-oxo- 1,4-benzothiazepin- 4-yl]-methyl][1,1'-biphenyl]-2-carboxamide;

N-Ethyl-4'-[[2(R)-[[[[2(S),3-dihydroxypropyl]amino]-3-methyl- 1-oxo-butyl)amino]-2,3,4,5-tetrahydro-8-fluoro-3-oxo-1,4-benzothiazepin- 4-yl]methyl][1,1'-biphenyl]-2-carboxamide;

N-Ethyl-4'-[[2(R)-[(2-amino-2-methyl-1-oxopropyl)amino]- 2,3,4,5-tetrahydro-8-methoxy-3-oxo-1,4-benzothiazepin-4-yl]methyl][1,1'-biphenyl]-2-carboxamide;

N-Ethyl-4'-[[2(R)-[[[[2(S),3-dihydroxypropyl]amino]-3-methyl- 1-oxobutyl)amino]-2,3,4,5-tetrahydro-8-methoxy-3-oxo- 1,4-benzothiazepin-4-yl]methyl][1,1'-biphenyl]-2-carboxamide;

N-Ethyl-4'-[[2(R)-[(2-amino-2-methyl-1-oxopropyl)amino]- 2,3,4,5-tetrahydro-8-methylthio-3-oxo-1,4-benzothiazepin-4-yl]methyl][1,1'-biphenyl]-2-carboxamide;

N-Ethyl-4'-[[2(R)-[[[[2(R)-hydroxypropyl]amino]-3-methyl- 1-oxo-butyl]amino]-2,3,4,5-tetrahydro-8-methylthio-3-oxo- 1,4-benzothiazepin-4-yl]methyl][1,1'-biphenyl]-2-carboxamide;

N-Ethyl-4'-[[2(R)-[[[[2(S),3-dihydroxypropyl]amino]-3-methyl- 1-oxo-butyl)amino]-2,3,4,5-tetrahydro-8-methylthio-3-oxo- 1,4-benzothiazepin-4-yl]methyl][1,1'-biphenyl]-2-carboxamide;

2-Amino-2-methyl-N-[2,3,4,5-tetrahydro-3-oxo-4-[[2'-hydroxymethyl-[1,1'-biphenyl]-4-yl]methyl]-1,4-benzothiazepin-2(R)-yl]propanamide;

3-[2(S),3-Dihydroxypropyl]amino-3-methyl-N-[2,3,4,5-tetrahydro- 3-oxo-4-[[2'-hydroxymethyl[1,1'-biphenyl]-4-yl]methyl]- 1,4-benzothiazepin-(R)-yl]butanamide;

3-Amino-3-methyl-N-[2,3,4,5-tetrahydro-8-methylthio-3-oxo-4-[[2'-hydroxymethyl[1,1'-biphenyl]-4-yl]methyl]-1,4-benzothiazepin-2(R)-yl]-butanamide;

3-[2(R)-Hydroxypropyl]amino-3-methyl-N-[2,3,4,5-tetrahydro- 8-trifluoromethyl-3-oxo-4-[[2'-hydroxymethyl[1,1'-biphenyl]- 4-yl]-methyl]-1,4-benzothiazepin-2(R)-yl]butanamide;

3-Amino-3-methyl-N-[2,3,4,5-tetrahydro-4-[[2'-[[(methylamino)-carbonyl]amino][1,1'-biphenyl]-4-yl]methyl]-3-oxo-1,4-benzothiazepin- 2(R)-yl]butanamide;

3-[2(R)-Hydroxypropyl]amino-3-methyl-N-[2,3,4,5-tetrahydro-4-[[2'-[(methylamino)carbonyl]amino][1,1'-biphenyl]-4-yl]methyl]-3-oxo- 1,4-benzothiazepin-2(R)-yl]butanamide;

3-[2(S),3-Dihydroxypropyl]amino-3-methyl-N-[2,3,4,5-tetrahydro-4-[[2'-[[(methylamino)carbonyl]amino][1,1'-biphenyl]-4-yl]methyl]-3-oxo- 1,4-benzothiazepin-2(R)-yl]butanamide;

3-Amino-3-methyl-N-[2,3,4,5-tetrahydro-8-methylthio-4-[[2'-[[(methyl-amino)carbonyl]amino][1,1'-biphenyl]-4-yl]methyl]-3-oxo-1,4-benzothiazepin- 2(R)-yl]butanamide;

3-[2(R)-Hydroxypropyl]amino-3-methyl-N-[2,3,4,5-tetrahydro- 8-methylthio-4-[[2'-[[(methylamino)carbonyl]amino][1,1'-biphenyl]- 4-yl]-methyl]-3-oxo-1,4-benzothiazepin-2(R)-yl]butanamide;

3-[2(S),3-Dihydroxypropyl]amino-3-methyl-N-[2,3,4,5-tetrahydro- 8-methylthio-4-[[2'-[[(methylamino)carbonyl]amino][1,1'-biphenyl]- 4-yl]-methyl]-3-oxo-1,4-benzothiazepin-2(R)-yl]butanamide;

3- Amino-3-methyl-N-[2,3,4,5-tetrahydro-8-methoxy-4-[[2'-[[(methyl-amino)carbonyl]amino][1,1'-biphenyl]-4-yl]methyl]-3-oxo- 1,4-benzothiazepin-2(R)-yl]butanamide;

3-[2(R)-Hydroxypropyl]amino-3-methyl-N-[2,3,4,5-tetrahydro- 8-methoxy-4-[[2'-[[(methylamino)carbonyl]amino][1,1'-biphenyl]- 4-yl]-methyl]-3-oxo-1,4-benzothiazepin-2(R)-yl]butanamide;

3-[2(S),3-Dihydroxypropyl]amino-3-methyl-N-[2,3,4,5-tetrahydro- 8-methoxy-4-[[2'-[[(methylamino)carbonyl]amino][1,1'-biphenyl]- 4-yl]-methyl]-3-oxo-1,4-benzothiazepin-2(R )-yl]butanamide;

3- Amino-3-methyl-N-[2,3,4,5-tetrahydro-8-fluoro-4-[[2'-[[(methyl-amino)carbonyl]amino][1,1'-biphenyl]- 4-yl]methyl]-3-oxo- 1,4-benzothiazepin-2(R)-yl]butanamide;

3-[2(R)-Hydroxypropyl]amino-3-methyl-N-[2,3,4,5-tetrahydro- 8-fluoro-4-[[2'-[[(methylamino)carbonyl]amino][1,1'-biphenyl]-4-yl]methyl]- 3-oxo-1,4-benzothiazepin-2(R)-yl]butanamide;

3-[2(S),3-Dihydroxypropyl]amino-3-methyl-N-[2,3,4,5-tetrahydro- 8-fluoro-4-[[2'-[[(methylamino)carbonyl]amino][1,1'-biphenyl]- 4-yl]-methyl]-3-oxo-1,4-benzothiazepin-2(R)-yl]butanamide;

2-Amino-2-methyl-N-[2,3,4,5-tetrahydro-4-[[2'-[(morpholinocarbonyl)-amino][1,1'-biphenyl]-4-yl]methyl]- 3-oxo-1,4-benzothiazepin-2(R)-yl]-propanamide;

3-Amino-3-methyl-N-[2,3,4,5-tetrahydro-4-[[2'-[(morpholinocarbonyl)-amino][1,1'-biphenyl]-4-yl]methyl]- 3-oxo-1,4-benzothiazepin- 2(R)-yl]-butanamide;

3-[2(R)-Hydroxypropyl]amino-3-methyl-N-[2,3,4,5-tetrahydro-4-[[2'-[(morpholinocarbonyl)amino][1,1'-biphenyl]-4-yl]methyl]-3-oxo- 1,4-benzothiazepin-2(R)-yl]butanamide;

3-[2(S),3-Dihydroxypropyl]amino-3-methyl-N-[2,3,4,5-tetrahydro-4-[[2'-[(morpholinocarbonyl)amino][1,1'-biphenyl]-4-yl]methyl]-3-oxo- 1,4-benzothiazepin-2(R)-yl]butanamide;

3-[2(R)-Hydroxypropyl]amino-3-methyl-N-[2,3,4,5-tetrahydro- 8-methylthio-4-[[2'-[(morpholinocarbonyl)amino][1,1'-biphenyl]- 4-yl]methyl]-3-oxo-1,4-benzothiazepin-2(R)-yl]butanamide;

3-[2(S),3-Dihydroxypropyl]amino-3-methyl-N-[2,3,4,5-tetrahydro- 8-methylthio-4-[[2'-[(morpholinocarbonyl)amino][1,1'-biphenyl]- 4-yl]-methyl]-3-oxo-1,4-benzothiazepin-2(R)-yl]butanamide;

3-Amino-3-methyl-N-[2,3,4,5-tetrahydro-8-methoxy-4-[[2'-[(morpholinocarbonyl)amino][1,1'-biphenyl]-4-yl]methyl]-3-oxo- 1,4-benzothiazepin-2(R)-yl]butanamide;

3-[2(R)-Hydroxypropyl]amino-3-methyl-N-[2,3,4,5-tetrahydro- 8-methoxy-4-[[2'-[(morpholinocarbonyl)amino][1,1'-biphenyl]- 4-yl]-methyl]-3-oxo-1,4-benzothiazepin-2(R)-yl]butanamide;

3-[2(S),3-Dihydroxypropyl]amino-3-methyl-N-[2,3,4,5-tetrahydro- 8-methoxy-4-[[2'-[(morpholinocarbonyl)amino][1,1'-biphenyl]- 4-yl]-methyl]-3-oxo-1,4-benzothiazepin-2(R)-yl]butanamide;

3-Amino-3-methyl-N-[2,3,4,5-tetrahydro-8-fluoro-4-[[2'-[(morpholinocarbonyl)amino][1,1'-biphenyl]-4-yl]methyl]-3-oxo- 1,4-benzothiazepin-2(R)-yl]butanamide;

3-[2(R)-Hydroxypropyl]amino-3-methyl-N-[2,3,4,5-tetrahydro- 8-fluoro-4-[[2'-[(morpholinocarbonyl)amino][1,1'-biphenyl]-4-yl]methyl]- 3-oxo-1,4-benzothiazepin-2(R)-yl]butanamide;

3-[2(S),3-Dihydroxypropyl]amino-3-methyl-N-[2,3,4,5-tetrahydro- 8-fluoro-4-[[2'-[(morpholinocarbonyl)amino][1,1'-biphenyl]- 4-yl]methyl]-3-oxo-1,4-benzothiazepin-2(R)-yl]butanamide;

2- Amino-2-methyl-N-[2,3,4,5-tetrahydro-4[[2'-[[( 2-hydroxyethyl-amino)carbonyl]amino][1,1'-biphenyl]-4-yl]methyl]-3-oxo- 1,4-benzothiazepin-2(R)-yl]propanamide;

3- Amino-3-methyl-N-[2,3,4,5-tetrahydro-4-[[2'-[[( 2-hydroxyethyl-amino)carbonyl]amino][1,1'-biphenyl]-4-yl]methyl]-3-oxo- 1,4-benzo-thiazepin-2(R)-yl]butanamide;

3-[2(R)-Hydroxypropyl]amino-3-methyl-N-[2,3,4,5-tetrahydro-4-[[2'-[[(2-hydroxyethylamino)carbonyl] amino][1,1'-biphenyl]-4-yl]methyl]- 3-oxo-1,4-benzothiazepin-2(R)-yl]butanamide;

3-[2(S),3-Dihydroxypropyl]amino-3-methyl-N-[2,3,4,5-tetrahydro-4-[[2'-[[(2-hydroxyethylamino)carbonyl] amino][1,1'-biphenyl]-4-yl]methyl]- 3-oxo-1,4-benzothiazepin-2(R)-yl]butanamide;

3-Amino-3-methyl-N-[2,3,4,5-tetrahydro-8-methylthio-4-[[2'-[[( 2-hydroxyethylamino)carbonyl]amino][1,1'-biphenyl]-4-yl]methyl]- 3-oxo-1,4-benzothiazepin-2(R)-yl]butanamide;

3-[2(R)-Hydroxypropyl]amino-3-methyl-N-[2,3,4,5-tetrahydro- 8-methylthio-4-[[2'-[[(2-hydroxyethylamino)carbonyl]amino][1,1'-biphenyl]-4-yl]methyl]-3-oxo-1,4-benzothiazepin-2(R)-yl]butanamide;

3-[2(S),3-Dihydroxypropyl]amino-3-methyl-N-[2,3,4,5-tetrahydro- 8-methylthio-4-[[2'-[[(2-hydroxyethylamino)carbonyl]amino][1,1'-biphenyl]-4-yl]methyl]-3-oxo-1,4-benzothiazepin-2(R)-yl]butanamide;

3-Amino-3-methyl-N-[2,3,4,5-tetrahydro-8-methoxy-4-[ [2'-[[( 2-hydroxyethylamino)carbonyl]amino][1,1'-biphenyl]-4-yl]methyl]- 3-oxo-1,4-benzothiazepin-2(R)-yl]butanamide;

3-[2(R)-Hydroxypropyl]amino-3-methyl-N-[2,3,4,5-tetrahydro- 8-methoxy-4-[[2'-[[(2-hydroxyethylamino)carbonyl]amino][1,1'-biphenyl]-4-yl]methyl]-3-oxo-1,4-benzothiazepin-2(R)-yl]butanamide;

3-[2(S),3-Dihydroxypropyl]amino-3-methyl-N-[2,3,4,5-tetrahydro- 8-methoxy-4-[[2'-[[(2-hydroxyethylamino)carbonyl]amino][1,1'-biphenyl]-4-yl]methyl]-3-oxo-1,4-benzothiazepin-2(R)-yl]butanamide;

3-Amino-3-methyl-N-[2,3,4,5-tetrahydro-8-fluoro-4-[ [2'-[[( 2-hydroxy-ethylamino)carbonyl]amino][1,1'-biphenyl]-4-yl]methyl]-3-oxo- 1,4-benzothiazepin-2(R)-yl]butanamide;

3-[2(R)-Hydroxypropyl]amino-3-methyl-N-[2,3,4,5-tetrahydro- 8-fluoro-4-[[2'-[[(2-hydroxyethylamino)carbonyl]amino][1,1'-biphenyl]- 4-yl]methyl]-3-oxo-1,4-benzothiazepin-2(R)-yl]butanamide;

3-[2(S),3-Dihydroxypropyl]amino-3-methyl-N-[2,3,4,5-tetrahydro- 8-fluoro-4-[[2'-[[(2-hydroxyethylamino)carbonyl]amino][1,1'-biphenyl]- 4-yl]methyl]-3-oxo-1,4-benzothiazepin-2(R)-yl]butanamide;

2-Amino-2-methyl-N-[2,3,4,5-tetrahydro-4-[[2'-[[[(methylamino)-carbonyl]amino]methyl][1,1'-biphenyl]-4-yl]methyl]-3-oxo- 1,4-benzo-thiazepin-2(R)-yl]propanamide;

3-Amino-3-methyl-N-[2,3,4,5-tetrahydro-4-[[2'-[[[(methylamino)-carbonyl]amino]methyl][1,1'-biphenyl]-4-yl]methyl]-3-oxo- 1,4-benzo-thiazepin-2(R)-yl]butanamide;

3-[2(S),3-Dihydroxypropyl]amino-3-methyl-N-[2,3,4,5-tetrahydro-4-[[2'-[[[(methylamino)carbonyl]amino]methyl][1,1'-biphenyl]-4-yl]methyl]- 3-oxo-1,4-benzothiazepin-2(R)-yl]butanamide;

3-[2(R)-Hydroxypropyl]amino-3-methyl-N-[2,3,4,5-tetrahydro-4-[[2'-[[[(methylamino)carbonyl]amino]methyl][1,1'-biphenyl]-4-yl]methyl]- 3-oxo-1,4-benzothiazepin-2(R)-yl]butanamide;

2-Amino-2-methyl-N-[2,3,4,5-tetrahydro-8-fluoro-4-[[2'-[[[(methyl-amino)carbonyl]amino]methyl][1,1'-biphenyl]-4-yl]methyl]-3-oxo- 1,4-benzothiazepin-2(R)-yl]propanamide;

3-Amino-3-methyl-N-[2,3,4,5-tetrahydro-8-fluoro-4-[[2'-[[[(methyl-amino)carbonyl]amino]methyl][1,1'-biphenyl]-4-yl]methyl]-3-oxo- 1,4-benzothiazepin-2(R)-yl]butanamide;

3-[2(S),3-Dihydroxypropyl]amino-3-methyl-N-[2,3,4,5-tetrahydro- 8-fluoro-4-[[2'-[[[(methylamino)carbonyl]amino]methyl][1,1'-biphenyl]- 4-yl]methyl]-3-oxo-1, 4-benzothiazepin-2(R)-yl]butanamide;

3-[2(R)-Hydroxypropyl]amino-3-methyl-N-[2,3,4,5-tetrahydro-8-fluoro- 4-[[2'-[[[(methylamino)carbonyl]amino]methyl][1,1'-biphenyl]- 4-yl]methyl]-3-oxo-1, 4-benzothiazepin-2(R)-yl]butanamide;

2-Amino-2-methyl-N-[2,3,4,5-tetrahydro-8-methoxy-4-[ [2'-[[[(methyl-amino)carbonyl]amino]methyl][1,1'-biphenyl]-4-yl]methyl]-3-oxo- 1,4-benzothiazepin-2(R )-yl]propanamide;

3-[2(R)-Hydroxypropyl]amino-3-methyl-N-[2,3,4,5-tetrahydro- 8-methoxy-4-[[2'-[[[(methylamino)carbonyl]amino]methyl][1,1'-biphenyl]-4-yl]methyl]-3-oxo-1,4-benzothiazepin-2(R)-yl]butanamide;

2-Amino-2-methyl-N-[2,3,4,5-tetrahydro-8-methylthio-4-[[2'-[[[(methylamino)carbonyl]amino]methyl][1,1'-biphenyl]-4-yl]methyl]- 3-oxo-1,4-benzothiazepin-2(R)-yl]propanamide;

3-Amino-3-methyl-N-[2,3,4,5-tetrahydro-8-methyl thio-4-[[2'-[[[(methylamino)carbonyl]amino]methyl][1,1'-biphenyl]-4-yl]methyl]- 3-oxo-1,4-benzothiazepin-2(R)-yl]butanamide;

3-[2(R)-Hydroxypropyl]amino-3-methyl-N-[2,3,4,5-tetrahydro- 8-methylthio-4-[[2'-[[[(methylamino)carbonyl]amino]methyl][1,1'-biphenyl]-4-yl]methyl]-3-oxo- 1,4-benzothiazepin-2(R)-yl]butanamide;

2-Amino-2-methyl-N-[2,3,4,5-tetrahydro-4-[[2'-[[(aminocarbonyl)-amino]methyl][1,1'-biphenyl]-4-yl]methyl]-3-oxo- 1,4-benzothiazepin-2(R)-yl]propanamide;

3-[2(S),3-Dihydroxypropyl]amino-3-methyl-N-[2,3,4,5-tetrahydro-4-[[2'-[[(aminocarbonyl)amino]methyl][1, 1'-biphenyl]-4-yl]methyl]- 3-oxo- 1,4-benzothiazepin-2(R)-yl]butanamide;

3-[2(R)-Hydroxypropyl]amino-3-methyl-N-[2,3,4,5-tetrahydro-4-[[2'-[[(aminocarbonyl)amino]methyl][1,1'-biphenyl]-4-yl]methyl]- 3-oxo- 1,4-benzothiazepin-2(R)-yl]butanamide;

2-Amino-2-methyl-N-[2,3,4,5-tetrahydro-8-fluoro-4-[[2'-[[(amino-carbonyl)amino]methyl][1,1'-biphenyl]-4-yl]methyl]-3-oxo- 1,4-benzothiazepin-2(R)-yl]propanamide;

3-[2(S),3-Dihydroxypropyl]amino-3-methyl-N-[2,3,4,5-tetrahydro- 8-fluoro-4-[[2'-[[(aminocarbonyl)amino]methyl][1,1'-biphenyl]- 4-yl]-methyl]-3-oxo-1,4-benzothiazepin-2(R)-yl]butanamide;

2-Amino-2-methyl-N-[2,3,4,5-tetrahydro-8-methoxy-4-[[2'-[[(amino-carbonyl)amino]methyl][1,1'-biphenyl]-4-yl]methyl]-3-oxo- 1,4-benzo-thiazepin-2(R)-yl]propanamide;

3-Amino-3-methyl-N-[2,3,4,5-tetrahydro-8-methoxy-4-[[2'-[[(amino-carbonyl)amino]methyl][1,1'-biphenyl]-4-yl]methyl]-3-oxo- 1,4-benzo-thiazepin-2(R)-yl]butanamide;

3-[2(S),3-Dihydroxypropyl]amino-3-methyl-N-[2,3,4,5-tetrahydro- 8-methylthio-4-[[2'-[[(aminocarbonyl)amino]methyl][1,1'-biphenyl]- 4-yl]-methyl]-3-oxo-1,4-benzothiazepin-2(R)-yl]butanamide;

3-[2(R)-Hydroxypropyl]amino-3-methyl-N-[2,3,4,5-tetrahydro- 8-methylthio-4-[[2'-[[(aminocarbonyl)amino]methyl][1,1'-biphenyl]- 4-yl]-methyl]-3-oxo-1,4-benzothiazepin-2(R)-yl]butanamide;

2-Amino-2-methyl-N-[2,3,4,5-tetrahydro-4-[[2'-[[[(ethylamino)-carbonyl]amino]methyl][1,1'-biphenyl]-4-yl]methyl]-3-oxo- 1,4-benzothiazepin-2(R)-yl]propanamide;

3-[2(S),3-Dihydroxypropyl]amino-3-methyl-N-[2,3,4,5-tetrahydro-4-[[2'-[[[(ethylamino)carbonyl]amino]methyl][1,1'-biphenyl]-4-yl]methyl]- 3-oxo-1,4-benzothiazepin-2(R)-yl]butanamide;

3-[2(R)-Hydroxypropyl]amino-3-methyl-N-[2,3,4,5-tetrahydro-4-[[2'-[[[(ethylamino)carbonyl]amino]methyl][1,1'-biphenyl]-4-yl]methyl]- 3-oxo-1,4-benzothiazepin-2(R)-yl]butanamide;

2-Amino-2-methyl-N-[2,3,4,5-tetrahydro-8-fluoro-4-[[2'-[[[(ethyl-amino)carbonyl]amino]methyl][1,1'-biphenyl]-4-yl]methyl]-3-oxo- 1,4-benzothiazepin-2(R)-yl]propanamide;

3-[2(S),3-Dihydroxypropyl]amino-3-methyl-N-[2,3,4,5-tetrahydro- 8-fluoro-4-[[2'-[[[(ethylamino)carbonyl]amino]methyl][1,1'-biphenyl]- 4-yl]methyl]-3-oxo-1, 4-benzothiazepin-2(R)-yl]butanamide;

2-Amino-2-methyl-N-[2,3,4,5-tetrahydro-8-methoxy-4-[[2'-[[[(ethyl-amino)carbonyl]amino]methyl][1,1'-biphenyl]-4-yl]methyl]-3-oxo- 1,4-benzothiazepin-2(R)-yl]propanamide;

3-[2(S),3-Dihydroxypropyl]amino-3-methyl-N-[2,3,4,5-tetrahydro- 8-methoxy-4-[[2'-[[[(ethylamino)carbonyl]amino]methyl][1,1'-biphenyl]-4-yl]methyl]-3-oxo-1,4-benzothiazepin-2(R)-yl]butanamide;

3-Amino-3-methyl-N-[2,3,4,5-tetrahydro-8-methylthio-4-[[2'-[[[(ethyl-amino)carbonyl]amino]methyl][1,1'-biphenyl]-4-yl]methyl]-3-oxo- 1,4-benzothiazepin-2(R)-yl]butanamide;

3-[2(S),3-Dihydroxypropyl]amino-3-methyl-N-[2,3,4,5-tetrahydro- 8-methylthio-4-[[2'-[[[(ethylamino)carbonyl]amino]methyl][1,1'-biphenyl]-4-yl]methyl]-3-oxo- 1,4-benzothiazepin-2(R)-yl]butanamide;

2-Amino-2-methyl-N-[2,3,4,5-tetrahydro-4-[[2'-[[[[(2-hydroxyethyl)-amino]carbonyl]amino]methyl][1,1'-biphenyl]-4-yl]methyl]-3-oxo- 1,4-benzothiazepin-2(R)-yl]propanamide;

3-Amino-3-methyl-N-[2,3,4,5-tetrahydro-4-[[2'-[[[[(2-hydroxyethyl)-amino]carbonyl]amino]methyl][1,1'-biphenyl]-4-yl]methyl]-3-oxo- 1,4-benzothiazepin-2(R)-yl]butanamide;

3-[2(S),3-Dihydroxypropyl]amino-3-methyl-N-[2,3,4,5-tetrahydro-4-[[2'-[[[[(2-hydroxyethyl)amino]carbonyl]amino]methyl][1,1'-biphenyl]- 4-yl]methyl]-3-oxo-1,4-benzothiazepin-2(R)-yl]butanamide;

3-[2(R)-Hydroxypropyl]amino-3-methyl-N-[2,3,4,5-tetrahydro-4-[[2'-[[[[(2-hydroxyethyl)amino]carbonyl]amino]methyl][1,1'-biphenyl]- 4-yl]-methyl]-3-oxo-1, 4-benzothiazepin-2(R)-yl]butanamide;

2-Amino-2-methyl-N-[2,3,4,5-tetrahydro-8-fluoro-4-[[2'-[[[[(2-hydroxyethyl)amino]carbonyl]amino]methyl][1,1'-biphenyl]- 4-yl]-methyl]-3-oxo-1,4-benzothiazepin-2(R)-yl]propanamide;

3-[2(S),3-Dihydroxypropyl]amino-3-methyl-N-[2,3,4,5-tetrahydro- 8-fluoro-4-[[2'-[[[[(2-hydroxyethyl)amino]carbonyl]amino]methyl][1,1'-biphenyl]-4-yl]methyl]-3-oxo-1,4-benzothiazepin-2(R)-yl]butanamide;

2-Amino-2-methyl-N-[2,3,4,5-tetrahydro-8-methoxy-4-[[2'-[[[[(2-hydroxyethyl)amino]carbonyl]amino]methyl][1,1'-biphenyl]- 4-yl]-methyl]-3-oxo-1,4-benzothiazepin-2(R)-yl]propanamide;

3-[2(R)-Hydroxypropyl]amino-3-methyl-N-[2,3,4,5-tetrahydro- 8-methoxy-4-[[2'-[[[[(2-hydroxyethyl)amino]carbonyl]amino]methyl][1,1'-biphenyl]-4-yl]methyl]-3-oxo-1,4-benzothiazepin-2(R)-yl]butanamide;

3-[2(S),3-Dihydroxypropyl]amino-3-methyl-N-[2,3,4,5-tetrahydro- 8-methylthio-4-[[2'-[[[[(2-hydroxyethyl)amino]carbonyl]amino]methyl]-[1,1'-biphenyl]-4-yl]methyl]-3-oxo-1,4-benzothiazepin-2(R)-yl]-butanamide;

3-[2(R)-Hydroxypropyl]amino-3-methyl-N-[2,3,4,5-tetrahydro- 8-methylthio-4-[[2'- [[[[(2-hydroxyethyl)amino]carbonyl]amino]methyl]-[1,1'-biphenyl]-4-yl] methyl]-3-oxo-1,4-benzothiazepin-2(R)-yl]-butanamide;

2-Amino-2-methyl-N-[2,3,4,5-tetrahydro-4-[[2'-[2-[[(methylamino)-carbonyl]amino]prop-2-yl][1,1'-biphenyl]-4-yl]methyl]-3-oxo- 1,4-benzothiazepin-2(R)-yl]propanamide;

2-Amino-2-methyl-N-[2,3,4,5-tetrahydro-4-[[2'-[1-[[(methylamino)-carbonyl]amino]ethyl][1,1'-biphenyl]-4-yl]methyl]-3-oxo- 1,4-benzo-thiazepin-2(R)-yl]propanamide;

2-Amino-2-methyl-N-[2,3,4,5-tetrahydro-4-[[2'-[[(methoxycarbonyl)-amino]methyl][1,1'-biphenyl]-4-yl]methyl]-3-oxo-1,4-benzothiazepin- 2(R)-yl]propanamide;

3-Amino-3-methyl-N-[2,3,4,5-tetrahydro-4-[[2'-[[(methoxycarbonyl)-amino]methyl][1,1'-biphenyl]-4-yl]methyl]-3-oxo-1,4-benzothiazepin- 2(R )-yl]butanamide;

3-[2(R)-Hydroxypropyl]amino-3-methyl-N-[2,3,4,5-tetrahydro-4-[[2'-[[(methoxycarbonyl)amino]methyl][1,1'-biphenyl]-4-yl]methyl]- 3-oxo-1,4-benzothiazepin-2(R)-yl]butanamide; and 3-[2(S),3-Dihydroxypropyl]amino-3-methyl-N-[2,3,4,5-tetrahydro-4-[[2'-[[(methoxycarbonyl)amino]methyl][1,1'-biphenyl]-4-yl]methyl]- 3-oxo-1,4-benzothiazepin-2(R)-yl]butanamide;

or a pharmaceutically acceptable salt thereof.

* * * * *